United States Patent [19]

Suzuki et al.

[11] Patent Number: 4,954,164

[45] Date of Patent: Sep. 4, 1990

[54] PYRAZOLESULFONYLUREA DERIVATIVES, PREPARATION THEREOF, HERBICIDE CONTAINING SAID DERIVATIVE AS ACTIVE INGREDIENT AND HERBICIDAL METHOD BY USE THEREOF

[75] Inventors: Fumio Suzuki, Onoda; Yoshihiro Iwasawa, Ichikawa; Toshiaki Sato, Funabashi; Takasi Ikai, Tokyo; Tosihiko Oguti, Urawa, all of Japan

[73] Assignee: Nissan Chemical Industries, Ltd., Tokyo, Japan

[21] Appl. No.: 469,458

[22] Filed: Feb. 24, 1983

[30] Foreign Application Priority Data

Feb. 27, 1982 [JP] Japan .................................. 57-31377
Aug. 18, 1982 [JP] Japan ................................ 57-142069

[51] Int. Cl.$^5$ ..................... A01N 43/54; A01N 43/66; C07D 239/47
[52] U.S. Cl. ........................................ 71/92; 71/93; 544/212; 544/298; 544/320; 544/331
[58] Field of Search ............... 544/320, 331, 333, 334, 544/335; 71/92

[56] References Cited

U.S. PATENT DOCUMENTS

| | | | |
|---|---|---|---|
| 4,017,298 | 4/1977 | Cross et al. | 71/92 |
| 4,146,726 | 3/1979 | Konotsune et al. | 71/92 |
| 4,261,729 | 4/1981 | Konotsune et al. | 71/92 |
| 4,301,293 | 11/1981 | Konotsune et al. | 71/92 |
| 4,368,067 | 1/1983 | Budzinski et al. | 71/92 |
| 4,369,058 | 1/1983 | Levitt | 544/320 |
| 4,425,151 | 1/1984 | Sturm et al. | 71/93 |

FOREIGN PATENT DOCUMENTS 58-670 of 1982 Japan .
2276 of 1982 Japan .

*Primary Examiner*—Cecelia Shen
*Attorney, Agent, or Firm*—Frishauf, Holtz, Goodman & Woodward

[57] ABSTRACT

Disclosed is a novel pyrazolesulfonylurea derivative represented by the formula (I), preparation thereof, a herbicide containing said derivative as an active ingredient and a herbicidal method by use thereof.

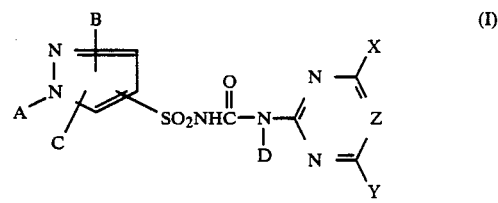

(wherein A, B, C, D, X, Y and Z are as defined in the specification).

5 Claims, No Drawings

PYRAZOLESULFONYLUREA DERIVATIVES, PREPARATION THEREOF, HERBICIDE CONTAINING SAID DERIVATIVE AS ACTIVE INGREDIENT AND HERBICIDAL METHOD BY USE THEREOF

This invention relates to a novel pyrazolesulfonylurea derivative represented by the formula (I), preparation thereof, a herbicide containing said derivative as an active ingredient and a herbicidal method by use thereof.

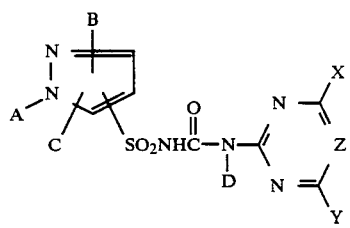

wherein A represents a hydrogen atom, a $C_1$–$C_8$ alkyl group or a phenyl group which may be substituted with $C_1$–$C_8$ alkyl groups, halogen atoms or nitro groups; B and C represent independently hydrogen atoms, halogen atoms, nitro groups, $C_1$–$C_8$ alkyl groups, arylalkyl groups, $C_1$–$C_8$ alkoxy groups, haloalkyl groups, —$CO_2R$ (where R is a hydrogen atom, a $C_1$–$C_8$ alkyl group, an allyl group or a propargyl group), —$CONR_1R_2$ [where $R_1$ is a hydrogen atom, a $C_1$–$C_8$ alkyl group or a phenyl group, $R_2$ is a hydrogen atom or a $C_1$–$C_8$ alkyl group, or $R_1$ and $R_2$ taken together may represent —$(CH_2)_m$— (m is 4, 5 or 6), —$CH_2CH_2OCH_2CH_2$— or —$CH_2CH_2N(CH_3)CH_2CH_2$—], —$S(O)_nR_3$ (where $R_3$ is a $C_1$–$C_8$ alkyl group, a phenyl group or an arylalkyl group and n is 0, 1 or 2), —$SO_2NR_4R_5$ [where $R_4$ is a $C_1$–$C_8$ alkyl group, $R_5$ is a hydrogen atom or a $C_1$–$C_8$ alkyl group, or $R_4$ and $R_5$ taken together may represent —$(CH_2)_p$— (p is 4, 5 or 6), —$CH_2CH_2OCH_2CH_2$— or —$CH_2CH_2N(CH_3)CH_2CH_2$—] or a phenyl group which may be substituted with $C_1$–$C_8$ alkyl groups, halogen atoms or nitro groups; D represents a hydrogen atom or a $C_1$–$C_8$ alkyl group; X and Y represent independently hydrogen atoms, halogen atoms, $C_1$–$C_8$ alkyl groups, $C_1$–$C_8$ alkoxy groups, $C_1$–$C_8$ alkoxyalkyl groups, —$CF_3$ groups, $C_1$–$C_8$ haloalkoxy groups, alkylamino goups, dialkylamino groups,

(where $R_6$ and $R_7$ each represent hydrogen atoms or $C_1$–$C_8$ alkyl groups) or either X or Y may form a five-membered ring containing an oxygen atom together with Z; and Z represents a nitrogen atom or C-$R_8$ (where $R_8$ represents a hydrogen atom, a haloalkyl group or may form a five-membered ring containing an oxygen atom together with X or Y).

The compounds of this invention are novel compounds not disclosed in literatures and have excellent herbicidal activities.

Japanese Unexamined Patent Publication Nos. 102577/1980 and 139466/1981 disclose pyridinesulfonylurea derivatives and Japanese Unexamined Patent Publication No. 169688/1981 discloses pyrolesulfonylurea derivatives, respectively, as useful herbicides Heretofore, in using herbicides, it has been pointed out that the economical cost involved in the use of a herbicide depends on the application amount of the active ingredient per unit area. For this reason, studies have been continued for many years to obtain compounds which can exhibit high herbicidal effects at lower application rate.

In the prior art, as pyrazole derivatives, there have been known a large number of compounds, as disclosed in Japanese Patent Publication No. 36648/1979 and Japanese Unexamined Patent Publication Nos. 41872/1979, 2276/1982, 58670/1982 and 133265/1976.

The present inventors have made various investigations for many years and consequently found that the compounds of this invention have markedly high herbicidal effects as compared with the above pyrazole derivatives known in the art and are practically useful. On the other hand, as sulfonylurea derivatives containing a nitrogen-containing heterocyclic ring, the aforementioned pyrolesulfonylurea and pyridinesulfonylurea are known. As compared with these known compounds, the compounds of this invention have been found to exhibit markedly higher herbicidal effects. The present invention has been accomplished on the basis of these findings.

That is, the compounds of this invention may be said to be epoch-making herbicides capable of decreasing markedly the amount of the active ingredient applied per unit area as compared with these compounds known in the art, having a very great economical effect as compared with the herbicides of the prior art, and also capable of alleviating markedly the environmental pollution which may be caused by application of a large amount of pesticides.

Typical examples of the derivatives represented by the above formula (I) suitable for use as herbicides may include those as shown in Table 1, Table 2 and Table 3 set forth below.

The Compounds Nos. in these Tables are referred to in the following description.

TABLE 1

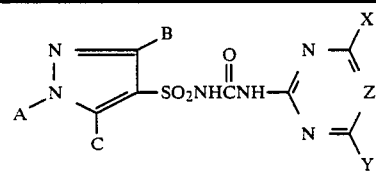

| Comp. No. | A | B | C | X | Y | Z |
|---|---|---|---|---|---|---|
| 1 | $CH_3$ | $CH_3$ | $CH_3$ | $CH_3$ | $CH_3$ | CH |
| 2 | $CH_3$ | $CH_3$ | $CH_3$ | $CH_3$ | $OCH_3$ | CH |

TABLE 1-continued

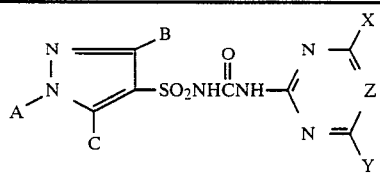

| Comp. No. | A | B | C | X | Y | Z |
|---|---|---|---|---|---|---|
| 3 | $CH_3$ | $CH_3$ | $CH_3$ | $OCH_3$ | $OCH_3$ | CH |
| 4 | $CH_3$ | $CH_3$ | $CH_3$ | $CH_3$ | $OCH_3$ | N |
| 5 | $CH_3$ | $CH_3$ | $CH_3$ | $OCH_3$ | $OCH_3$ | N |
| 6 | C₆H₅ | $CH_3$ | $CH_3$ | $CH_3$ | H | CH |
| 7 | C₆H₅ | $CH_3$ | $CH_3$ | $CH_3$ | $CH_3$ | CH |
| 8 | C₆H₅ | $CH_3$ | $CH_3$ | $CH_3$ | $OCH_3$ | CH |
| 9 | C₆H₅ | $CH_3$ | $CH_3$ | $OCH_3$ | $OCH_3$ | CH |
| 10 | C₆H₅ | $CH_3$ | $CH_3$ | $CH_3$ | $OCH_3$ | N |
| 11 | C₆H₅ | $CH_3$ | $CH_3$ | $OCH_3$ | $OCH_3$ | N |
| 12 | $CH_3$ | C₆H₅ | $CH_3$ | $CH_3$ | $CH_3$ | CH |
| 13 | $CH_3$ | C₆H₅ | $CH_3$ | $CH_3$ | $OCH_3$ | CH |
| 14 | $CH_3$ | C₆H₅ | $CH_3$ | $OCH_3$ | $OCH_3$ | CH |
| 15 | $CH_3$ | C₆H₅ | $CH_3$ | $CH_3$ | $OCH_3$ | N |
| 16 | $CH_3$ | C₆H₅ | $CH_3$ | $OCH_3$ | $OCH_3$ | N |

TABLE 1-continued
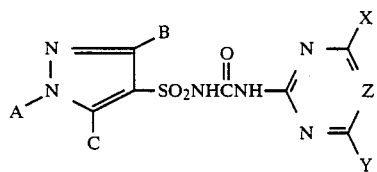
| Comp. No. | A | B | C | X | Y | Z |
|---|---|---|---|---|---|---|
| 17 | CH₃ | ⌬ | CH₃ | CH₃ | CH₃ | N |
| 18 | CH₃ | ⌬ | CH₃ | CH₃ | Cl | CH |
| 19 | CH₃ | ⌬ | CH₃ | CH₃ | Cl | C(CH₂)₂Cl |
| 20 | CH₃ | ⌬ | CH₃ | CH₃ | —OCH₂CH₂C— | |
| 21 | CH₃ | ⌬ | CH₃ | Cl | N(CH₃)₂ | N |
| 22 | CH₃ | ⌬ | CH₃ | OCH₃ | N(CH₃)₂ | N |
| 23 | CH₃ | ⌬—CH₃ | CH₃ | CH₃ | CH₃ | CH |
| 24 | CH₃ | ⌬—CH₃ | CH₃ | CH₃ | OCH₃ | CH |
| 25 | CH₃ | ⌬—CH₃ | CH₃ | CH₃ | OCH₃ | N |
| 26 | CH₃ | ⌬—C₂H₅ | CH₃ | CH₃ | OCH₃ | CH |
| 27 | CH₃ | ⌬—C₂H₅ | CH₃ | CH₃ | OCH₃ | N |

TABLE 1-continued

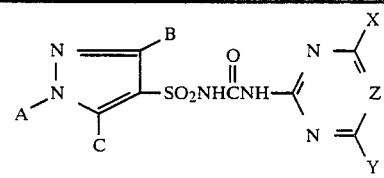

| Comp. No. | A | B | C | X | Y | Z |
|---|---|---|---|---|---|---|
| 28 | $CH_3$ | 3,5-dimethylphenyl | $CH_3$ | $CH_3$ | $CH_3$ | CH |
| 29 | $CH_3$ | 3,5-dimethylphenyl | $CH_3$ | $CH_3$ | $OCH_3$ | CH |
| 30 | $CH_3$ | 3,5-dimethylphenyl | $CH_3$ | $CH_3$ | $OCH_3$ | N |
| 31 | $CH_3$ | 2,6-dimethylphenyl | $CH_3$ | $CH_3$ | $CH_3$ | CH |
| 32 | $CH_3$ | 2,6-dimethylphenyl | $CH_3$ | $CH_3$ | $OCH_3$ | CH |
| 33 | $CH_3$ | 2,6-dimethylphenyl | $CH_3$ | $CH_3$ | $OCH_3$ | N |
| 34 | $CH_3$ | 4-chlorophenyl | $CH_3$ | $CH_3$ | $OCH_3$ | CH |
| 35 | $CH_3$ | 4-chlorophenyl | $CH_3$ | $CH_3$ | $OCH_3$ | N |
| 36 | $CH_3$ | 2-chlorophenyl | $CH_3$ | $CH_3$ | $OCH_3$ | CH |
| 37 | $CH_3$ | 2-chlorophenyl | $CH_3$ | $CH_3$ | $OCH_3$ | N |

TABLE 1-continued

| Comp. No. | A | B | C | X | Y | Z |
|---|---|---|---|---|---|---|
| 38 | CH₃ | C₆H₄-NO₂ | CH₃ | CH₃ | OCH₃ | CH |
| 39 | CH₃ | C₆H₄-NO₂ | CH₃ | CH₃ | OCH₃ | N |
| 40 | CH₃ | C₆H₅ | H | CH₃ | CH₃ | CH |
| 41 | CH₃ | C₆H₅ | H | CH₃ | OCH₃ | CH |
| 42 | CH₃ | C₆H₅ | H | CH₃ | OCH₃ | N |
| 43 | CH₃ | CH₃ | C₆H₅ | CH₃ | CH₃ | CH |
| 44 | CH₃ | CH₃ | C₆H₅ | CH₃ | OCH₃ | CH |
| 45 | CH₃ | CH₃ | C₆H₅ | OCH₃ | OCH₃ | CH |
| 46 | CH₃ | CH₃ | C₆H₅ | CH₃ | OCH₃ | N |
| 47 | CH₃ | CH₃ | C₆H₅ | OCH₃ | OCH₃ | N |
| 48 | H | C₆H₅ | CH₃ | CH₃ | CH₃ | CH |
| 49 | H | C₆H₅ | CH₃ | CH₃ | OCH₃ | CH |

TABLE 1-continued
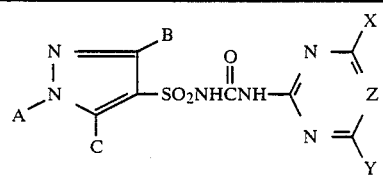
| Comp. No. | A | B | C | X | Y | Z |
|---|---|---|---|---|---|---|
| 50 | H | Ph | CH₃ | CH₃ | OCH₃ | N |
| 51 | —CH₂CH₃ | Ph | CH₃ | CH₃ | CH₃ | CH |
| 52 | —CH₂CH₃ | Ph | CH₃ | CH₃ | OCH₃ | CH |
| 53 | —CH₂CH₃ | Ph | CH₃ | CH₃ | OCH₃ | N |
| 54 | —CH₂CH₂CH₃ | Ph | CH₃ | CH₃ | CH₃ | CH |
| 55 | —CH₂CH₂CH₃ | Ph | CH₃ | CH₃ | OCH₃ | CH |
| 56 | —CH₂CH₂CH₃ | Ph | CH₃ | CH₃ | OCH₃ | N |
| 57 | Ph | Ph | CH₃ | CH₃ | CH₃ | CH |
| 58 | Ph | Ph | CH₃ | CH₃ | OCH₃ | CH |
| 59 | Ph | Ph | CH₃ | CH₃ | OCH₃ | N |
| 60 | CH₃ | Ph | Ph | CH₃ | CH₃ | CH |

TABLE 1-continued
| Comp. No. | A | B | C | X | Y | Z |
|---|---|---|---|---|---|---|
| 61 | CH₃ |  |  | CH₃ | OCH₃ | CH |
| 62 | CH₃ |  |  | CH₃ | OCH₃ | N |
| 63 | H |  |  | CH₃ | CH₃ | CH |
| 64 | H |  |  | CH₃ | OCH₃ | CH |
| 65 | H |  |  | CH₃ | OCH₃ | N |
| 66 | CH₃ |  | OCH₃ | CH₃ | CH₃ | CH |
| 67 | CH₃ |  | OCH₃ | CH₃ | OCH₃ | CH |
| 68 | CH₃ |  | OCH₃ | OCH₃ | OCH₃ | CH |
| 69 | CH₃ |  | OCH₃ | OCH₂CH₃ | OCH₂CH₃ | CH |
| 70 | CH₃ |  | OCH₃ | CH₃ | OCH₃ | N |
| 71 | CH₃ |  | OCH₃ | OCH₃ | OCH₃ | N |
| 72 | CH₃ |  | OCH₃ | CH₃ | CH₃ | N |

TABLE 1-continued
| Comp. No. | A | B | C | X | Y | Z |
|---|---|---|---|---|---|---|
| 73 | CH₃ |  | OCH₃ | CH₃ | Cl | C(CH₂)₂Cl |
| 74 | CH₃ |  | OCH₃ | CH₃ | —OCH₂CH₂C— | |
| 75 | CH₃ | 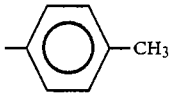 | OCH₃ | OCH₃ | N(CH₃)₂ | N |
| 76 | CH₃ | 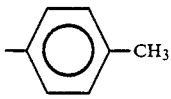 (4-CH₃-phenyl) | OCH₃ | CH₃ | CH₃ | CH |
| 77 | CH₃ | 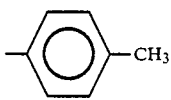 (4-CH₃-phenyl) | OCH₃ | CH₃ | OCH₃ | CH |
| 78 | CH₃ | 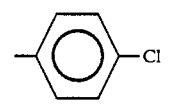 (4-CH₃-phenyl) | OCH₃ | CH₃ | OCH₃ | N |
| 79 | CH₃ | 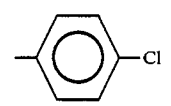 (4-Cl-phenyl) | OCH₃ | CH₃ | CH₃ | CH |
| 80 | CH₃ | 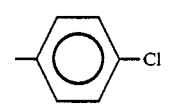 (4-Cl-phenyl) | OCH₃ | CH₃ | OCH₃ | CH |
| 81 | CH₃ | 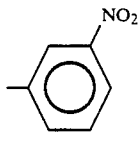 (4-Cl-phenyl) | OCH₃ | CH₃ | OCH₃ | N |
| 82 | CH₃ | 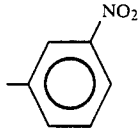 (NO₂-phenyl) | OCH₃ | CH₃ | CH₃ | CH |
| 83 | CH₃ | (NO₂-phenyl) | OCH₃ | CH₃ | OCH₃ | CH |

TABLE 1-continued

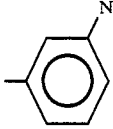

| Comp. No. | A | B | C | X | Y | Z |
|---|---|---|---|---|---|---|
| 84 | CH₃ |  (NO₂-phenyl) | OCH₃ | CH₃ | OCH₃ | N |
| 85 | CH₃ | CH₃ | Cl | CH₃ | CH₃ | CH |
| 86 | CH₃ | CH₃ | Cl | CH₃ | OCH₃ | CH |
| 87 | CH₃ | CH₃ | Cl | OCH₃ | OCH₃ | CH |
| 88 | CH₃ | CH₃ | Cl | CH₃ | OCH₃ | N |
| 89 | CH₃ | CH₃ | Cl | OCH₃ | OCH₃ | N |
| 90 | CH₃ | CH₃ | Cl | CH₃ | CH₃ | N |
| 91 | CH₃ | CH₃ | Cl | CH₃ | Cl | C(CH₂)₂Cl |
| 92 | CH₃ | CH₃ | Cl | CH₃ | —OCH₂CH₂C— | |
| 93 | CH₃ | CH₃ | Cl | OCH₃ | N(CH₃)₂ | N |
| 94 | CH₃ | CH₃ | Cl | CH₂CH₃ | OCH₃ | CH |
| 95 | CH₃ | CH₃ | Cl | CH₃ | CH₂OCH₃ | CH |
| 96 | CH₃ | CH₃ | Cl | CH₃ | OCH₂CO₂CH₃ | CH |
| 97 | CH₃ |  (phenyl) | Cl | CH₃ | CH₃ | CH |
| 98 | CH₃ |  (phenyl) | Cl | CH₃ | OCH₃ | CH |
| 99 | CH₃ |  (phenyl) | Cl | OCH₃ | OCH₃ | CH |
| 100 | CH₃ |  (phenyl) | Cl | CH₃ | OCH₃ | N |
| 101 | CH₃ | 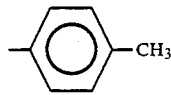 (phenyl) | Cl | OCH₃ | OCH₃ | N |
| 102 | CH₃ | 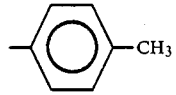 (CH₃-phenyl) | Cl | CH₃ | CH₃ | CH |
| 103 | CH₃ | (CH₃-phenyl) | Cl | CH₃ | OCH₃ | CH |
| 104 | CH₃ | 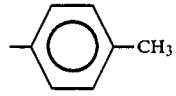 (CH₃-phenyl) | Cl | CH₃ | OCH₃ | N |
| 105 | CH₃ | CH₃ | Br | CH₃ | CH₃ | CH |
| 106 | CH₃ | CH₃ | Br | CH₃ | OCH₃ | CH |
| 107 | CH₃ | CH₃ | Br | OCH₃ | OCH₃ | CH |

TABLE 1-continued

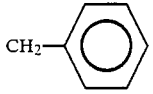

| Comp. No. | A | B | C | X | Y | Z |
|---|---|---|---|---|---|---|
| 108 | $CH_3$ | $CH_3$ | Br | $CH_3$ | $OCH_3$ | N |
| 109 | $CH_3$ | $CH_3$ | Br | $OCH_3$ | $OCH_3$ | N |
| 110 | $CH_3$ | H | Cl | $CH_3$ | $CH_3$ | CH |
| 111 | $CH_3$ | H | Cl | $CH_3$ | $OCH_3$ | CH |
| 112 | $CH_3$ | H | Cl | $OCH_3$ | $OCH_3$ | CH |
| 113 | $CH_3$ | H | Cl | $CH_3$ | $OCH_3$ | N |
| 114 | $CH_3$ | H | Cl | $OCH_3$ | $OCH_3$ | N |
| 115 | $CH_3$ | $CH_2CH_3$ | Cl | $CH_3$ | $CH_3$ | CH |
| 116 | $CH_3$ | $CH_2CH_3$ | Cl | $CH_3$ | $OCH_3$ | CH |
| 117 | $CH_3$ | $CH_2CH_3$ | Cl | $CH_3$ | $OCH_3$ | N |
| 118 | $CH_3$ | $CH_2CH_2CH_3$ | Cl | $CH_3$ | $CH_3$ | CH |
| 119 | $CH_3$ | $CH_2CH_2CH_3$ | Cl | $CH_3$ | $OCH_3$ | CH |
| 120 | $CH_3$ | $CH_2CH_2CH_3$ | Cl | $CH_3$ | $OCH_3$ | CH |
| 121 | $CH_3$ | $CH(CH_3)_2$ | Cl | $CH_3$ | $CH_3$ | CH |
| 122 | $CH_3$ | $CH(CH_3)_2$ | Cl | $CH_3$ | $OCH_3$ | CH |
| 123 | $CH_3$ | $CH(CH_3)_2$ | Cl | $CH_3$ | $OCH_3$ | CH |
| 124 | H | $CH_3$ | Cl | $CH_3$ | $CH_3$ | CH |
| 125 | H | $CH_3$ | Cl | $CH_3$ | $OCH_3$ | CH |
| 126 | H | $CH_3$ | Cl | $CH_3$ | $OCH_3$ | N |
| 127 | 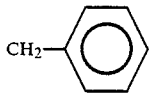 | $CH_3$ | Cl | $CH_3$ | $CH_3$ | CH |
| 128 | 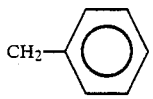 | $CH_3$ | Cl | $CH_3$ | $OCH_3$ | CH |
| 129 | 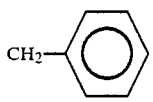 | $CH_3$ | Cl | $CH_3$ | $OCH_3$ | N |
| 130 | $CH_3$ | $CH_2$-Ph | $CH_3$ | $CH_3$ | $CH_3$ | CH |
| 131 | $CH_3$ | $CH_2$-Ph | $CH_3$ | $CH_3$ | $OCH_3$ | CH |
| 132 | $CH_3$ | $CH_2$-Ph | $CH_3$ | $OCH_3$ | $OCH_3$ | CH |
| 133 | $CH_3$ | $CH_2$-Ph | $CH_3$ | $CH_3$ | $OCH_3$ | N |
| 134 | $CH_3$ | $CH_2$-Ph | $CH_3$ | $OCH_3$ | $OCH_3$ | N |

TABLE 1-continued

Structure:
Pyrazole ring with N-N, substituent A on N, B at one position, C at another, and —SO$_2$NHCNH— (with C=O) linked to a triazine/pyrimidine ring with substituents X, Y, Z.

| Comp. No. | A | B | C | X | Y | Z |
|---|---|---|---|---|---|---|
| 135 | CH$_3$ | CH$_3$ | CH$_3$—(phenyl) | CH$_3$ | CH$_3$ | CH |
| 136 | CH$_3$ | CH$_3$ | CH$_2$—(phenyl) | CH$_3$ | OCH$_3$ | CH |
| 137 | CH$_3$ | CH$_3$ | CH$_2$—(phenyl) | CH$_3$ | OCH$_3$ | N |
| 138 | CH$_3$ | CF$_3$ | CH$_3$ | CH$_3$ | CH$_3$ | CH |
| 139 | CH$_3$ | CF$_3$ | CH$_3$ | CH$_3$ | OCH$_3$ | CH |
| 140 | CH$_3$ | CF$_3$ | CH$_3$ | OCH$_3$ | OCH$_3$ | CH |
| 141 | CH$_3$ | CF$_3$ | CH$_3$ | CH$_3$ | OCH$_3$ | N |
| 142 | CH$_3$ | CF$_3$ | CH$_3$ | OCH$_3$ | OCH$_3$ | N |
| 143 | CH$_3$ | CF$_3$ | CH$_3$ | CH$_3$ | CH$_3$ | N |
| 144 | CH$_3$ | CF$_3$ | CH$_3$ | CH$_3$ | Cl | N |
| 145 | CH$_3$ | CF$_3$ | CH$_3$ | CH$_3$ | Cl | C(CH$_2$)$_2$Cl |
| 146 | CH$_3$ | CF$_3$ | CH$_3$ | CH$_3$ | —OCH$_2$CH$_2$C— | |
| 147 | CH$_3$ | CF$_3$ | CH$_3$ | Cl | N(CH$_3$)$_2$ | N |
| 148 | CH$_3$ | CF$_3$ | CH$_3$ | OCH$_3$ | N(CH$_3$)$_2$ | N |
| 149 | CH$_3$ | CF$_3$ | CH$_3$ | OCH$_2$CH$_3$ | NHCH$_3$ | N |
| 150 | CH$_3$ | CF$_3$ | CH$_3$ | CH$_3$ | Cl | CH |
| 151 | CH$_3$ | CF$_3$ | CH$_3$ | Cl | Cl | CH |
| 152 | H | CF$_3$ | CH$_3$ | CH$_3$ | CH$_3$ | CH |
| 153 | H | CF$_3$ | CH$_3$ | CH$_3$ | OCH$_3$ | CH |
| 154 | H | CF$_3$ | CH$_3$ | CH$_3$ | OCH$_3$ | N |
| 155 | phenyl | CF$_3$ | CH$_3$ | CH$_3$ | CH$_3$ | CH |
| 156 | phenyl | CF$_3$ | CH$_3$ | CH$_3$ | OCH$_3$ | CH |
| 157 | phenyl | CF$_3$ | CH$_3$ | CH$_3$ | OCH$_3$ | N |
| 158 | CH$_3$ | CO$_2$CH$_3$ | CH$_3$ | CH$_3$ | CH$_3$ | CH |
| 159 | CH$_3$ | CO$_2$CH$_3$ | CH$_3$ | CH$_3$ | OCH$_3$ | CH |
| 160 | CH$_3$ | CO$_2$CH$_3$ | CH$_3$ | OCH$_3$ | OCH$_3$ | CH |
| 161 | CH$_3$ | CO$_2$CH$_3$ | CH$_3$ | CH$_3$ | OCH$_3$ | N |
| 162 | CH$_3$ | CO$_2$CH$_3$ | CH$_3$ | OCH$_3$ | OCH$_3$ | N |
| 163 | CH$_3$ | CO$_2$CH$_3$ | CH$_3$ | CH$_3$ | CH$_3$ | N |
| 164 | CH$_3$ | CO$_2$CH$_3$ | CH$_3$ | CH$_3$ | Cl | N |
| 165 | CH$_3$ | CO$_2$CH$_3$ | CH$_3$ | CH$_3$ | Cl | C(CH$_2$)$_2$Cl |
| 166 | CH$_3$ | CO$_2$CH$_3$ | CH$_3$ | CH$_3$ | —OCH$_2$CH$_2$C— | |
| 167 | CH$_3$ | CO$_2$CH$_3$ | CH$_3$ | Cl | N(CH$_3$)$_2$ | N |
| 168 | CH$_3$ | CO$_2$CH$_3$ | CH$_3$ | OCH$_3$ | N(CH$_3$)$_2$ | N |
| 169 | CH$_3$ | CO$_2$CH$_3$ | CH$_3$ | Cl | CH$_3$ | CH |
| 170 | CH$_3$ | CO$_2$CH$_3$ | CH$_3$ | CH$_3$ | OCH$_2$CH$_3$ | CH |
| 171 | CH$_3$ | CO$_2$CH$_3$ | CH$_3$ | CH$_3$ | OCH$_2$CH$_3$ | N |
| 172 | CH$_3$ | CO$_2$CH$_3$ | CH$_3$ | CH$_3$ | NHCH$_3$ | N |
| 173 | CH$_3$ | CO$_2$CH$_3$ | CH$_3$ | CH$_3$ | H | CH |
| 174 | CH$_3$ | CO$_2$CH$_3$ | CH$_3$ | H | H | CH |

TABLE 1-continued

| Comp. No. | A | B | C | X | Y | Z |
|---|---|---|---|---|---|---|
| 175 | $CH_3$ | $CO_2CH_3$ | $CH_3$ | Cl | Cl | CH |
| 176 | $CH_3$ | $CO_2CH_2CH_3$ | $CH_3$ | $CH_3$ | $CH_3$ | CH |
| 177 | $CH_3$ | $CO_2CH_2CH_3$ | $CH_3$ | $CH_3$ | $OCH_3$ | CH |
| 178 | $CH_3$ | $CO_2CH_2CH_3$ | $CH_3$ | $OCH_3$ | $OCH_3$ | CH |
| 179 | $CH_3$ | $CO_2CH_2CH_3$ | $CH_3$ | $CH_3$ | $OCH_3$ | N |
| 180 | $CH_3$ | $CO_2CH_2CH_3$ | $CH_3$ | $OCH_3$ | $OCH_3$ | N |
| 181 | $CH_3$ | $CO_2CH_2CH_3$ | $CH_3$ | $CH_3$ | $CH_3$ | N |
| 182 | $CH_3$ | $CO_2C_3H_7\text{-}n$ | $CH_3$ | $CH_3$ | $CH_3$ | CH |
| 183 | $CH_3$ | $CO_2C_3H_7\text{-}n$ | $CH_3$ | $CH_3$ | $OCH_3$ | CH |
| 184 | $CH_3$ | $CO_2C_3H_7\text{-}n$ | $CH_3$ | $OCH_3$ | $OCH_3$ | CH |
| 185 | $CH_3$ | $CO_2C_3H_7\text{-}n$ | $CH_3$ | $CH_3$ | $OCH_3$ | N |
| 186 | $CH_3$ | $CO_2C_3H_7\text{-}n$ | $CH_3$ | $OCH_3$ | $OCH_3$ | N |
| 187 | $CH_3$ | $CO_2C_3H_7\text{-}i$ | $CH_3$ | $CH_3$ | $CH_3$ | CH |
| 188 | $CH_3$ | $CO_2C_3H_7\text{-}i$ | $CH_3$ | $CH_3$ | $OCH_3$ | CH |
| 189 | $CH_3$ | $CO_2C_3H_7\text{-}i$ | $CH_3$ | $OCH_3$ | $OCH_3$ | CH |
| 190 | $CH_3$ | $CO_2C_3H_7\text{-}i$ | $CH_3$ | $CH_3$ | $OCH_3$ | N |
| 191 | $CH_3$ | $CO_2C_3H_7\text{-}i$ | $CH_3$ | $OCH_3$ | $OCH_3$ | N |
| 192 | $CH_3$ | $CO_2CH_2CH=CH_2$ | $CH_3$ | $CH_3$ | $CH_3$ | CH |
| 193 | $CH_3$ | $CO_2CH_2CH=CH_3$ | $CH_3$ | $CH_3$ | $OCH_3$ | CH |
| 194 | $CH_3$ | $CO_2CH_2CH=CH_2$ | $CH_3$ | $OCH_3$ | $OCH_3$ | CH |
| 195 | $CH_3$ | $CO_2CH_2CH=CH_2$ | $CH_3$ | $CH_3$ | $OCH_3$ | N |
| 196 | $CH_3$ | $CO_2CH_2CH=CH_2$ | $CH_3$ | $OCH_3$ | $OCH_3$ | N |
| 197 | $CH_3$ | $CO_2CH_2C\equiv CH$ | $CH_3$ | $CH_3$ | $CH_3$ | CH |
| 198 | $CH_3$ | $CO_2CH_2C\equiv CH$ | $CH_3$ | $CH_3$ | $CH_3$ | CH |
| 199 | $CH_3$ | $CO_2CH_2C\equiv CH$ | $CH_3$ | $CH_3$ | $OCH_3$ | N |
| 200 | $CH_3$ | $CO_2H$ | $CH_3$ | $CH_3$ | $CH_3$ | CH |
| 201 | $CH_3$ | $CO_2H$ | $CH_3$ | $CH_3$ | $OCH_3$ | CH |
| 202 | $CH_3$ | $CO_2H$ | $CH_3$ | $OCH_3$ | $OCH_3$ | CH |
| 203 | $CH_3$ | $CO_2H$ | $CH_3$ | $CH_3$ | $OCH_3$ | N |
| 204 | $CH_3$ | $CO_2H$ | $CH_3$ | $OCH_3$ | $OCH_3$ | N |
| 205 | H | $CO_2CH_3$ | $CH_3$ | $CH_3$ | $CH_3$ | CH |
| 206 | H | $CO_2CH_3$ | $CH_3$ | $CH_3$ | $OCH_3$ | CH |
| 207 | H | $CO_2CH_3$ | $CH_3$ | $OCH_3$ | $OCH_3$ | CH |
| 208 | H | $CO_2CH_3$ | $CH_3$ | $CH_3$ | $OCH_3$ | N |
| 209 | H | $CO_2CH_3$ | $CH_3$ | $OCH_3$ | $OCH_3$ | N |
| 210 | $CH_2CH_3$ | $CO_2CH_3$ | $CH_3$ | $CH_3$ | $CH_3$ | CH |
| 211 | $CH_2CH_3$ | $CO_2CH_3$ | $CH_3$ | $CH_3$ | $OCH_3$ | CH |
| 212 | $CH_2CH_3$ | $CO_2CH_3$ | $CH_3$ | $CH_3$ | $OCH_3$ | N |
| 213 | $CH_2CH_2CH_3$ | $CO_2CH_3$ | $CH_3$ | $CH_3$ | $CH_3$ | CH |
| 214 | $CH_2CH_2CH_3$ | $CO_2CH_3$ | $CH_3$ | $CH_3$ | $OCH_3$ | CH |
| 215 | $CH_2CH_2CH_3$ | $CO_2CH_3$ | $CH_3$ | $CH_3$ | $OCH_3$ | N |
| 216 | $CH(CH_3)_3$ | $CO_2CH_3$ | $CH_3$ | $CH_3$ | $CH_3$ | CH |
| 217 | $CH(CH_3)_2$ | $CO_2CH_3$ | $CH_3$ | $CH_3$ | $OCH_3$ | CH |
| 218 | $CH(CH_3)_2$ | $CO_2CH_3$ | $CH_3$ | $CH_3$ | $OCH_3$ | N |
| 219 |  | $CO_2CH_3$ | $CH_3$ | $CH_3$ | $CH_3$ | CH |
| 220 |  | $CO_2CH_3$ | $CH_3$ | $CH_3$ | $OCH_3$ | CH |
| 221 |  | $CO_2CH_3$ | $CH_3$ | $OCH_3$ | $OCH_3$ | CH |
| 222 |  | $CO_2CH_3$ | $CH_3$ | $CH_3$ | $OCH_3$ | N |

TABLE 1-continued

| Comp. No. | A | B | C | X | Y | Z |
|---|---|---|---|---|---|---|
| 223 | 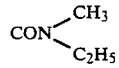 | CO$_2$CH$_3$ | CH$_3$ | OCH$_3$ | OCH$_3$ | N |
| 224 | CH$_3$ | CO$_2$CH$_3$ | H | CH$_3$ | CH$_3$ | CH |
| 225 | CH$_3$ | CO$_2$CH$_3$ | H | CH$_3$ | OCH$_3$ | CH |
| 226 | CH$_3$ | CO$_2$CH$_3$ | H | CH$_3$ | OCH$_3$ | N |
| 227 | CH$_3$ | CO$_2$CH$_3$ | CH$_2$CH$_3$ | CH$_3$ | CH$_3$ | CH |
| 228 | CH$_3$ | CO$_2$CH$_3$ | CH$_2$CH$_3$ | CH$_3$ | OCH$_3$ | CH |
| 229 | CH$_3$ | CO$_2$CH$_3$ | CH$_2$CH$_3$ | CH$_3$ | OCH$_3$ | N |
| 230 | CH$_3$ | CO$_2$CH$_3$ | CH(CH$_3$)$_2$ | CH$_3$ | CH$_3$ | CH |
| 231 | CH$_3$ | CO$_2$CH$_3$ | CH(CH$_3$)$_2$ | CH$_3$ | OCH$_3$ | CH |
| 232 | CH$_3$ | CO$_2$CH$_3$ | CH(CH$_3$)$_2$ | OCH$_3$ | OCH$_3$ | CH |
| 233 | CH$_3$ | CO$_2$CH$_3$ | CH(CH$_3$)$_2$ | CH$_3$ | OCH$_3$ | N |
| 234 | CH$_3$ | CO$_2$CH$_3$ | CH(CH$_3$)$_2$ | OCH$_3$ | OCH$_3$ | N |
| 235 | CH$_3$ | CO$_2$CH$_3$ | C(CH$_3$)$_3$ | CH$_3$ | CH$_3$ | CH |
| 236 | CH$_3$ | CO$_2$CH$_3$ | C(CH$_3$)$_3$ | CH$_3$ | OCH$_3$ | CH |
| 237 | CH$_3$ | CO$_2$CH$_3$ | C(CH$_3$)$_3$ | CH$_3$ | OCH$_3$ | N |
| 238 | CH$_3$ | CON(CH$_3$)$_2$ | CH$_3$ | CH$_3$ | CH$_3$ | CH |
| 239 | CH$_3$ | CON(CH$_3$)$_2$ | CH$_3$ | CH$_3$ | OCH$_3$ | CH |
| 240 | CH$_3$ | CON(CH$_3$)$_2$ | CH$_3$ | OCH$_3$ | OCH$_3$ | CH |
| 241 | CH$_3$ | CON(CH$_3$)$_2$ | CH$_3$ | CH$_3$ | OCH$_3$ | N |
| 242 | CH$_3$ | CON(CH$_3$)$_2$ | CH$_3$ | OCH$_3$ | OCH$_3$ | N |
| 243 | CH$_3$ | CON(C$_2$H$_5$)$_2$ | CH$_3$ | CH$_3$ | CH$_3$ | CH |
| 244 | CH$_3$ | CON(C$_2$H$_5$)$_2$ | CH$_3$ | CH$_3$ | OCH$_3$ | CH |
| 245 | CH$_3$ | CON(C$_2$H$_5$)$_2$ | CH$_3$ | OCH$_3$ | OCH$_3$ | CH |
| 246 | CH$_3$ | CON(C$_2$H$_5$)$_2$ | CH$_3$ | CH$_3$ | OCH$_3$ | N |
| 247 | CH$_3$ | CON(C$_2$H$_5$)$_2$ | CH$_3$ | OCH$_3$ | OCH$_3$ | N |
| 248 | CH$_3$ | 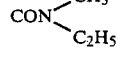 | CH$_3$ | CH$_3$ | CH$_3$ | CH |
| 249 | CH$_3$ | 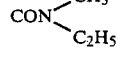 | CH$_3$ | CH$_3$ | OCH$_3$ | CH |
| 250 | CH$_3$ | 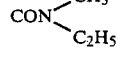 | CH$_3$ | CH$_3$ | OCH$_3$ | N |
| 251 | CH$_3$ | CONHCH$_3$ | CH$_3$ | CH$_3$ | CH$_3$ | CH |
| 252 | CH$_3$ | CONHCH$_3$ | CH$_3$ | CH$_3$ | OCH$_3$ | CH |
| 253 | CH$_3$ | CONHCH$_3$ | CH$_3$ | CH$_3$ | OCH$_3$ | N |
| 254 | CH$_3$ | CONHC$_2$H$_5$ | CH$_3$ | CH$_3$ | CH$_3$ | CH |
| 255 | CH$_3$ | CONHC$_2$H$_5$ | CH$_3$ | CH$_3$ | OCH$_3$ | CH |
| 256 | CH$_3$ | CONHC$_2$H$_5$ | CH$_3$ | CH$_3$ | OCH$_3$ | N |
| 257 | CH$_3$ | 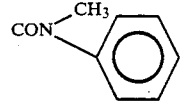 | CH$_3$ | CH$_3$ | CH$_3$ | CH |
| 258 | CH$_3$ | 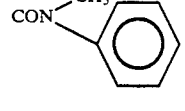 | CH$_3$ | CH$_3$ | OCH$_3$ | CH |
| 259 | CH$_3$ | 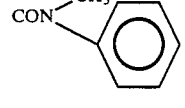 | CH$_3$ | CH$_3$ | OCH$_3$ | N |

TABLE 1-continued
| Comp. No. | A | B | C | X | Y | Z |
|---|---|---|---|---|---|---|
| 260 | CH$_3$ | CO$_2$CH$_3$ |  | CH$_3$ | CH$_3$ | CH |
| 261 | CH$_3$ | CO$_2$CH$_3$ |  | CH$_3$ | OCH$_3$ | CH |
| 262 | CH$_3$ | CO$_2$CH$_3$ |  | OCH$_3$ | OCH$_3$ | CH |
| 263 | CH$_3$ | CO$_2$CH$_3$ |  | CH$_3$ | OCH$_3$ | N |
| 264 | CH$_3$ | CO$_2$CH$_3$ | 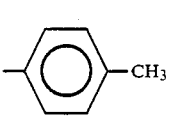 | OCH$_3$ | OCH$_3$ | N |
| 265 | CH$_3$ | CO$_2$CH$_3$ | 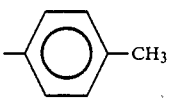 | CH$_3$ | OCH$_3$ | CH |
| 266 | CH$_3$ | CO$_2$CH$_3$ | 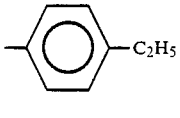 | CH$_3$ | OCH$_3$ | N |
| 267 | CH$_3$ | CO$_2$CH$_3$ | 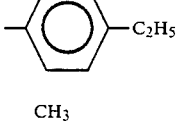 | CH$_3$ | OCH$_3$ | CH |
| 268 | CH$_3$ | CO$_2$CH$_3$ | 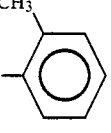 | CH$_3$ | OCH$_3$ | N |
| 269 | CH$_3$ | CO$_2$CH$_3$ | 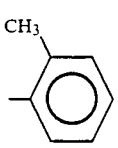 | CH$_3$ | OCH$_3$ | CH |
| 270 | CH$_3$ | CO$_2$CH$_3$ | 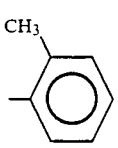 | CH$_3$ | OCH$_3$ | N |

TABLE 1-continued
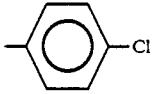
| Comp. No. | A | B | C | X | Y | Z |
|---|---|---|---|---|---|---|
| 271 | CH₃ | CO₂CH₃ | 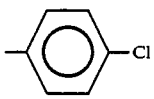 4-Cl-C₆H₄ | CH₃ | CH₃ | CH |
| 272 | CH₃ | CO₂CH₃ | 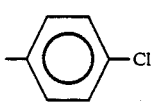 4-Cl-C₆H₄ | CH₃ | OCH₃ | CH |
| 273 | CH₃ | CO₂CH₃ | 4-Cl-C₆H₄ | CH₃ | OCH₃ | N |
| 274 | CH₃ | CO₂CH₃ | 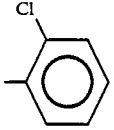 2-Cl-C₆H₄ | CH₃ | CH₃ | CH |
| 275 | CH₃ | CO₂CH₃ | 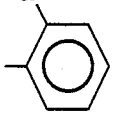 2-Cl-C₆H₄ | CH₃ | OCH₃ | CH |
| 276 | CH₃ | CO₂CH₃ | 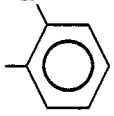 2-Cl-C₆H₄ | CH₃ | OCH₃ | N |
| 277 | CH₃ | CO₂CH₃ | 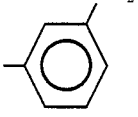 3-NO₂-C₆H₄ | CH₃ | CH₃ | CH |
| 278 | CH₃ | CO₂CH₃ | 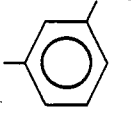 3-NO₂-C₆H₄ | CH₃ | OCH₃ | CH |
| 279 | CH₃ | CO₂CH₃ | 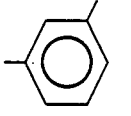 3-NO₂-C₆H₄ | CH₃ | OCH₃ | N |
| 280 | H | CO₂CH₃ |  C₆H₅ | CH₃ | CH₃ | CH |

TABLE 1-continued

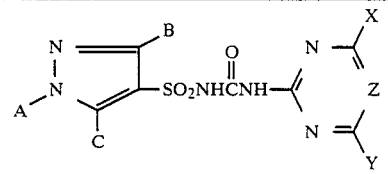

| Comp. No. | A | B | C | X | Y | Z |
|---|---|---|---|---|---|---|
| 281 | H | CO₂CH₃ | ⬡ | CH₃ | OCH₃ | CH |
| 282 | H | CO₂CH₃ | ⬡ | CH₃ | OCH₃ | N |
| 283 | CH₃ | CO₂CH₃ | OCH₃ | CH₃ | CH₃ | CH |
| 284 | CH₃ | CO₂CH₃ | OCH₃ | CH₃ | OCH₃ | CH |
| 285 | CH₃ | CO₂CH₃ | OCH₃ | OCH₃ | OCH₃ | CH |
| 286 | CH₃ | CO₂CH₃ | OCH₃ | CH₃ | OCH₃ | N |
| 287 | CH₃ | CO₂CH₃ | OCH₃ | OCH₃ | OCH₃ | N |
| 288 | CH₃ | CO₂CH₃ | OCH₂CH₃ | CH₃ | CH₃ | CH |
| 289 | CH₃ | CO₂CH₃ | OCH₂CH₃ | CH₃ | OCH₃ | CH |
| 290 | CH₃ | CO₂CH₃ | OCH₂CH₃ | CH₃ | OCH₃ | N |
| 291 | CH₃ | CH₃ | OCH₃ | CH₃ | CH₃ | CH |
| 292 | CH₃ | CH₃ | OCH₃ | CH₃ | OCH₃ | CH |
| 293 | CH₃ | CH₃ | OCH₃ | OCH₃ | OCH₃ | CH |
| 294 | CH₃ | CH₃ | OCH₃ | CH₃ | OCH₃ | N |
| 295 | CH₃ | CH₃ | OCH₃ | OCH₃ | OCH₃ | N |
| 296 | CH₃ | CH₃ | OCH₃ | CH₃ | CH₃ | N |
| 297 | CH₃ | CH₃ | OCH₃ | OCH₃ | N(CH₃)₂ | N |
| 298 | CH₃ | CH₃ | OCH₃ | CH₃ | CF₃ | CH |
| 299 | CH₃ | CH₃ | OCH₃ | OCH₃ | OCH(CH₃)CO₂CH₃ | CH |
| 300 | CH₃ | CH₃ | OCH₃ | OCH₃ | OCH₂CF₃ | N |
| 301 | CH₃ | CH₃ | OCH₂CH₃ | CH₃ | CH₃ | CH |
| 302 | CH₃ | CH₃ | OCH₂CH₃ | CH₃ | OCH₃ | CH |
| 303 | CH₃ | CH₃ | OCH₂CH₃ | CH₃ | OCH₃ | N |
| 304 | CH₃ | CH₃ | H | CH₃ | CH₃ | CH |
| 305 | CH₃ | CH₃ | H | CH₃ | OCH₃ | CH |
| 306 | CH₃ | CH₃ | H | OCH₃ | OCH₃ | CH |
| 307 | CH₃ | CH₃ | H | CH₃ | OCH₃ | N |
| 308 | CH₃ | CH₃ | H | OCH₃ | OCH₃ | N |
| 309 | CH₃ | CH₃ | H | CH₃ | CH₃ | N |
| 310 | CH₃ | CH₂CH₃ | H | CH₃ | CH₃ | CH |
| 311 | CH₃ | CH₂CH₃ | H | CH₃ | OCH₃ | CH |
| 312 | CH₃ | CH₂CH₃ | H | CH₃ | OCH₃ | N |
| 313 | CH₃ | CH(CH₃)₂ | H | CH₃ | CH₃ | CH |
| 314 | CH₃ | CH(CH₃)₂ | H | CH₃ | OCH₃ | CH |
| 315 | CH₃ | CH(CH₃)₂ | H | CH₃ | OCH₃ | N |
| 316 | H | CH₃ | CH₃ | CH₃ | CH₃ | CH |
| 317 | H | CH₃ | CH₃ | CH₃ | OCH₃ | CH |
| 318 | H | CH₃ | CH₃ | OCH₃ | OCH₃ | CH |
| 319 | H | CH₃ | CH₃ | CH₃ | OCH₃ | N |
| 320 | H | CH₃ | CH₃ | OCH₃ | OCH₃ | N |
| 321 | H | CH₂CH₃ | CH₂CH₃ | CH₃ | CH₃ | CH |
| 322 | H | CH₂CH₃ | CH₂CH₃ | CH₃ | OCH₃ | CH |
| 323 | H | CH₂CH₃ | CH₂CH₃ | CH₃ | OCH₃ | N |
| 324 | CH₃ | H | CH₃ | CH₃ | CH₃ | CH |
| 325 | CH₃ | H | CH₃ | CH₃ | OCH₃ | CH |
| 326 | CH₃ | H | CH₃ | OCH₃ | OCH₃ | CH |
| 327 | CH₃ | H | CH₃ | CH₃ | OCH₃ | N |
| 328 | CH₃ | H | CH₃ | OCH₃ | OCH₃ | N |
| 329 | CH₃ | H | CH₃ | CH₃ | CH₃ | N |
| 330 | CH₃ | H | CH₂CH₃ | CH₃ | CH₃ | CH |
| 331 | CH₃ | H | CH₂CH₃ | CH₃ | OCH₃ | CH |
| 332 | CH₃ | H | CH₂CH₃ | CH₃ | OCH₃ | N |
| 333 | CH₃ | H | CH(CH₃)₂ | CH₃ | CH₃ | CH |
| 334 | CH₃ | H | CH(CH₃)₂ | CH₃ | OCH₃ | CH |
| 335 | CH₃ | H | CH(CH₃)₂ | CH₃ | OCH₃ | N |
| 336 | CH₃ | H | C(CH₃)₃ | CH₃ | CH₃ | CH |
| 337 | CH₃ | H | C(CH₃)₃ | CH₃ | OCH₃ | CH |

TABLE 1-continued

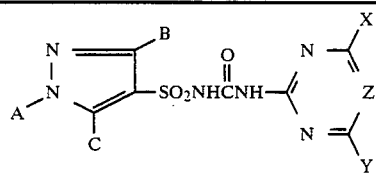

| Comp. No. | A | B | C | X | Y | Z |
|---|---|---|---|---|---|---|
| 338 | $CH_3$ | H | $C(CH_3)_3$ | $CH_3$ | $OCH_3$ | N |
| 339 | H | $CH_2CH_3$ | $OCH_3$ | $CH_3$ | $CH_3$ | CH |
| 340 | H | $CH_2CH_3$ | $OCH_3$ | $CH_3$ | $OCH_3$ | CH |
| 341 | H | $CH_2CH_3$ | $OCH_3$ | $CH_3$ | $OCH_3$ | N |
| 342 | H | $CH(CH_3)_2$ | $OCH_3$ | $CH_3$ | $CH_3$ | CH |
| 343 | H | $CH(CH_3)_2$ | $OCH_3$ | $CH_3$ | $OCH_3$ | CH |
| 344 | H | $CH(CH_3)_2$ | $OCH_3$ | $CH_3$ | $OCH_3$ | N |
| 345 | H | C₆H₅ | $OCH_3$ | $CH_3$ | $CH_3$ | CH |
| 346 | H | C₆H₅ | $OCH_3$ | $CH_3$ | $OCH_3$ | CH |
| 347 | H | C₆H₅ | $OCH_3$ | $CH_3$ | $OCH_3$ | N |
| 348 | $CH_3$ | $CH_2CH_3$ | $OCH_3$ | $CH_3$ | $CH_3$ | CH |
| 349 | $CH_3$ | $CH_2CH_3$ | $OCH_3$ | $CH_3$ | $OCH_3$ | CH |
| 350 | $CH_3$ | $CH_2CH_3$ | $OCH_3$ | $CH_3$ | $OCH_3$ | CH |
| 351 | $CH_3$ | $CH_2CH_3$ | $OCH_3$ | $CH_3$ | $OCH_3$ | N |
| 352 | $CH_3$ | $CH_2CH_3$ | $OCH_3$ | $OCH_3$ | $OCH_3$ | N |
| 353 | $CH_3$ | $CH_2CH_2CH_3$ | $OCH_3$ | $CH_3$ | $CH_3$ | CH |
| 354 | $CH_3$ | $CH_2CH_2CH_3$ | $OCH_3$ | $CH_3$ | $OCH_3$ | CH |
| 355 | $CH_3$ | $CH_2CH_2CH_3$ | $OCH_3$ | $CH_3$ | $OCH_3$ | N |
| 356 | $CH_3$ | $CH(CH_3)_2$ | $OCH_3$ | $CH_3$ | $CH_3$ | CH |
| 357 | $CH_3$ | $CH(CH_3)_2$ | $OCH_3$ | $CH_3$ | $OCH_3$ | CH |
| 358 | $CH_3$ | $CH(CH_3)_2$ | $OCH_3$ | $OCH_3$ | $OCH_3$ | CH |
| 359 | $CH_3$ | $CH(CH_3)_2$ | $OCH_3$ | $CH_3$ | $OCH_3$ | N |
| 360 | $CH_3$ | $CH(CH_3)_2$ | $OCH_3$ | $OCH_3$ | $OCH_3$ | N |
| 361 | $CH_3$ | $CH(CH_3)_2$ | $OCH_3$ | $CH_3$ | Cl | CH |
| 362 | $CH_3$ | $CH(CH_3)_2$ | $OCH_3$ | $OCH_3$ | $CH_2CH_2OCH_3$ | CH |
| 363 | $CH_3$ | $CH(CH_3)_2$ | $OCH_3$ | $CH_3$ | $CH_2OCH_3$ | N |
| 364 | $CH_3$ | $C(CH_3)_3$ | $OCH_3$ | $CH_3$ | $CH_2$ | CH |
| 365 | $CH_3$ | $C(CH_3)_3$ | $OCH_3$ | $CH_3$ | $OCH_2$ | CH |
| 366 | $CH_3$ | $C(CH_3)_3$ | $OCH_3$ | $CH_3$ | $OCH_2$ | N |
| 367 | $CH_3$ | $SCH_3$ | $CH_3$ | $CH_3$ | $CH_3$ | CH |
| 368 | $CH_3$ | $SCH_3$ | $CH_3$ | $CH_3$ | $OCH_3$ | CH |
| 369 | $CH_3$ | $SCH_3$ | $CH_3$ | $CH_3$ | $OCH_3$ | N |
| 370 | $CH_3$ | $S(O)CH_3$ | $CH_3$ | $CH_3$ | $CH_3$ | CH |
| 371 | $CH_3$ | $S(O)CH_3$ | $CH_3$ | $CH_3$ | $OCH_3$ | CH |
| 372 | $CH_3$ | $S(O)CH_3$ | $CH_3$ | $CH_3$ | $OCH_3$ | N |
| 373 | $CH_3$ | $SO_2CH_3$ | $CH_3$ | $CH_3$ | $CH_3$ | CH |
| 374 | $CH_3$ | $SO_2CH_3$ | $CH_3$ | $CH_3$ | $OCH_3$ | CH |
| 375 | $CH_3$ | $SO_2CH_3$ | $CH_3$ | $CH_3$ | $OCH_3$ | N |
| 376 | $CH_3$ | $SO_2CH_2CH_3$ | $CH_3$ | $CH_3$ | $CH_3$ | CH |
| 377 | $CH_3$ | $SO_2CH_2CH_3$ | $CH_3$ | $CH_3$ | $OCH_3$ | CH |
| 378 | $CH_3$ | $SO_2CH_2CH_3$ | $CH_3$ | $CH_3$ | $OCH_3$ | N |
| 379 | $CH_3$ | $SO_2C_3H_7\text{-}n$ | $CH_3$ | $CH_3$ | $CH_3$ | CH |
| 380 | $CH_3$ | $SO_2C_3H_7\text{-}n$ | $CH_3$ | $CH_3$ | $OCH_3$ | CH |
| 381 | $CH_3$ | $SO_2C_3H_7\text{-}n$ | $CH_3$ | $OCH_3$ | $OCH_3$ | CH |
| 382 | $CH_3$ | $SO_2C_3H_7\text{-}n$ | $CH_3$ | $CH_3$ | $OCH_3$ | N |
| 383 | $CH_3$ | $SO_2C_3H_7\text{-}n$ | $CH_3$ | $OCH_3$ | $OCH_3$ | N |
| 384 | $CH_3$ | $CH_3$ | $CO_2CH_3$ | $CH_3$ | $CH_3$ | CH |
| 385 | $CH_3$ | $CH_3$ | $CO_2CH_3$ | $CH_3$ | $OCH_3$ | CH |
| 386 | $CH_3$ | $CH_3$ | $CO_2CH_3$ | $OCH_3$ | $OCH_3$ | CH |
| 387 | $CH_3$ | $CH_3$ | $CO_2CH_3$ | $CH_3$ | $OCH_3$ | N |
| 388 | $CH_3$ | $CH_3$ | $CO_2CH_3$ | $OCH_3$ | $OCH_3$ | N |
| 389 | $CH_3$ | $CH_3$ | $CO_2CH_3$ | $CH_3$ | $CH_3$ | N |
| 390 | $CH_3$ | $CH_3$ | $CO_2CH_3$ | $CH_3$ | Cl | $C(CH_2)_2Cl$ |
| 391 | $CH_3$ | $CH_3$ | $CO_2CH_3$ | $CH_3$ | —$OCH_2CH_2C$— | |
| 392 | $CH_3$ | $CH_3$ | $CO_2CH_3$ | $CH_3$ | Cl | CH |

TABLE 1-continued

| Comp. No. | A | B | C | X | Y | Z |
|---|---|---|---|---|---|---|
| 393 | CH$_3$ | CH$_3$ | CO$_2$CH$_3$ | CH$_3$ | OCH$_2$CH$_3$ | CH |
| 394 | CH$_3$ | CH$_3$ | CO$_2$CH$_3$ | CH$_3$ | H | CH |
| 395 | CH$_3$ | CH$_3$ | CO$_2$CH$_3$ | CH$_3$ | CH$_2$OCH$_3$ | CH |
| 396 | CH$_3$ | CH$_3$ | CO$_2$CH$_3$ | CH$_3$ | CF$_3$ | CH |
| 397 | CH$_3$ | CH$_3$ | CO$_2$CH$_3$ | CH$_3$ | OCH$_2$CF$_3$ | CH |
| 398 | CH$_3$ | CH$_3$ | CO$_2$CH$_3$ | CH$_3$ | OCH$_2$CO$_2$CH$_3$ | CH |
| 399 | CH$_3$ | CH$_3$ | CO$_2$CH$_3$ | Cl | Cl | CH |
| 400 | CH$_3$ | CH$_3$ | CO$_2$CH$_3$ | Br | Br | CH |
| 401 | CH$_3$ | CH$_3$ | CO$_2$CH$_3$ | CH$_3$ | Cl | N |
| 402 | CH$_3$ | CH$_3$ | CO$_2$CH$_3$ | Cl | N(CH$_3$)$_2$ | N |
| 403 | CH$_3$ | CH$_3$ | CO$_2$CH$_3$ | OCH$_3$ | N(CH$_3$)$_2$ | N |
| 404 | CH$_3$ | CH$_3$ | CO$_2$CH$_3$ | CH$_3$ | OCH$_2$CH$_3$ | N |
| 405 | CH$_3$ | CH$_3$ | CO$_2$CH$_3$ | CH$_3$ | NHCH$_2$CH$_3$ | N |
| 406 | CH$_3$ | CH$_3$ | CO$_2$CH$_3$ | CH$_3$ | CH$_2$OCH$_3$ | N |
| 407 | CH$_3$ | CH$_3$ | CO$_2$CH$_3$ | CH$_3$ | OCHCO$_2$H<br>\|<br>CH$_3$ | N |
| 408 | CH$_3$ | CH$_3$ | CO$_2$CH$_2$CH$_3$ | CH$_3$ | CH$_3$ | CH |
| 409 | CH$_3$ | CH$_3$ | CO$_2$CH$_2$CH$_3$ | CH$_3$ | OCH$_3$ | CH |
| 410 | CH$_3$ | CH$_3$ | CO$_2$CH$_2$CH$_3$ | OCH$_3$ | OCH$_3$ | CH |
| 411 | CH$_3$ | CH$_3$ | CO$_2$CH$_2$CH$_3$ | CH$_3$ | OCH$_3$ | N |
| 412 | CH$_3$ | CH$_3$ | CO$_2$CH$_2$CH$_3$ | OCH$_3$ | OCH$_3$ | N |
| 413 | CH$_3$ | CH$_3$ | CO$_2$CH$_2$CH$_3$ | CH$_3$ | Cl | C(CH$_2$)$_2$Cl |
| 414 | CH$_3$ | CH$_3$ | CO$_2$CH$_2$CH$_3$ | CH$_3$ | —OCH$_2$CH$_2$C— | |
| 415 | CH$_3$ | CH$_3$ | CO$_2$C$_3$H$_7$-n | CH$_3$ | CH$_3$ | CH |
| 416 | CH$_3$ | CH$_3$ | CO$_2$C$_3$H$_7$-n | CH$_3$ | OCH$_3$ | CH |
| 417 | CH$_3$ | CH$_3$ | CO$_2$C$_3$H$_7$-n | OCH$_3$ | OCH$_3$ | CH |
| 418 | CH$_3$ | CH$_3$ | CO$_2$C$_3$H$_7$-n | CH$_3$ | OCH$_3$ | N |
| 419 | CH$_3$ | CH$_3$ | CO$_2$C$_3$H$_7$-n | OCH$_3$ | OCH$_3$ | N |
| 420 | CH$_3$ | CH$_3$ | CO$_2$C$_3$H$_7$-n | CH$_3$ | CH$_3$ | CH |
| 421 | CH$_3$ | CH$_3$ | CO$_2$C$_3$H$_7$-n | CH$_3$ | OCH$_3$ | CH |
| 422 | CH$_3$ | CH$_3$ | CO$_2$C$_3$H$_7$-n | OCH$_3$ | OCH$_3$ | CH |
| 423 | CH$_3$ | CH$_3$ | CO$_2$C$_3$H$_7$-n | CH$_3$ | OCH$_3$ | N |
| 424 | CH$_3$ | CH$_3$ | CO$_2$C$_3$H$_7$-n | OCH$_3$ | OCH$_3$ | N |
| 425 | CH$_3$ | CH$_3$ | CO$_2$CH$_2$CH=CH$_2$ | CH$_3$ | CH$_3$ | CH |
| 426 | CH$_3$ | CH$_3$ | CO$_2$CH$_2$CH=CH$_2$ | CH$_3$ | OCH$_3$ | CH |
| 427 | CH$_3$ | CH$_3$ | CO$_2$CH$_2$CH=CH$_2$ | OCH$_3$ | OCH$_3$ | CH |
| 428 | CH$_3$ | CH$_3$ | CO$_2$CH$_2$CH=CH$_2$ | CH$_3$ | OCH$_3$ | N |
| 429 | CH$_3$ | CH$_3$ | CO$_2$CH$_2$CH=CH$_2$ | OCH$_3$ | OCH$_3$ | N |
| 430 | CH$_3$ | CH$_3$ | CO$_2$CH$_2$C≡CH | CH$_3$ | CH$_3$ | CH |
| 431 | CH$_3$ | CH$_3$ | CO$_2$CHC≡CH | CH$_3$ | OCH$_3$ | CH |
| 432 | CH$_3$ | CH$_3$ | CO$_2$CHC≡CH | OCH$_3$ | OCH$_3$ | CH |
| 433 | CH$_3$ | CH$_3$ | CO$_2$CHC≡CH | CH$_3$ | OCH$_3$ | N |
| 434 | CH$_3$ | CH$_3$ | CO$_2$CHC≡CH | OCH$_3$ | OCH$_3$ | N |
| 435 | CH$_3$ | CH$_3$ | CO$_2$H | CH$_3$ | CH$_3$ | CH |
| 436 | CH$_3$ | CH$_3$ | CO$_2$H | CH$_3$ | OCH$_3$ | CH |
| 437 | CH$_3$ | CH$_3$ | CO$_2$H | OCHCH$_3$ | OCH$_3$ | CH |
| 438 | CH$_3$ | CH$_3$ | CO$_2$H | CH$_3$ | OCH$_3$ | N |
| 439 | CH$_3$ | CH$_3$ | CO$_2$H | OCH$_3$ | OCH$_3$ | N |
| 440 | CH$_3$ | CH$_3$ | CO$_2$H | CH$_3$ | CH$_3$ | N |
| 441 | CH$_2$CH$_3$ | CH$_3$ | CO$_2$CH$_3$ | CH$_3$ | CH$_3$ | CH |
| 442 | CH$_2$CH$_3$ | CH$_3$ | CO$_2$CH$_3$ | CH$_3$ | OCH$_3$ | CH |
| 443 | CH$_2$CH$_3$ | CH$_3$ | CO$_2$CH$_3$ | OCH$_3$ | OCH$_3$ | CH |
| 444 | CH$_2$CH$_3$ | CH$_3$ | CO$_2$CH$_3$ | CH$_3$ | OCH$_3$ | N |
| 445 | CH$_2$CH$_3$ | CH$_3$ | CO$_2$CH$_3$ | OCH$_3$ | OCH$_3$ | N |
| 446 | CH$_2$CH$_2$CH$_3$ | CH$_3$ | CO$_2$CH$_3$ | CH$_3$ | CH$_3$ | CH |
| 447 | CH$_2$CH$_2$CH$_3$ | CH$_3$ | CO$_2$CH$_3$ | CH$_3$ | OCH$_3$ | CH |
| 448 | CH$_2$CH$_2$CH$_3$ | CH$_3$ | CO$_2$CH$_3$ | CH$_3$ | OCH$_3$ | N |
| 449 | CH(CH$_3$)$_2$ | CH$_3$ | CO$_2$CH$_3$ | CH$_3$ | CH$_3$ | CH |
| 450 | CH(CH$_3$)$_2$ | CH$_3$ | CO$_2$CH$_3$ | CH$_3$ | OCH$_3$ | CH |
| 451 | CH(CH$_3$)$_2$ | CH$_3$ | CO$_2$CH$_3$ | CH$_3$ | OCH$_3$ | N |
| 452 |  | CH$_3$ | CO$_2$CH$_3$ | CH$_3$ | CH$_3$ | CH |

TABLE 1-continued

| Comp. No. | A | B | C | X | Y | Z |
|---|---|---|---|---|---|---|
| 453 |  | CH₃ | CO₂CH₃ | CH₃ | OCH₃ | CH |
| 454 |  | CH₃ | CO₂CH₃ | OCH₃ | OCH₃ | CH |
| 455 |  | CH₃ | CO₂CH₃ | CH₃ | OCH₃ | N |
| 456 |  | CH₃ | CO₂CH₃ | OCH₃ | OCH₃ | N |
| 457 | CH₃ | H | CO₂CH₃ | CH₃ | CH₃ | CH |
| 458 | CH₃ | H | CO₂CH₃ | CH₃ | OCH₃ | CH |
| 459 | CH₃ | H | CO₂CH₃ | CH₃ | OCH₃ | CH |
| 460 | CH₃ | H | CO₂CH₃ | CH₃ | OCH₃ | N |
| 461 | CH₃ | H | CO₂CH₃ | OCH₃ | OCH₃ | N |
| 462 | CH₃ | CH₂CH₃ | CO₂CH₃ | CH₃ | CH₃ | CH |
| 463 | CH₃ | CH₂CH₃ | CO₂CH₃ | CH₃ | OCH₃ | CH |
| 464 | CH₃ | CH₂CH₃ | CO₂CH₃ | OCH₃ | OCH₃ | CH |
| 465 | CH₃ | CH₂CH₃ | CO₂CH₃ | CH₃ | OCH₃ | N |
| 466 | CH₃ | CH₂CH₃ | CO₂CH₃ | OCH₃ | OCH₃ | N |
| 467 | CH₃ | CH₂CH₂CH₃ | CO₂CH₃ | CH₃ | CH₃ | CH |
| 468 | CH₃ | CH₂CH₂CH₃ | CO₂CH₃ | CH₃ | OCH₃ | CH |
| 469 | CH₃ | CH₂CH₂CH₃ | CO₂CH₃ | OCH₃ | OCH₃ | CH |
| 470 | CH₃ | CH₂CH₂CH₃ | CO₂CH₃ | CH₃ | OCH₃ | N |
| 471 | CH₃ | CH₂CH₂CH₃ | CO₂CH₃ | OCH₃ | OCH₃ | N |
| 472 | CH₃ | CH(CH₃)₂ | CO₂CH₃ | CH₃ | CH₃ | CH |
| 473 | CH₃ | CH(CH₃)₂ | CO₂CH₃ | CH₃ | OCH₃ | CH |
| 474 | CH₃ | CH(CH₃)₂ | CO₂CH₃ | OCH₃ | OCH₃ | CH |
| 475 | CH₃ | CH(CH₃)₂ | CO₂CH₃ | CH₃ | OCH₃ | N |
| 476 | CH₃ | CH(CH₃)₂ | CO₂CH₃ | OCH₃ | OCH₃ | N |
| 477 | CH₃ | C(CH₃)₃ | CO₂CH₃ | CH₃ | CH₃ | CH |
| 478 | CH₃ | C(CH₃)₃ | CO₂CH₃ | CH₃ | OCH₃ | CH |
| 479 | CH₃ | C(CH₃)₃ | CO₂CH₃ | CH₃ | OCH₃ | N |
| 480 | CH₃ | CH₃ | CON(CH₃)₂ | CH₃ | CH₃ | CH |
| 481 | CH₃ | CH₃ | CON(CH₃)₂ | CH₃ | OCH₃ | CH |
| 482 | CH₃ | CH₃ | CON(CH₃)₂ | OCH₃ | OCH₃ | CH |
| 483 | CH₃ | CH₃ | CON(CH₃)₂ | CH₃ | OCH₃ | N |
| 484 | CH₃ | CH₃ | CON(CH₃)₂ | OCH₃ | OCH₃ | N |
| 485 | CH₃ | CH₃ | CON(C₂H₅)₂ | CH₃ | CH₃ | CH |
| 486 | CH₃ | CH₃ | CON(C₂H₅)₂ | CH₃ | OCH₃ | CH |
| 487 | CH₃ | CH₃ | CON(C₂H₅)₂ | OCH₃ | OCH₃ | CH |
| 488 | CH₃ | CH₃ | CON(C₂H₅)₂ | CH₃ | OCH₃ | N |
| 489 | CH₃ | CH₃ | CON(C₂H₅)₂ | OCH₃ | OCH₃ | N |
| 490 | CH₃ | CH₃ | CON(CH₃)(C₂H₅) | CH₃ | CH₃ | CH |
| 491 | CH₃ | CH₃ | CON(CH₃)(C₂H₅) | CH₃ | OCH₃ | CH |
| 492 | CH₃ | CH₃ | CON(CH₃)(C₂H₅) | CH₃ | OCH₃ | N |

TABLE 1-continued

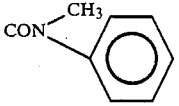

| Comp. No. | A | B | C | X | Y | Z |
|---|---|---|---|---|---|---|
| 493 | $CH_3$ | $CH_3$ | $CONHCH_3$ | $CH_3$ | $CH_3$ | CH |
| 494 | $CH_3$ | $CH_3$ | $CONHCH_3$ | $CH_3$ | $OCH_3$ | CH |
| 495 | $CH_3$ | $CH_3$ | $CONHCH_3$ | $CH_3$ | $OCH_3$ | N |
| 496 | $CH_3$ | $CH_3$ | $CONHC_2H_5$ | $CH_3$ | $CH_3$ | CH |
| 497 | $CH_3$ | $CH_3$ | $CONHC_2H_5$ | $CH_3$ | $OCH_3$ | CH |
| 498 | $CH_3$ | $CH_3$ | $CONHC_2H_5$ | $CH_3$ | $OCH_3$ | N |
| 499 | $CH_3$ | $CH_3$ | 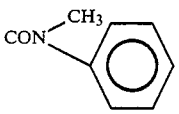 | $CH_3$ | $CH_3$ | CH |
| 500 | $CH_3$ | $CH_3$ | 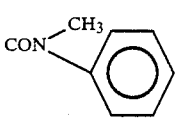 | $CH_3$ | $OCH_3$ | CH |
| 501 | $CH_3$ | $CH_3$ |  | $CH_3$ | $OCH_3$ | N |
| 502 | $CH_3$ |  | $CO_2CH_3$ | $CH_3$ | $CH_3$ | CH |
| 503 | $CH_3$ |  | $CO_2CH_3$ | $CH_3$ | $OCH_3$ | CH |
| 504 | $CH_3$ |  | $CO_2CH_3$ | $OCH_3$ | $OCH_3$ | CH |
| 505 | $CH_3$ |  | $CO_2CH_3$ | $CH_3$ | $OCH_3$ | N |
| 506 | $CH_3$ |  | $CO_2CH_3$ | $OCH_3$ | $OCH_3$ | N |
| 507 | $CH_3$ |  | $CO_2CH_3$ | $CH_3$ | $CH_3$ | N |
| 508 | $CH_3$ | | $CO_2CH_3$ | $CH_3$ | —$OCH_2CH_2C$— | |

TABLE 1-continued

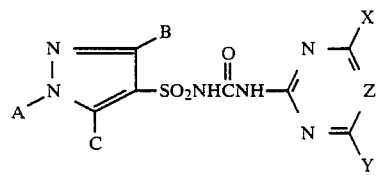

| Comp. No. | A | B | C | X | Y | Z |
|---|---|---|---|---|---|---|
| 509 | CH$_3$ | phenyl | CO$_2$CH$_3$ | CH$_3$ | Cl | C(CH$_2$)$_2$Cl |
| 510 | CH$_3$ | phenyl | CO$_2$CH$_3$ | OCH$_3$ | N(CH$_3$)$_2$ | N |
| 511 | CH$_3$ | 4-CH$_3$-phenyl | CO$_2$CH$_3$ | CH$_3$ | CH$_3$ | CH |
| 512 | CH$_3$ | 4-CH$_3$-phenyl | CO$_2$CH$_3$ | CH$_3$ | OCH$_3$ | CH |
| 513 | CH$_3$ | 4-CH$_3$-phenyl | CO$_2$CH$_3$ | CH$_3$ | OCH$_3$ | N |
| 514 | CH$_3$ | 3-CH$_3$-phenyl | CO$_2$CH$_3$ | CH$_3$ | CH$_3$ | CH |
| 515 | CH$_3$ | 3-CH$_3$-phenyl | CO$_2$CH$_3$ | CH$_3$ | OCH$_3$ | CH |
| 516 | CH$_3$ | 3-CH$_3$-phenyl | CO$_2$CH$_3$ | CH$_3$ | OCH$_3$ | N |
| 517 | CH$_3$ | 2-CH$_3$-phenyl | CO$_2$CH$_3$ | CH$_3$ | CH$_3$ | CH |
| 518 | CH$_3$ | 2-CH$_3$-phenyl | CO$_2$CH$_3$ | CH$_3$ | OCH$_3$ | CH |

TABLE 1-continued

| Comp. No. | A | B | C | X | Y | Z |
|---|---|---|---|---|---|---|
| 519 | CH₃ | 2-methylphenyl | CO₂CH₃ | CH₃ | OCH₃ | N |
| 520 | CH₃ | 4-chlorophenyl | CO₂CH₃ | CH₃ | CH₃ | CH |
| 521 | CH₃ | 4-chlorophenyl | CO₂CH₃ | CH₃ | OCH₃ | CH |
| 522 | CH₃ | 4-chlorophenyl | CO₂CH₃ | CH₃ | OCH₃ | N |
| 523 | CH₃ | 2-chlorophenyl | CO₂CH₃ | CH₃ | CH₃ | CH |
| 524 | CH₃ | 2-chlorophenyl | CO₂CH₃ | CH₃ | OCH₃ | CH |
| 525 | CH₃ | 2-chlorophenyl | CO₂CH₃ | CH₃ | OCH₃ | N |
| 526 | CH₃ | 3-nitrophenyl | CO₂CH₃ | CH₃ | CH₃ | CH |
| 527 | CH₃ | 3-nitrophenyl | CO₂CH₃ | CH₃ | OCH₃ | CH |
| 528 | CH₃ | 3-nitrophenyl | CO₂CH₃ | CH₃ | CH₃ | N |
| 529 | CH₃ | OCH₃ | CO₂CH₃ | CH₃ | CH₃ | CH |
| 530 | CH₃ | OCH₃ | CO₂CH₃ | CH₃ | OCH₃ | CH |

TABLE 1-continued

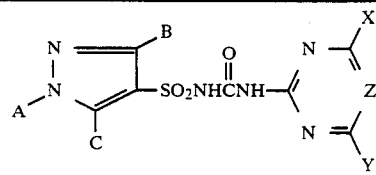

| Comp. No. | A | B | C | X | Y | Z |
|---|---|---|---|---|---|---|
| 531 | $CH_3$ | $OCH_3$ | $CO_2CH_3$ | $OCH_3$ | $OCH_3$ | CH |
| 532 | $CH_3$ | $OCH_3$ | $CO_2CH_3$ | $CH_3$ | $OCH_3$ | N |
| 533 | $CH_3$ | $OCH_3$ | $CO_2CH_3$ | $OCH_3$ | $OCH_3$ | N |
| 534 | $CH_3$ | $OCH_3$ | $CO_2CH_3$ | $CH_3$ | $CH_3$ | N |
| 535 | $CH_3$ | $OCH_2CH_3$ | $CO_2CH_3$ | $CH_3$ | $CH_3$ | CH |
| 536 | $CH_3$ | $OCH_2CH_3$ | $CO_2CH_3$ | $CH_3$ | $OCH_3$ | CH |
| 537 | $CH_3$ | $OCH_2CH_3$ | $CO_2CH_3$ | $CH_3$ | $OCH_3$ | N |
| 538 | $CH_3$ | $CH_3$ | $SCH_3$ | $CH_3$ | $CH_3$ | CH |
| 539 | $CH_3$ | $CH_3$ | $SCH_3$ | $CH_3$ | $OCH_3$ | CH |
| 540 | $CH_3$ | $CH_3$ | $SCH_3$ | $OCH_3$ | $OCH_3$ | CH |
| 541 | $CH_3$ | $CH_3$ | $SCH_3$ | $CH_3$ | $OCH_3$ | N |
| 542 | $CH_3$ | $CH_3$ | $SCH_3$ | $OCH_3$ | $OCH_3$ | N |
| 543 | $CH_3$ | $CH_3$ | $SO_2CH_3$ | $CH_3$ | $CH_3$ | CH |
| 544 | $CH_3$ | $CH_3$ | $SO_2CH_3$ | $CH_3$ | $OCH_3$ | CH |
| 545 | $CH_3$ | $CH_3$ | $SO_2CH_3$ | $OCH_3$ | $OCH_3$ | CH |
| 546 | $CH_3$ | $CH_3$ | $SO_2CH_3$ | $CH_3$ | $OCH_3$ | N |
| 547 | $CH_3$ | $CH_3$ | $SO_2CH_3$ | $OCH_3$ | $OCH_3$ | N |
| 548 | $CH_3$ | $CH_3$ | $SO_2CH_3$ | $CH_3$ | $CH_3$ | N |
| 549 | $CH_3$ | $CH_3$ | $SO_2CH_2CH_3$ | $CH_3$ | $CH_3$ | CH |
| 550 | $CH_3$ | $CH_3$ | $SO_2CH_2CH_3$ | $CH_3$ | $OCH_3$ | CH |
| 551 | $CH_3$ | $CH_3$ | $SO_2CH_2CH_3$ | $OCH_3$ | $OCH_3$ | CH |
| 552 | $CH_3$ | $CH_3$ | $SO_2CH_2CH_3$ | $CH_3$ | $OCH_3$ | N |
| 553 | $CH_3$ | $CH_3$ | $SO_2CH_2CH_3$ | $OCH_3$ | $OCH_3$ | N |
| 554 | $CH_3$ | $CH_3$ | $SC_3H_7$-n | $CH_3$ | $CH_3$ | CH |
| 555 | $CH_3$ | $CH_3$ | $SC_3H_7$-n | $CH_3$ | $OCH_3$ | CH |
| 556 | $CH_3$ | $CH_3$ | $SC_3H_7$-n | $OCH_3$ | $OCH_3$ | CH |
| 557 | $CH_3$ | $CH_3$ | $SC_3H_7$-n | $CH_3$ | $OCH_3$ | N |
| 558 | $CH_3$ | $CH_3$ | $SC_3H_7$-n | $OCH_3$ | $OCH_3$ | N |
| 559 | $CH_3$ | $CH_3$ | $SC_3H_7$-n | $CH_3$ | $CH_3$ | N |
| 560 | $CH_3$ | $CH_3$ | $S(O)C_3H_7$-n | $CH_3$ | $CH_3$ | CH |
| 561 | $CH_3$ | $CH_3$ | $S(O)C_3H_7$-n | $CH_3$ | $OCH_3$ | CH |
| 562 | $CH_3$ | $CH_3$ | $S(O)C_3H_7$-n | $OCH_3$ | $OCH_3$ | CH |
| 563 | $CH_3$ | $CH_3$ | $S(O)C_3H_7$-n | $CH_3$ | $OCH_3$ | N |
| 564 | $CH_3$ | $CH_3$ | $S(O)C_3H_7$-n | $OCH_3$ | $OCH_3$ | N |
| 565 | $CH_3$ | $CH_3$ | $SO_2C_3H_7$-n | $CH_3$ | $CH_3$ | CH |
| 566 | $CH_3$ | $CH_3$ | $SO_2C_3H_7$-n | $CH_3$ | $OCH_3$ | CH |
| 567 | $CH_3$ | $CH_3$ | $SO_2C_3H_7$-n | $OCH_3$ | $OCH_3$ | CH |
| 568 | $CH_3$ | $CH_3$ | $SO_2C_3H_7$-n | $CH_3$ | $OCH_3$ | N |
| 569 | $CH_3$ | $CH_3$ | $SO_2C_3H_7$-n | $OCH_3$ | $OCH_3$ | N |
| 570 | $CH_3$ | $CH_3$ | $SO_2C_3H_7$-n | $CH_3$ | $CH_3$ | N |
| 571 | $CH_3$ | $CH_3$ | $SO_2C_3H_7$-n | $CH_3$ | $CH_3$ | $C(CH_2)_2Cl$ |
| 572 | $CH_3$ | $CH_3$ | $SO_2C_3H_7$-n | $CH_3$ | $-OCH_2CH_2C-$ | |
| 573 | $CH_3$ | $CH_3$ | $SO_2C_3H_7$-n | $CH_3$ | Cl | CH |
| 574 | $CH_3$ | $CH_3$ | $SO_2C_3H_7$-n | $CH_3$ | $OCH_2CH_3$ | CH |
| 575 | $CH_3$ | $CH_3$ | $SO_2C_3H_7$-n | $CH_3$ | H | CH |
| 576 | $CH_3$ | $CH_3$ | $SO_2C_3H_7$-n | H | H | CH |
| 577 | $CH_3$ | $CH_3$ | $SO_2C_3H_7$-n | $CH_3$ | $CH_2OCH_3$ | CH |
| 578 | $CH_3$ | $CH_3$ | $SO_2C_3H_7$-n | $CH_3$ | $OCH_2CO_2CH_3$ | CH |
| 579 | $CH_3$ | $CH_3$ | $SO_2C_3H_7$-n | $CH_3$ | Cl | N |
| 580 | $CH_3$ | $CH_3$ | $SO_2C_3H_7$-n | Cl | $N(CH_3)_2$ | N |
| 581 | $CH_3$ | $CH_3$ | $SO_2C_3H_7$-n | $OCH_3$ | $N(CH_3)_2$ | N |
| 582 | $CH_3$ | $CH_3$ | $SO_2C_3H_7$-n | $CH_3$ | $OCH_2CH_3$ | N |
| 583 | $CH_3$ | $CH_3$ | $SO_2C_3H_7$-n | $CH_3$ | $NHCH_3$ | N |
| 584 | $CH_3$ | $CH_3$ | $SO_2C_3H_7$-n | $CH_3$ | $OCH_2CF_3$ | N |
| 585 | $CH_3$ | $CH_3$ | $SO_2C_3H_7$-n | $CH_3$ | $OCH-CO_2H$<br>$\|$<br>$CH_3$ | N |
| 586 | $CH_3$ | $CH_3$ | $SO_2C_3H_7$-i | $CH_3$ | $CH_3$ | CH |
| 587 | $CH_3$ | $CH_3$ | $SO_2C_3H_7$-i | $CH_3$ | $CH_3$ | CH |
| 588 | $CH_3$ | $CH_3$ | $SO_2C_3H_7$-i | $OCH_3$ | $CH_3$ | CH |
| 589 | $CH_3$ | $CH_3$ | $SO_2C_3H_7$-i | $CH_3$ | $OCH_3$ | N |
| 590 | $CH_3$ | $CH_3$ | $SO_2C_3H_7$-i | $OCH_3$ | $OCH_3$ | N |
| 591 | $CH_3$ | $CH_3$ | $SO_2C_3H_7$-i | $CH_3$ | $CH_3$ | N |
| 592 | $CH_3$ | $CH_3$ | $SO_2C_3H_7$-i | $CH_3$ | $-OCH_2CH_2C-$ | |
| 593 | $CH_3$ | $CH_3$ | $SO_2C_3H_7$-i | $CH_3$ | Cl | $C(CH_2)_2Cl$ |
| 594 | $CH_3$ | $CH_3$ | $SO_2C_3H_7$-i | $OCH_3$ | $N(CH_3)_2$ | N |
| 595 | $CH_3$ | $CH_3$ | $SO_2N(CH_3)_2$ | $CH_3$ | $CH_3$ | CH |
| 596 | $CH_3$ | $CH_3$ | $SO_2N(CH_3)_2$ | $CH_3$ | $OCH_3$ | CH |
| 597 | $CH_3$ | $CH_3$ | $SO_2N(CH_3)_2$ | $OCH_3$ | $OCH_3$ | CH |

TABLE 1-continued

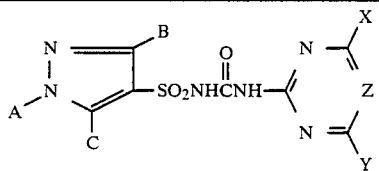

| Comp. No. | A | B | C | X | Y | Z |
|---|---|---|---|---|---|---|
| 598 | CH$_3$ | CH$_3$ | SO$_2$N(CH$_3$)$_2$ | CH$_3$ | OCH$_3$ | N |
| 599 | CH$_3$ | CH$_3$ | SO$_2$N(CH$_3$)$_2$ | OCH$_3$ | OCH$_3$ | N |
| 600 | CH$_3$ | CH$_3$ | SO$_2$N(CH$_3$)$_2$ | CH$_3$ | OCH$_3$ | N |
| 601 | CH$_3$ | CH$_3$ | SO$_2$N(CH$_3$)$_2$ | CH$_3$ | —OCH$_2$CH$_2$C— | |
| 601 | CH$_3$ | CH$_3$ | SO$_2$N(CH$_3$)$_2$ | OCH$_3$ | Cl | C(CH$_2$)$_2$Cl |
| 603 | CH$_3$ | CH$_3$ | SO$_2$N(CH$_3$)$_2$ | OCH$_3$ | N(CH$_3$)$_2$ | N |
| 604 | CH$_3$ | CH$_3$ | SO$_2$N(C$_2$H$_5$)$_2$ | CH$_3$ | CH$_3$ | CH |
| 605 | CH$_3$ | CH$_3$ | SO$_2$N(C$_2$H$_5$)$_2$ | CH$_3$ | OCH$_3$ | CH |
| 606 | CH$_3$ | CH$_3$ | SO$_2$N(C$_2$H$_5$)$_2$ | OCH$_3$ | OCH$_3$ | CH |
| 607 | CH$_3$ | CH$_3$ | SO$_2$N(C$_2$H$_5$)$_2$ | CH$_3$ | OCH$_3$ | N |
| 608 | CH$_3$ | CH$_3$ | SO$_2$N(C$_2$H$_5$)$_2$ | OCH$_3$ | OCH$_3$ | N |
| 609 | CH$_3$ | CH$_3$ | SO$_2$N(C$_2$H$_5$)$_2$ | CH$_3$ | CH$_3$ | N |
| 610 | CH$_3$ | CH$_3$ | SO$_2$N(CH$_3$)(C$_2$H$_5$) | CH$_3$ | CH$_3$ | CH |
| 611 | CH$_3$ | CH$_3$ | SO$_2$N(CH$_3$)(C$_2$H$_5$) | CH$_3$ | OCH$_3$ | CH |
| 612 | CH$_3$ | CH$_3$ | SO$_2$N(CH$_3$)(C$_2$H$_5$) | OCH$_3$ | OCH$_3$ | CH |
| 613 | CH$_3$ | CH$_3$ | SO$_2$N(CH$_3$)(C$_2$H$_5$) | CH$_3$ | OCH$_3$ | N |
| 614 | CH$_3$ | CH$_3$ | SO$_2$N(CH$_3$)(C$_2$H$_5$) | OCH$_3$ | OCH$_3$ | N |
| 615 | CH$_3$ | CH$_3$ | SO$_2$N(CH$_3$)(C$_2$H$_5$) | CH$_3$ | CH$_3$ | N |
| 616 | CH$_3$ | CH$_3$ | SO$_2$NHCH$_3$ | CH$_3$ | CH$_3$ | CH |
| 617 | CH$_3$ | CH$_3$ | SO$_2$NHCH$_3$ | CH$_3$ | OCH$_3$ | CH |
| 618 | CH$_3$ | CH$_3$ | SO$_2$NHCH$_3$ | CH$_3$ | OCH$_3$ | N |
| 619 | CH$_3$ | CH$_3$ | SO$_2$NHC$_2$H$_5$ | CH$_3$ | CH$_3$ | CH |
| 620 | CH$_3$ | CH$_3$ | SO$_2$NHC$_2$H$_5$ | CH$_3$ | OCH$_3$ | CH |
| 621 | CH$_3$ | CH$_3$ | SO$_2$NHC$_2$H$_5$ | CH$_3$ | OCH$_3$ | N |
| 622 | CH$_3$ | CH$_3$ | SO$_2$NHC$_3$H$_7$-n | CH$_3$ | CH$_3$ | CH |
| 623 | CH$_3$ | CH$_3$ | SO$_2$NHC$_3$H$_7$-n | CH$_3$ | OCH$_3$ | CH |
| 624 | CH$_3$ | CH$_3$ | SO$_2$NHC$_3$H$_7$-n | CH$_3$ | OCH$_3$ | N |
| 625 | CH$_3$ | H | SCH$_3$ | CH$_3$ | OCH$_3$ | CH |
| 626 | CH$_3$ | H | SCH$_3$ | CH$_3$ | OCH$_3$ | N |
| 627 | CH$_3$ | H | S(O)CH$_3$ | CH$_3$ | CH$_3$ | CH |
| 628 | CH$_3$ | H | S(O)CH$_3$ | CH$_3$ | OCH$_3$ | CH |
| 629 | CH$_3$ | H | S(O)CH$_3$ | CH$_3$ | OCH$_3$ | N |
| 630 | CH$_3$ | H | SO$_2$CH$_3$ | CH$_3$ | CH$_3$ | CH |
| 631 | CH$_3$ | H | SO$_2$CH$_3$ | CH$_3$ | OCH$_3$ | CH |
| 632 | CH$_3$ | H | SO$_2$CH$_3$ | OCH$_3$ | OCH$_3$ | CH |
| 633 | CH$_3$ | H | SO$_2$CH$_3$ | CH$_3$ | OCH$_3$ | N |
| 634 | CH$_3$ | H | SO$_2$CH$_3$ | OCH$_3$ | OCH$_3$ | N |
| 635 | CH$_3$ | H | SO$_2$C$_2$H$_5$ | CH$_3$ | CH$_3$ | CH |
| 636 | CH$_3$ | H | SO$_2$C$_2$H$_5$ | CH$_3$ | OCH$_3$ | CH |
| 637 | CH$_3$ | H | SO$_2$C$_2$H$_5$ | CH$_3$ | OCH$_3$ | N |
| 638 | CH$_3$ | H | SO$_2$C$_3$H$_7$-n | CH$_3$ | CH$_3$ | CH |
| 639 | CH$_3$ | H | SO$_2$C$_3$H$_7$-n | CH$_3$ | OCH$_3$ | CH |
| 640 | CH$_3$ | H | SO$_2$C$_3$H$_7$-n | OCH$_3$ | OCH$_3$ | CH |
| 641 | CH$_3$ | H | SO$_2$C$_3$H$_7$-n | CH$_3$ | OCH$_3$ | N |
| 642 | CH$_3$ | H | SO$_2$C$_3$H$_7$-n | OCH$_3$ | OCH$_3$ | N |
| 643 | CH$_3$ | H | SO$_2$C$_3$H$_7$-n | CH$_3$ | CH$_3$ | N |
| 644 | CH$_3$ | H | SO$_2$C$_3$H$_7$-n | CH$_3$ | —OCH$_2$CH$_2$C— | |
| 645 | CH$_3$ | H | SO$_2$C$_3$H$_7$-n | CH$_3$ | Cl | C(CH$_2$)$_2$Cl |
| 646 | CH$_3$ | H | SO$_2$C$_3$H$_7$-n | OCH$_3$ | N(CH$_3$)$_2$ | N |
| 647 | CH$_3$ | H | SO$_2$C$_3$H$_7$-i | CH$_3$ | CH$_3$ | CH |
| 648 | CH$_3$ | H | SO$_2$C$_3$H$_7$-i | CH$_3$ | OCH$_3$ | CH |

TABLE 1-continued

[Structure diagram: pyrazole ring with substituents A (on N), B, C, connected via -SO₂NHCNH- (with =O) to a pyrimidine/triazine ring bearing X, Y, Z]

| Comp. No. | A | B | C | X | Y | Z |
|---|---|---|---|---|---|---|
| 649 | CH₃ | H | SO₂C₃H₇-i | OCH₃ | OCH₃ | CH |
| 650 | CH₃ | H | SO₂C₃H₇-i | CH₃ | OCH₃ | N |
| 651 | CH₃ | H | SO₂C₃H₇-i | OCH₃ | OCH₃ | N |
| 652 | CH₃ | H | SO₂C₃H₇-i | CH₃ | CH₃ | N |
| 653 | CH₃ | H | SO₂C₄H₉-n | CH₃ | CH₃ | N |
| 654 | CH₃ | H | SO₂C₄H₉-n | CH₃ | OCH₃ | CH |
| 655 | CH₃ | H | SO₂C₄H₉-n | CH₃ | OCH₃ | N |
| 656 | CH₃ | H | SO₂N(CH₃)₂ | CH₃ | CH₃ | CH |
| 657 | CH₃ | H | SO₂N(CH₃)₂ | CH₃ | OCH₃ | CH |
| 658 | CH₃ | H | SO₂N(CH₃)₂ | OCH₃ | OCH₃ | CH |
| 659 | CH₃ | H | SO₂N(CH₃)₂ | CH₃ | OCH₃ | N |
| 660 | CH₃ | H | SO₂N(CH₃)₂ | OCH₃ | OCH₃ | N |
| 661 | CH₃ | H | SO₂N(CH₃)₂ | CH₃ | CH₃ | N |
| 662 | CH₃ | H | SO₂N(C₂H₅)₂ | CH₃ | CH₃ | CH |
| 663 | CH₃ | H | SO₂N(C₂H₅)₂ | CH₃ | OCH₃ | CH |
| 664 | CH₃ | H | SO₂N(C₂H₅)₂ | OCH₃ | OCH₃ | CH |
| 665 | CH₃ | H | SO₂N(C₂H₅)₂ | CH₃ | OCH₃ | N |
| 666 | CH₃ | H | SO₂N(C₂H₅)₂ | OCH₃ | OCH₃ | N |
| 667 | CH₃ | H | SO₂NHCH₃ | CH₃ | CH₃ | CH |
| 668 | CH₃ | H | SO₂NHCH₃ | CH₃ | OCH₃ | CH |
| 669 | CH₃ | H | SO₂NHCH₃ | CH₃ | OCH₃ | N |
| 670 | CH₃ | H | SO₂NHC₂H₅ | CH₃ | CH₃ | CH |
| 671 | CH₃ | H | SO₂NHC₂H₅ | CH₃ | OCH₃ | CH |
| 672 | CH₃ | H | SO₂NHC₂H₅ | CH₃ | OCH₃ | N |
| 673 | H | CH₃ | SCH₃ | CH₃ | CH₃ | CH |
| 674 | H | CH₃ | SCH₃ | CH₃ | OCH₃ | CH |
| 675 | H | CH₃ | SCH₃ | CH₃ | OCH₃ | N |
| 676 | H | CH₃ | SO₂CH₃ | CH₃ | CH₃ | CH |
| 677 | H | CH₃ | SO₂CH₃ | CH₃ | OCH₃ | CH |
| 678 | H | CH₃ | SO₂CH₃ | CH₃ | OCH₃ | N |
| 679 | H | CH₃ | SO₂C₂H₅ | CH₃ | CH₃ | CH |
| 680 | H | CH₃ | SO₂C₂H₅ | CH₃ | OCH₃ | CH |
| 681 | H | CH₃ | SO₂C₂H₅ | CH₃ | OCH₃ | N |
| 682 | H | CH₃ | SO₂C₃H₇-n | CH₃ | CH₃ | CH |
| 683 | H | CH₃ | SO₂C₃H₇-n | CH₃ | OCH₃ | CH |
| 684 | H | CH₃ | SO₂C₃H₇-n | OCH₃ | OCH₃ | CH |
| 685 | H | CH₃ | SO₂C₃H₇-n | CH₃ | OCH₃ | N |
| 686 | H | CH₃ | SO₂C₃H₇-n | OCH₃ | OCH₃ | N |
| 687 | H | CH₃ | SO₂N(CH₃)₂ | CH₃ | CH₃ | CH |
| 688 | H | CH₃ | SO₂N(CH₃)₂ | CH₃ | OCH₃ | CH |
| 689 | H | CH₃ | SO₂N(CH₃)₂ | CH₃ | OCH₃ | N |
| 690 | H | CH₃ | SO₂N(C₂H₅)₂ | CH₃ | CH₃ | CH |
| 691 | H | CH₃ | SO₂N(C₂H₅)₂ | CH₃ | OCH₃ | CH |
| 692 | H | CH₃ | SO₂N(C₂H₅)₂ | CH₃ | OCH₃ | N |
| 693 | H | H | SO₂CH₃ | CH₃ | CH₃ | CH |
| 694 | H | H | SO₂CH₃ | CH₃ | OCH₃ | CH |
| 695 | H | H | SO₂CH₃ | CH₃ | OCH₃ | N |
| 696 | H | H | SO₂C₃H₇-n | CH₃ | CH₃ | CH |
| 697 | H | H | SO₂C₃H₇-n | CH₃ | OCH₃ | CH |
| 698 | H | H | SO₂C₃H₇-n | CH₃ | OCH₃ | N |
| 699 | H | H | SO₂N(CH₃)₂ | CH₃ | CH₃ | CH |
| 700 | H | H | SO₂N(CH₃)₂ | CH₃ | OCH₃ | CH |
| 701 | H | H | SO₂N(CH₃)₂ | CH₃ | OCH₃ | N |
| 702 | H | H | SO₂N(C₂H₅)₂ | CH₃ | CH₃ | CH |
| 703 | H | H | SO₂N(C₂H₅)₂ | CH₃ | OCH₃ | CH |
| 704 | H | H | SO₂N(C₂H₅)₂ | CH₃ | OCH₃ | N |
| 705 | phenyl | CH₃ | SO₂CH₃ | CH₃ | CH₃ | CH |
| 706 | phenyl | CH₃ | SO₂CH₃ | CH₃ | OCH₃ | CH |

TABLE 1-continued

| Comp. No. | A | B | C | X | Y | Z |
|---|---|---|---|---|---|---|
| 707 | phenyl | $CH_3$ | $SO_2CH_3$ | $CH_3$ | $OCH_3$ | N |
| 708 | phenyl | $CH_3$ | $SO_2C_3H_7$-n | $CH_3$ | $CH_3$ | CH |
| 709 | phenyl | $CH_3$ | $SO_2C_3H_7$-n | $CH_3$ | $OCH_3$ | CH |
| 710 | phenyl | $CH_3$ | $SO_2C_3H_7$-n | $CH_3$ | $OCH_3$ | N |
| 711 | phenyl | $CH_3$ | $SO_2N(CH_3)_2$ | $CH_3$ | $CH_3$ | CH |
| 712 | phenyl | $CH_3$ | $SO_2N(CH_3)_2$ | $CH_3$ | $OCH_3$ | CH |
| 713 | phenyl | $CH_3$ | $SO_2N(CH_3)_2$ | $CH_3$ | $OCH_3$ | N |
| 714 | phenyl | $CH_3$ | $SO_2N(C_2H_5)_2$ | $CH_3$ | $CH_3$ | CH |
| 715 | phenyl | $CH_3$ | $SO_2N(C_2H_5)_2$ | $CH_3$ | $OCH_3$ | CH |
| 716 | phenyl | $CH_3$ | $SO_2N(C_2H_5)_2$ | $CH_3$ | $OCH_3$ | N |
| 717 | $CH_3$ | H | H | $CH_3$ | $CH_3$ | CH |
| 718 | $CH_3$ | H | H | $CH_3$ | $OCH_3$ | CH |
| 719 | $CH_3$ | H | H | $OCH_3$ | $OCH_3$ | CH |
| 720 | $CH_3$ | H | H | $CH_3$ | $OCH_3$ | N |
| 721 | $CH_3$ | H | H | $OCH_3$ | $OCH_3$ | N |
| 722 | H | H | H | $CH_3$ | $CH_3$ | CH |
| 723 | H | H | H | $CH_3$ | $OCH_3$ | CH |
| 724 | H | H | H | $OCH_3$ | $OCH_3$ | CH |
| 725 | H | H | H | $CH_3$ | $OCH_3$ | N |
| 726 | H | H | H | $OCH_3$ | $OCH_3$ | N |
| 727 | $CH_2CH_3$ | $CO_2CH_3$ | $CH_3$ | $OCH_3$ | $OCH_3$ | CH |

TABLE 1-continued

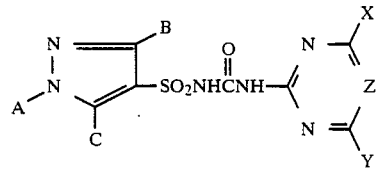

| Comp. No. | A | B | C | X | Y | Z |
|---|---|---|---|---|---|---|
| 728 | $CH_2CH_3$ | $CO_2CH_3$ | $CH_3$ | $OCH_3$ | $OCH_3$ | N |
| 729 | $CH_3$ | $CO_2CH_2CH_3$ | ⌬ | $CH_3$ | $CH_3$ | CH |
| 730 | $CH_3$ | $CO_2CH_2CH_3$ | ⌬ | $CH_3$ | $OCH_3$ | CH |
| 731 | $CH_3$ | $CO_2CH_2CH_3$ | ⌬ | $OCH_3$ | $OCH_3$ | CH |
| 732 | $CH_3$ | $CO_2CH_2CH_3$ | ⌬ | $CH_3$ | $OCH_3$ | N |
| 733 | $CH_3$ | $CO_2CH_2CH_3$ | ⌬ | $OCH_3$ | $OCH_3$ | N |
| 734 | $CH_3$ | $CH_3$ | $CO_2C_3H_7$-i | $CH_3$ | $CH_3$ | CH |
| 735 | $CH_3$ | $CH_3$ | $CO_2C_3H_7$-i | $CH_3$ | $OCH_3$ | CH |
| 736 | $CH_3$ | $CH_3$ | $CO_2C_3H_7$-i | $OCH_3$ | $OCH_3$ | CH |
| 737 | $CH_3$ | $CH_3$ | $CO_2C_3H_7$-i | $CH_3$ | $OCH_3$ | N |
| 738 | $CH_3$ | $CH_3$ | $CO_2C_3H_7$-i | $OCH_3$ | $OCH_3$ | N |
| 739 | $CH_3$ | H | H | $CH_3$ | $-OCH_2CH_2C-$ | |
| 740 | $CH_3$ | H | H | $CH_3$ | Cl | $C(CH_2)_2Cl$ |
| 741 | $CH_3$ | H | H | $CH_3$ | $CH_3$ | N |
| 742 | $CH_3$ | $CH_3$ | $SC_2H_5$ | $CH_3$ | $CH_3$ | CH |
| 743 | $CH_3$ | $CH_3$ | $SC_2H_5$ | $CH_3$ | $OCH_3$ | CH |
| 744 | $CH_3$ | $CH_3$ | $SC_2H_5$ | $OCH_3$ | $OCH_3$ | CH |
| 745 | $CH_3$ | $CH_3$ | $SC_2H_5$ | $CH_3$ | $OCH_3$ | N |
| 746 | $CH_3$ | $CH_3$ | $SC_2H_5$ | $OCH_3$ | $OCH_3$ | N |
| 747 | $CH_3$ | $CH_3$ | S-⌬ | $CH_3$ | $CH_3$ | CH |
| 748 | $CH_3$ | $CH_3$ | S-⌬ | $CH_3$ | $OCH_3$ | CH |
| 749 | $CH_3$ | $CH_3$ | S-⌬ | $CH_3$ | $OCH_3$ | N |
| 750 | $CH_3$ | $CH_3$ | $SCH_2$-⌬ | $CH_3$ | $CH_3$ | CH |

TABLE 1-continued

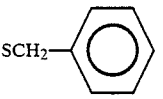

| Comp. No. | A | B | C | X | Y | Z |
|---|---|---|---|---|---|---|
| 751 | CH$_3$ | CH$_3$ | SCH$_2$—phenyl | CH$_3$ | OCH$_3$ | CH |
| 752 | CH$_3$ | CH$_3$ | SCH$_2$—phenyl | OCH$_3$ | OCH$_3$ | CH |
| 753 | CH$_3$ | CH$_3$ | SCH$_2$—phenyl | CH$_3$ | OCH$_3$ | N |
| 754 | CH$_3$ | CH$_3$ | SCH$_2$—phenyl | OCH$_3$ | OCH$_3$ | N |
| 755 | CH$_3$ | CON-pyrrolidinyl | CH$_3$ | CH$_3$ | OCH$_3$ | CH |
| 756 | CH$_3$ | CON-pyrrolidinyl | CH$_3$ | CH$_3$ | OCH$_3$ | N |
| 757 | CH$_3$ | CON-piperidinyl | CH$_3$ | CH$_3$ | OCH$_3$ | CH |
| 758 | CH$_3$ | CON-piperidinyl | CH$_3$ | CH$_3$ | OCH$_3$ | N |
| 759 | CH$_3$ | CON-hexamethyleneimino | CH$_3$ | CH$_3$ | OCH$_3$ | CH |
| 760 | CH$_3$ | CON-hexamethyleneimino | CH$_3$ | CH$_3$ | OCH$_3$ | N |
| 761 | CH$_3$ | CON-(N'-methylpiperazinyl) | CH$_3$ | CH$_3$ | OCH$_3$ | CH |
| 762 | CH$_3$ | CH$_3$ | CON-pyrrolidinyl | CH$_3$ | CH$_3$ | CH |

TABLE 1-continued

| Comp. No. | A | B | C | X | Y | Z |
|---|---|---|---|---|---|---|
| 763 | CH₃ | CH₃ | CON(pyrrolidine) | CH₃ | OCH₃ | CH |
| 764 | CH₃ | CH₃ | CON(pyrrolidine) | OCH₃ | OCH₃ | CH |
| 765 | CH₃ | CH₃ | CON(pyrrolidine) | CH₃ | OCH₃ | N |
| 766 | CH₃ | CH₃ | CON(pyrrolidine) | OCH₃ | OCH₃ | N |
| 767 | CH₃ | CH₃ | CON(pyrrolidine) | CH₃ | CH₃ | N |
| 768 | CH₃ | CH₃ | CON(pyrrolidine) | Cl | Cl | N |
| 769 | CH₃ | CH₃ | CON(piperidine) | CH₃ | OCH₃ | CH |
| 770 | CH₃ | CH₃ | CON(piperidine) | CH₃ | OCH₃ | N |
| 771 | CH₃ | CH₃ | CON(hexamethyleneimine) | CH₃ | OCH₃ | CH |
| 772 | CH₃ | CH₃ | CON(hexamethyleneimine) | CH₃ | OCH₃ | N |
| 773 | CH₃ | CH₃ | CON(N-methylpiperazine) | CH₃ | OCH₃ | CH |

TABLE 1-continued

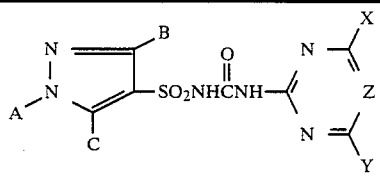

| Comp. No. | A | B | C | X | Y | Z |
|---|---|---|---|---|---|---|
| 774 | CH$_3$ | CH$_3$ | CON⟨ ⟩NCH$_3$ | CH$_3$ | OCH$_3$ | N |

TABLE 2

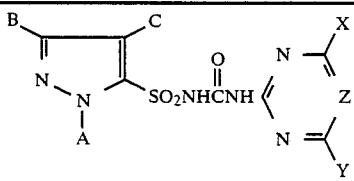

| Comp. | A | B | C | X | Y | Z |
|---|---|---|---|---|---|---|
| 775 | CH$_3$ | CH$_3$ | H | CH$_3$ | CH$_3$ | CH |
| 776 | CH$_3$ | CH$_3$ | H | CH$_3$ | OCH$_3$ | CH |
| 777 | CH$_3$ | CH$_3$ | H | OCH$_3$ | OCH$_3$ | CH |
| 778 | CH$_3$ | CH$_3$ | H | CH$_3$ | OCH$_3$ | N |
| 779 | CH$_3$ | CH$_3$ | H | OCH$_3$ | OCH$_3$ | N |
| 780 | CH$_3$ | CH$_3$ | CH$_3$ | CH$_3$ | CH$_3$ | CH |
| 781 | CH$_3$ | CH$_3$ | CH$_3$ | CH$_3$ | OCH$_3$ | CH |
| 782 | CH$_3$ | CH$_3$ | CH$_3$ | CH$_3$ | OCH$_3$ | N |
| 783 | C$_6$H$_5$ | CH$_3$ | H | CH$_3$ | OCH$_3$ | CH |
| 784 | C$_6$H$_5$ | CH$_3$ | H | CH$_3$ | OCH$_3$ | N |
| 785 | C$_6$H$_5$ | H | H | CH$_3$ | OCH$_3$ | CH |
| 786 | C$_6$H$_5$ | H | H | CH$_3$ | OCH$_3$ | N |
| 787 | CH$_3$ | CH$_3$ | C$_6$H$_5$ | CH$_3$ | OCH$_3$ | CH |
| 788 | CH$_3$ | CH$_3$ | C$_6$H$_5$ | CH$_3$ | OCH$_3$ | N |
| 789 | CH$_3$ | CH$_3$ | Cl | CH$_3$ | CH$_3$ | CH |
| 790 | CH$_3$ | CH$_3$ | Cl | CH$_3$ | OCH$_3$ | CH |
| 791 | CH$_3$ | CH$_3$ | Cl | OCH$_3$ | OCH$_3$ | CH |
| 792 | CH$_3$ | CH$_3$ | Cl | CH$_3$ | OCH$_3$ | N |
| 793 | CH$_3$ | CH$_3$ | Cl | OCH$_3$ | OCH$_3$ | N |
| 794 | CH$_3$ | H | Cl | CH$_3$ | CH$_3$ | CH |

TABLE 2-continued

| Comp. | A | B | C | X | Y | Z |
|---|---|---|---|---|---|---|
| 795 | CH₃ | H | Cl | CH₃ | OCH₃ | CH |
| 796 | CH₃ | H | Cl | OCH₃ | OCH₃ | CH |
| 797 | CH₃ | H | Cl | CH₃ | OCH₃ | N |
| 798 | CH₃ | H | Cl | OCH₃ | OCH₃ | N |
| 799 | CH₃ | CH₃ | NO₂ | CH₃ | CH₃ | CH |
| 800 | CH₃ | CH₃ | NO₂ | CH₃ | OCH₃ | CH |
| 801 | CH₃ | CH₃ | NO₂ | OCH₃ | OCH₃ | CH |
| 802 | CH₃ | CH₃ | NO₂ | CH₃ | OCH₃ | N |
| 803 | CH₃ | CH₃ | NO₂ | OCH₃ | OCH₃ | N |
| 804 | CH₃ | H | NO₂ | CH₃ | OCH₃ | CH |
| 805 | CH₃ | H | NO₂ | OCH₃ | OCH₃ | CH |
| 806 | CH₃ | H | NO₂ | CH₃ | OCH₃ | N |
| 807 | CH₃ | CH₃ | Br | CH₃ | OCH₃ | CH |
| 808 | CH₃ | CH₃ | Br | CH₃ | OCH₃ | N |
| 809 | CH₃ | CH₃ | Br | OCH₃ | OCH₃ | N |
| 810 | CH₃ | CH₃ | CO₂CH₃ | CH₃ | CH₃ | CH |
| 811 | CH₃ | CH₃ | CO₂CH₃ | CH₃ | OCH₃ | CH |
| 812 | CH₃ | CH₃ | CO₂CH₃ | OCH₃ | OCH₃ | CH |
| 813 | CH₃ | CH₃ | CO₂CH₃ | CH₃ | OCH₃ | N |
| 814 | CH₃ | CH₃ | CO₂CH₃ | OCH₃ | OCH₃ | N |
| 815 | CH₃ | H | CO₂CH₃ | CH₃ | CH₃ | CH |
| 816 | CH₃ | H | CO₂CH₃ | CH₃ | OCH₃ | CH |
| 817 | CH₃ | H | CO₂CH₃ | OCH₃ | OCH₃ | CH |
| 818 | CH₃ | H | CO₂CH₃ | CH₃ | OCH₃ | N |
| 819 | CH₃ | H | CO₂CH₃ | OCH₃ | OCH₃ | N |
| 820 | CH₃ | H | CO₂CH₃ | CH₃ | CH₃ | N |
| 821 | CH₃ | H | CO₂CH₃ | CH₃ | Cl | C(CH₂)₂Cl |
| 822 | CH₃ | H | CO₂CH₃ | CH₃ | Cl | CH |
| 823 | CH₃ | H | CO₂CH₃ | CH₃ | OC₂H₅ | CH |
| 824 | CH₃ | H | CO₂CH₃ | CH₃ | OCH₂CO₂CH₃ | CH |
| 825 | CH₃ | H | CO₂CH₃ | CH₃ | Cl | N |
| 826 | CH₃ | H | CO₂CH₃ | OCH₃ | N(CH₃)₂ | N |
| 827 | CH₃ | H | CO₂CH₃ | CH | OCHCO₂H<br>\|<br>CH₃ | N |
| 828 | CH₃ | CH₃ | CO₂C₂H₅ | CH₃ | CH₃ | CH |
| 829 | CH₃ | CH₃ | CO₂C₂H₅ | CH₃ | OCH₃ | CH |
| 830 | CH₃ | CH₃ | CO₂C₂H₅ | OCH₃ | OCH₃ | CH |
| 831 | CH₃ | CH₃ | CO₂C₂H₅ | CH₃ | OCH₃ | N |
| 832 | CH₃ | CH₃ | CO₂C₂H₅ | OCH₃ | OCH₃ | N |
| 833 | CH₃ | H | CO₂C₂H₅ | CH₃ | CH₃ | CH |
| 834 | CH₃ | H | CO₂C₂H₅ | CH₃ | OCH₃ | CH |
| 835 | CH₃ | CH₃ | CO₂C₂H₅ | OCH₃ | OCH₃ | CH |
| 836 | CH₃ | H | CO₂C₂H₅ | CH₃ | OCH₃ | N |
| 837 | CH₃ | H | CO₂C₂H₅ | OCH₃ | OCH₃ | N |
| 838 | H | CH₃ | CO₂CH₃ | CH₃ | CH₃ | CH |
| 839 | H | CH₃ | CO₂CH₃ | CH₃ | OCH₃ | CH |
| 840 | H | CH₃ | CO₂CH₃ | CH₃ | OCH₃ | N |
| 841 | H | H | CO₂CH₃ | CH₃ | OCH₃ | CH |
| 842 | H | H | CO₂CH₃ | OCH₃ | OCH₃ | CH |
| 843 | H | H | CO₂CH₃ | CH₃ | OCH₃ | N |
| 844 | H | CH₃ | CO₂C₂H₅ | CH₃ | CH₃ | CH |
| 845 | H | CH₃ | CO₂C₂H₅ | CH₃ | OCH₃ | CH |
| 846 | H | CH₃ | CO₂C₂H₅ | CH₃ | OCH₃ | N |
| 847 | H | H | CO₂C₂H₅ | CH₃ | CH₃ | CH |
| 848 | H | H | CO₂C₂H₅ | CH₃ | OCH₃ | CH |
| 849 | H | H | CO₂C₂H₅ | OCH₃ | OCH₃ | CH |
| 850 | H | H | CO₂C₂H₅ | CH₃ | OCH₃ | N |
| 851 | H | H | CO₂C₂H₅ | OCH₃ | OCH₃ | N |
| 852 |  | H | CO₂CH₃ | CH₃ | OCH₃ | CH |

TABLE 2-continued

| Comp. | A | B | C | X | Y | Z |
|---|---|---|---|---|---|---|
| 853 | ⌬ (phenyl) | H | CO$_2$CH$_3$ | CH$_3$ | OCH$_3$ | N |
| 854 | CH$_2$ | H | CO$_2$C$_3$H$_7$-n | CH$_3$ | OCH$_3$ | CH |
| 855 | CH$_3$ | H | CO$_2$C$_3$H$_7$-n | OCH$_3$ | OCH$_3$ | CH |
| 856 | CH$_3$ | H | CO$_2$C$_3$H$_7$-n | CH$_3$ | OCH$_3$ | N |
| 857 | CH$_3$ | H | CO$_2$C$_3$H$_7$-n | CH$_3$ | OCH$_3$ | CH |
| 858 | CH$_3$ | H | CO$_2$C$_3$H$_7$-n | OCH$_3$ | OCH$_3$ | CH |
| 859 | CH$_3$ | H | CO$_2$C$_3$H$_7$-n | CH$_3$ | OCH$_3$ | N |
| 860 | CH$_3$ | H | CO$_2$CH$_2$CH=CH$_2$ | CH$_3$ | CH$_3$ | CH |
| 861 | CH$_3$ | H | CO$_2$CH$_2$CH=CH$_2$ | CH$_3$ | OCH$_3$ | CH |
| 862 | CH$_3$ | H | CO$_2$CH$_2$CH=CH$_2$ | CH$_3$ | OCH$_3$ | N |
| 863 | CH$_3$ | H | CO$_2$CH$_2$C≡CH$_2$ | CH$_3$ | CH$_3$ | CH |
| 864 | CH$_3$ | H | CO$_2$CH$_2$C≡CH$_2$ | CH$_3$ | OCH$_3$ | CH |
| 865 | CH$_3$ | H | CO$_2$C$_4$H$_9$-n | CH$_3$ | OCH$_3$ | CH |
| 866 | CH$_3$ | H | CO$_2$C$_4$H$_9$-n | CH$_3$ | OCH$_3$ | N |
| 867 | C$_2$H$_5$ | H | CO$_2$CH$_3$ | CH$_3$ | CH$_3$ | CH |
| 868 | C$_2$H$_5$ | H | CO$_2$CH$_3$ | CH$_3$ | OCH$_3$ | CH |
| 869 | C$_2$H$_5$ | H | CO$_2$CH$_3$ | CH$_3$ | OCH$_3$ | N |
| 870 | CH$_3$ | H | CO$_2$H | CH$_3$ | CH$_3$ | CH |
| 871 | CH$_3$ | H | CO$_2$H | CH$_3$ | OCH$_3$ | CH |
| 872 | CH$_3$ | H | CO$_2$H | CH$_3$ | OCH$_3$ | N |
| 873 | CH$_3$ | C$_2$H$_5$ | CO$_2$CH$_3$ | CH$_3$ | OCH$_3$ | CH |
| 874 | CH$_3$ | C$_2$H$_5$ | CO$_2$CH$_3$ | CH$_3$ | OCH$_3$ | N |
| 875 | CH$_3$ | CH$_3$ | CON(CH$_3$)$_2$ | CH$_3$ | CH$_3$ | CH |
| 876 | CH$_3$ | CH$_3$ | CON(CH$_3$)$_2$ | CH$_3$ | OCH$_3$ | CH |
| 877 | CH$_3$ | CH$_3$ | CON(CH$_3$)$_2$ | CH$_3$ | OCH$_3$ | N |
| 878 | CH$_3$ | CH$_3$ | CON(CH$_3$)$_2$ | OCH$_3$ | OCH$_3$ | N |
| 879 | CH$_3$ | CH$_3$ | SO$_2$N(CH$_3$)$_2$ | CH$_3$ | CH$_3$ | CH |
| 880 | CH$_3$ | CH$_3$ | SO$_2$N(CH$_3$)$_2$ | CH$_3$ | OCH$_3$ | CH |
| 881 | CH$_3$ | CH$_3$ | SO$_2$N(CH$_3$)$_2$ | OCH$_3$ | OCH$_3$ | CH |
| 882 | CH$_3$ | CH$_3$ | SO$_2$N(CH$_3$)$_2$ | CH$_3$ | OCH$_3$ | N |
| 883 | CH$_3$ | CH$_3$ | SO$_2$N(CH$_3$)$_2$ | OCH$_3$ | OCH$_3$ | N |
| 884 | CH$_3$ | CH$_3$ | SO$_2$N(CH$_3$)$_2$ | CH$_3$ | CH$_3$ | N |
| 885 | CH$_3$ | H | SO$_2$N(CH$_3$)$_2$ | CH$_3$ | CH$_3$ | CH |
| 886 | CH$_3$ | H | SO$_2$N(CH$_3$)$_2$ | CH$_3$ | OCH$_3$ | CH |
| 887 | CH$_3$ | H | SO$_2$N(CH$_3$)$_2$ | CH$_3$ | OCH$_3$ | N |
| 888 | CH$_3$ | CH$_3$ | SO$_2$N(C$_2$H$_5$)$_2$ | CH$_3$ | OCH$_3$ | CH |
| 889 | CH$_3$ | CH$_3$ | SO$_2$N(C$_2$H$_5$)$_2$ | CH$_3$ | OCH$_3$ | N |
| 890 | CH$_3$ | CH$_3$ | 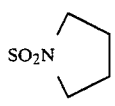 SO$_2$N(pyrrolidinyl) | CH$_3$ | OCH$_3$ | CH |
| 891 | CH$_3$ | CH$_3$ | 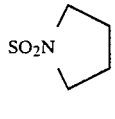 SO$_2$N(pyrrolidinyl) | CH$_3$ | OCH$_3$ | N |
| 892 | CH$_3$ | CH$_3$ | 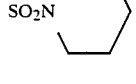 SO$_2$N(piperidinyl) | CH$_3$ | OCH$_3$ | CH |
| 893 | CH$_3$ | CH$_3$ | 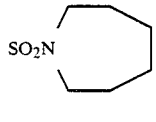 SO$_2$N(hexamethyleneimino) | CH$_3$ | OCH$_3$ | N |
| 894 | CH$_3$ | CH$_3$ | 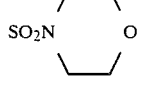 SO$_2$N(morpholino) | CH$_3$ | OCH$_3$ | CH |

TABLE 2-continued
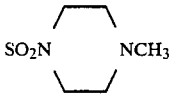
| Comp. | A | B | C | X | Y | Z |
|---|---|---|---|---|---|---|
| 895 | $CH_3$ | $CH_3$ |  | $CH_3$ | $OCH_3$ | CH |
| 896 | H | $CH_3$ | H | $CH_3$ | $CH_3$ | CH |
| 897 | H | $CH_3$ | H | $CH_3$ | $OCH_3$ | CH |
| 898 | H | $CH_3$ | H | $CH_3$ | $OCH_3$ | N |
| 899 | $CH_3$ |  | H | $CH_3$ | $OCH_3$ | CH |
| 900 | $CH_3$ |  | H | $OCH_3$ | $OCH_3$ | CH |
| 901 | $CH_3$ |  | H | $CH_3$ | $OCH_3$ | N |
| 902 | $CH_3$ | H |  | $CH_3$ | $OCH_3$ | CH |
| 903 | $CH_3$ | H |  | $OCH_3$ | $OCH_3$ | CH |
| 904 | $CH_3$ | H | 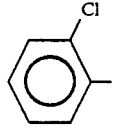 | $CH_3$ | $OCH_3$ | N |
| 905 | 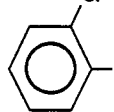 | H | Cl | $CH_3$ | $OCH_3$ | CH |
| 906 | 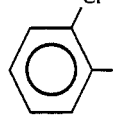 | H | Cl | $OCH_3$ | $OCH_3$ | CH |
| 907 |  | H | Cl | $CH_3$ | $OCH_3$ | N |

TABLE 2-continued

| Comp. | A | B | C | X | Y | Z |
|---|---|---|---|---|---|---|
| 908 | 2-Cl-C6H4 | H | CO2CH3 | CH3 | OCH3 | CH |
| 909 | 2-Cl-C6H4 | H | CO2CH3 | CH3 | OCH3 | N |
| 910 | 2-CH3-C6H4 | H | CO2C2H5 | CH3 | OCH3 | CH |
| 911 | 2-CH3-C6H4 | H | CO2C2H5 | CH3 | OCH3 | N |
| 912 | 4-CH3-C6H4 | CH3 | CO2CH3 | CH3 | OCH3 | CH |
| 913 | 4-CH3-C6H4 | CH3 | CO2CH3 | OCH3 | OCH3 | CH |
| 914 | 4-CH3-C6H4 | CH3 | CO2CH3 | CH3 | OCH3 | N |
| 915 | 3-NO2-C6H4 | H | CO2CH3 | CH3 | OCH3 | CH |
| 916 | 3-NO2-C6H4 | H | CO2CH3 | CH3 | OCH3 | N |
| 917 | 4-NO2-C6H4 | CH3 | CO2CH3 | CH3 | OCH3 | CH |

TABLE 2-continued

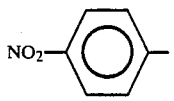

| Comp. | A | B | C | X | Y | Z |
|---|---|---|---|---|---|---|
| 918 | 4-NO$_2$-C$_6$H$_4$- | CH$_3$ | CO$_2$CH$_3$ | CH$_3$ | OCH$_3$ | N |
| 919 | 3-CH$_3$-C$_6$H$_4$- | H | NO$_2$ | CH$_3$ | OCH$_3$ | CH |
| 920 | 3-CH$_3$-C$_6$H$_4$- | H | NO$_2$ | CH$_3$ | OCH$_3$ | N |
| 921 | C$_6$H$_5$- | H | CO$_2$H | CH$_3$ | OCH$_3$ | CH |
| 922 | C$_6$H$_5$- | H | CO$_2$H | CH$_3$ | OCH$_3$ | N |
| 923 | C$_6$H$_5$- | H | NO$_2$ | CH$_3$ | OCH$_3$ | CH |
| 924 | C$_6$H$_5$- | H | NO$_2$ | CH$_3$ | OCH$_3$ | N |
| 925 | CH$_3$ | CH$_3$ | Cl | CH$_3$ | H | CH |
| 926 | CH$_3$ | CH$_3$ | Cl | CH$_3$ | Cl | CH |
| 927 | CH$_3$ | CH$_3$ | Cl | CH$_3$ | —OCH$_2$CH$_2$C— | |
| 928 | CH$_3$ | CH$_3$ | Cl | CH$_3$ | CH$_3$ | N |
| 929 | CH$_3$ | CH$_3$ | NO$_2$ | CH$_3$ | Cl | CH |
| 930 | CH$_3$ | CH$_3$ | NO$_2$ | CH$_3$ | —OCH$_2$CH$_2$C— | |
| 931 | CH$_3$ | CH$_3$ | NO$_2$ | CH$_3$ | CH$_3$ | N |
| 932 | CH$_3$ | CH$_3$ | SO$_2$N(CH$_3$)$_2$ | CH$_3$ | Cl | CH |
| 933 | CH$_3$ | CH$_3$ | SO$_2$N(CH$_3$)$_2$ | CH$_3$ | —OCH$_2$CH$_2$C— | |
| 934 | CH$_3$ | CH$_3$ | SO$_2$N(CH$_3$)$_2$ | Cl | N(CH$_3$)$_2$ | N |

TABLE 3

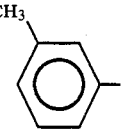

| Comp. No. | A | B | C | X | Y | Z |
|---|---|---|---|---|---|---|
| 935 | CH$_3$ | H | H | CH$_3$ | CH$_3$ | CH |
| 936 | CH$_3$ | H | H | CH$_3$ | OCH$_3$ | CH |
| 937 | CH$_3$ | H | H | OCH$_3$ | OCH$_3$ | CH |

TABLE 3-continued

Structure: A-N=N ring with C, B substituents, connected via SO₂NHCNH (with C=O) to a pyrimidine/triazine ring with X, Y, Z substituents.

| Comp. No. | A | B | C | X | Y | Z |
|---|---|---|---|---|---|---|
| 938 | CH₃ | H | H | CH₃ | OCH₃ | N |
| 939 | CH₃ | H | H | OCH₃ | OCH₃ | N |
| 940 | CH₃ | H | H | CH₃ | CH₃ | N |
| 941 | CH₃ | H | H | CH₃ | Cl | CH |
| 942 | CH₃ | H | H | CH₃ | —OCH₂CH₂C— | |
| 943 | CH₃ | H | H | N(CH₃)₂ | Cl | N |
| 944 | CH₃ | H | H | CH₃ | OCHCO₂H (CH₃) | N |
| 945 | CH₃ | CH₃ | H | CH₃ | CH₃ | CH |
| 946 | CH₃ | CH₃ | H | OCH₃ | OCH₃ | CH |
| 947 | CH₃ | CH₃ | H | OCH₃ | OCH₃ | CH |
| 948 | CH₃ | CH₃ | H | CH₃ | OCH₃ | N |
| 949 | CH₃ | CH₃ | H | OCH₃ | OCH₃ | N |
| 950 | CH₃ | H | CH₃ | CH₃ | OCH₃ | CH |
| 951 | CH₃ | H | CH₃ | OCH₃ | OCH₃ | CH |
| 952 | CH₃ | H | CH₃ | CH₃ | OCH₃ | N |
| 953 | C₆H₅ | H | H | CH₃ | OCH₃ | CH |
| 954 | C₆H₅ | H | H | OCH₃ | OCH₃ | CH |
| 955 | C₆H₅ | H | H | CH₃ | OCH₃ | N |
| 956 | CH₃ | Cl | H | CH | CH₃ | CH |
| 957 | CH₃ | Cl | H | CH₃ | OCH₃ | CH |
| 958 | CH₃ | Cl | H | OCH₃ | OCH₃ | CH |
| 959 | CH₃ | Cl | H | CH₃ | OCH₃ | N |
| 960 | CH₃ | Cl | H | OCH₃ | OCH₃ | N |
| 961 | CH₃ | Br | H | CH₃ | OCH₃ | CH |
| 962 | CH₃ | Br | H | OCH₃ | OCH₃ | CH |
| 963 | CH₃ | Br | H | CH₃ | OCH₃ | N |
| 964 | CH₃ | NO₂ | H | CH₃ | CH₃ | CH |
| 965 | CH₃ | NO₂ | H | CH₃ | OCH₃ | CH |
| 966 | CH₃ | NO₂ | H | OCH₃ | OCH₃ | CH |
| 967 | CH₃ | NO₂ | H | CH₃ | OCH₃ | N |
| 968 | CH₃ | NO₂ | H | OCH₃ | OCH₃ | N |
| 969 | CH₃ | CO₂CH₃ | H | CH₃ | CH₃ | CH |
| 970 | CH₃ | CO₂CH₃ | H | CH₃ | OCH₃ | CH |
| 971 | CH₃ | CO₂CH₃ | H | OCH₃ | OCH₃ | CH |
| 972 | CH₃ | CO₂CH₃ | H | CH₃ | OCH₃ | N |
| 973 | CH₃ | CO₂CH₃ | H | OCH₃ | OCH₃ | N |
| 974 | CH₃ | CO₂C₂H₅ | H | CH₃ | CH₃ | CH |
| 975 | CH₃ | CO₂C₂H₅ | H | CH₃ | OCH₃ | CH |
| 976 | CH₃ | CO₂C₂H₅ | H | OCH₃ | OCH₃ | CH |
| 977 | CH₃ | CO₂C₂H₅ | H | CH₃ | OCH₃ | N |
| 978 | CH₃ | CO₂C₂H₅ | H | OCH₃ | OCH₃ | N |
| 979 | CH₃ | CO₂C₃H₇-n | H | CH₃ | OCH₃ | CH |
| 980 | CH₃ | CO₂C₃H₇-n | H | OCH₃ | OCH₃ | CH |
| 981 | CH₃ | CO₂C₃H₇-n | H | CH₃ | OCH₃ | N |
| 982 | CH₃ | CO₂CH₂CH=CH₂ | H | CH₃ | OCH₃ | CH |
| 983 | CH₃ | CO₂CH₂CH=CH₂ | H | OCH₃ | OCH₃ | CH |
| 984 | CH₃ | CO₂CH₂CH=CH₂ | H | CH₃ | OCH₃ | N |
| 985 | CH₃ | CO₂CH₃ | CH₃ | CH₃ | OCH₃ | CH |
| 986 | CH₃ | CO₂CH₃ | CH₃ | OCH₃ | OCH₃ | CH |
| 987 | CH₃ | CO₂CH₃ | CH₃ | CH₃ | OCH₃ | N |
| 989 | CH₃ | CON(CH₃)₂ | H | CH₃ | OCH₃ | CH |
| 990 | CH₃ | CON(CH₃)₂ | H | OCH₃ | OCH₃ | CH |

TABLE 3-continued

![structure with A-N-N, C, B, SO2NHCNH, X, Y, Z]

| Comp. No. | A | B | C | X | Y | Z |
|---|---|---|---|---|---|---|
| 991 | $CH_3$ | $CON(CH_3)_2$ | H | $CH_3$ | $OCH_3$ | N |
| 992 | $CH_3$ | $SO_2N(CH_3)_2$ | H | $CH_3$ | $OCH_3$ | CH |
| 993 | $CH_3$ | $SO_2N(CH_3)_2$ | H | $OCH_3$ | $OCH_3$ | CH |
| 994 | $CH_3$ | $SO_2N(CH_3)_2$ | H | $CH_3$ | $OCH_3$ | N |
| 995 | $CH_3$ | $SO_2N(C_2H_5)_2$ | H | $CH_3$ | $OCH_3$ | CH |
| 996 | $CH_3$ | $SO_2N(C_2H_5)_2$ | H | $OCH_3$ | $OCH_3$ | CH |
| 997 | $CH_3$ | $SO_2N(C_2H_5)_2$ | H | $CH_3$ | $OCH_3$ | N |
| 998 | $CH_3$ | $SO_2CH_3$ | H | $CH_3$ | $OCH_3$ | CH |
| 999 | $CH_3$ | $SO_2CH_3$ | H | $OCH_3$ | $OCH_3$ | CH |
| 1000 | $CH_3$ | $SO_2CH_3$ | H | $CH_3$ | $OCH_3$ | N |
| 1001 | H | H | H | $CH_3$ | $OCH_3$ | CH |
| 1002 | H | H | H | $OCH_3$ | $OCH_3$ | CH |
| 1003 | H | H | H | $CH_3$ | $OCH_3$ | N |
| 1004 | $C_2H_5$ | H | H | $CH_3$ | $CH_3$ | CH |
| 1005 | $C_2H_5$ | H | H | $CH_3$ | $OCH_3$ | CH |
| 1006 | $C_2H_5$ | H | H | $OCH_3$ | $OCH_3$ | CH |
| 1007 | $C_2H_5$ | H | H | $CH_3$ | $OCH_3$ | N |

The compounds of this invention represented by the above formula (I) can readily be produced by selecting suitably the following reaction scheme 1, 2 or 3.

Reaction scheme 1

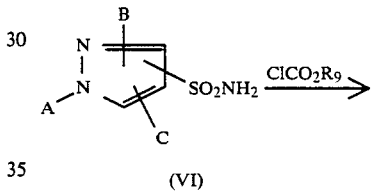

wherein A, B, C, D, X, Y and Z have the same meanings as defined above.

That is, a pyrazolesulfonylisocyanate derivative (IV) is dissolved in an inert solvent such as sufficiently dried dioxane, acetonitrile, etc., and to the resultant solution is added pyrimidine or a triazine derivative (V). By stirring the mixture, the reaction proceeds generally rapidly to give the compound (I) of this invention. In case when the reaction proceeds difficulty, a minute amount of a suitable base such as triethylamine, triethylenediamine, pyridine, sodium ethoxide, sodium hydride, etc. may be added to the reaction mixture, whereby the reaction can proceed easily.

Reaction scheme 2:

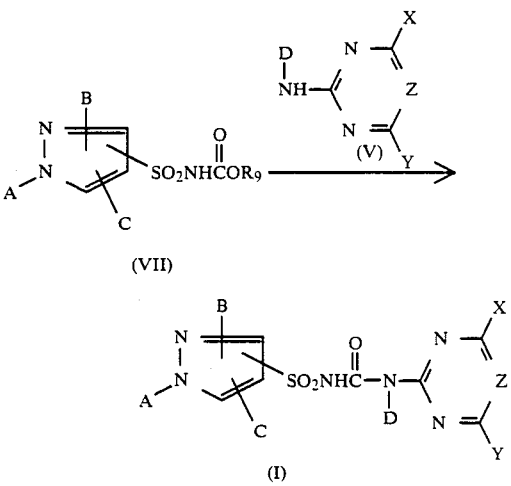

wherein A, B, C, D, X, Y and Z have the same meanings as defined above, and $R_9$ represents an alkyl group or a phenyl group.

That is, a pyrazolesulfonamide (VI) is allowed to react with a chlorocarbonate in a solvent such as acetone or methyl ethyl ketone in the presence of a base such as potassium carbonate, followed by acid precipitation with hydrochloric acid, etc., to give a compound (VII). This compound is then heated in a solvent such as toluene with a compound (V) to give the compound (I) of this inventions.

Reaction scheme 3

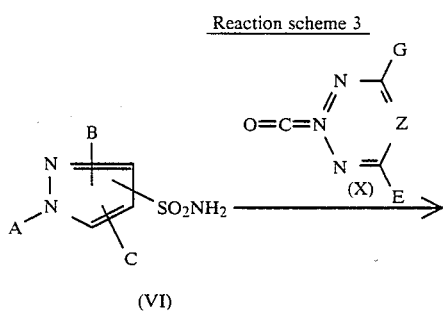

By referring to Japanese Unexamined Patent Publication No. 154471/1981, a pyrazolesulfonamide derivative (VI) can be allowed to react with a pyrimidine or a triazine isocyanate (X) to synthesize a compound (VIII), which is a part of the compound of this invention, followed by reaction with a sodium alcoholate, to further synthesize a compound (IX), which is also a part of the compounds of this invention.

The other reactant aminopyrimidine can be synthesized by referring to "The Chemicsty of Heterocyclic Compounds (Interscience Publishers Inc., New York) Vol. 16, The pyrimidines".

Aminotriazine can be synthesized according to the method disclosed in "Journal of Organic Chemistry, Vol. 28, pp. 1812–1821 (1963)".

2-Amino-4-methyl-5,6-dihydrofura[2,3-d]pyrimidine and 2-amino-4-chloro-5-chloroethyl-6-methylpyrimidine can be synthesized accordng to the method disclosed in Journal of Organic Chemistry, Vol. 16, pp. 1153 (1951).

Most of the pyrazolesulfonamide (VI) or the pyrazolesulfonyl isocyanate derivative (IV) used as the starting material in the reaction scheme 1, 2 or 3 are novel compounds, and they can be synthesized by selecting suitably the following reaction scheme 4, 5 or 6.

Reaction scheme 4

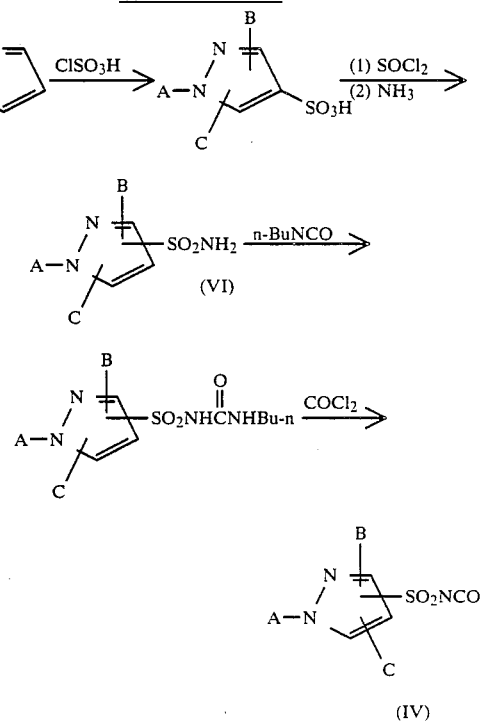

wherein A, B, C and Z have the same meanings as defined above, E represents a halogen atom, G represents H, Cl, Br, $C_1$–$C_4$ alkyl, $CF_3$, methoxymethyl or methoxy ethyl, and $R_{10}$ represents a lower alkyl group.

Reaction scheme 5

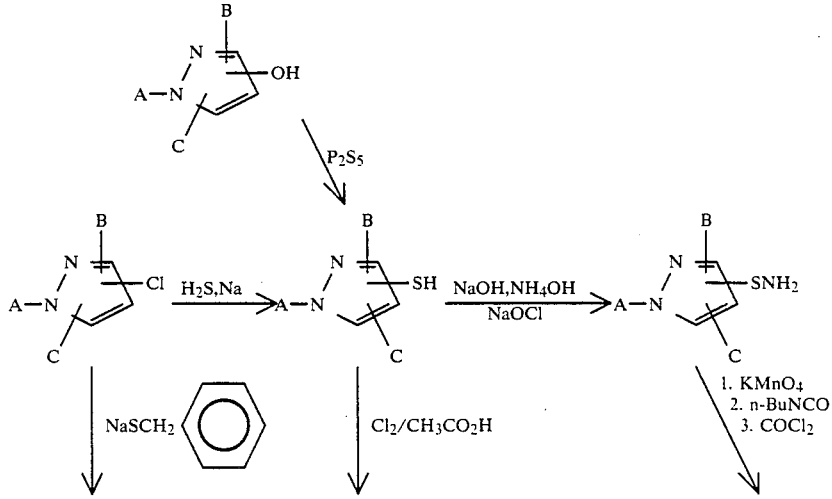

-continued

Reaction scheme 5

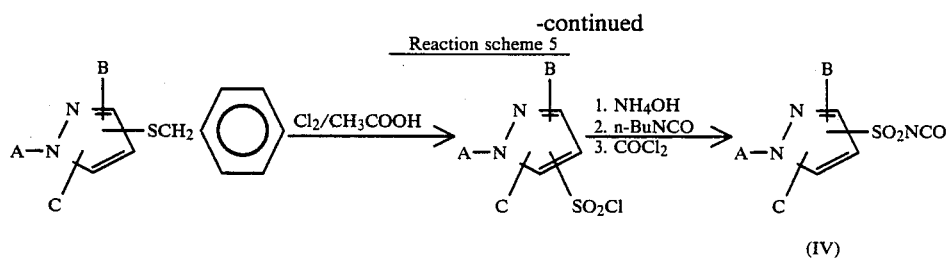

Reaction scheme 6

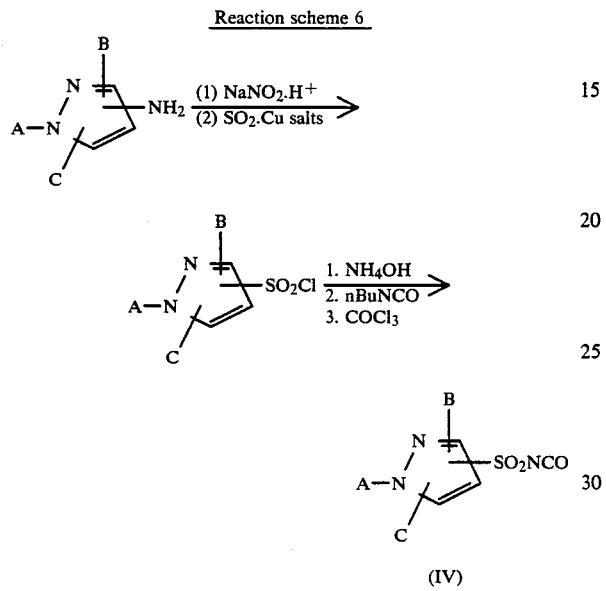

Most of the pyrazolesulfonyl isocyanate derivatives obtained hereinabove are unstable in the air, and should preferably be stored in a cold and dark place under a nitrogen atmosphere when they are to be stored, but alternatively they can be used as such without purification in many cases in the subsequent reaction step.

Most of the intermediates pyrazolesulfonamides (VI) to be used in this invention are novel compounds, and synthetic examples thereof are shown below as Reference examples.

REFERENCE EXAMPLE 1

Synthesis of 1,3-dimethyl-5-methoxypyrazole-4-sulfonamide:

Into 70 ml of chlorosulfonic acid was added dropwise under cooling at 5° C. or lower 12.6 g (0.1 mol) of 1,3-dimethyl-5-methoxypyrazole. After the addition, the mixture was stirred at 100° C. for 8 hours. Then, the reaction mixture was cooled to 80° C., followed by dropwise addition of 11.9 g (0.1 mol) of thionyl chloride over 30 minutes. After the dropwise addition, the mixture was stirred at 100° C. for 2 hours. The reaction mixture was cooled and poured carefully into ice-water, whereby crude 1,3-dimethyl-5-methoxy-pyrazole-4-sulfonylchloride was formed as crystals The crystals were separated by filtration, dissolved in 20 ml of tetrahydrofuran and the resultant solution was added dropwise into 100 ml of aqueous ammonia (28%) at 10° C. or lower. After the addition, the mixture was stirred at room temperature for 30 minutes. The reaction mixture was evaporated under reduced pressure to remove low boiling components, whereby crystals were precipitated. The crystals were filtered, washed with water and dried to give 11.5 g of 1,3-dimethyl-5-methoxypyrazole-4-sulfonamide melting at 144°–146° C.

REFERENCE EXAMPLE 2

Synthesis of 1,5-dimethyl-3-trifluoromethylpyrazole-4-sulfonamide:

Into 100 ml of an ethanolic solution of 25 g (0.16 mol) of trifluoroacetylacetone, there was added dropwise 7.4 g (0.16 mol) of methylhydrazine. After stirring at room temperature for 3 hours, the mixture was left to stand overnight and the solvent was evaporated to give 19.2 g of 1,5-dimethyl-3-trifluoromethylpyrazole as an oil. Following then the procedures as Reference example 1, this product was allowed to react with chlorosulfonic acid and then with thionyl chloride to obtain 29 g of 1,5-dimethyl-3-trifluoromethylpyrazole-4-sulfonylchloride, which was in turn reacted with aqueous ammonia (28%) in tetrahydrofuran to give 21.5 g of 1,5-dimethyl-3-trifluoromethylpyrazole-4-sulfonamide melting at 204°–206° C.

REFERENCE EXAMPLE 3

Synthesis of 1,3-dimehyl-5-methoxycarbonylpyrazole-4-sulfonamide:

Into 200 ml of chlorosulfonic acid, there was added dropwise 50.4 g (0.3 mol) of Ethyl 1,3-dimethyl-5-pyrazole carboxylate under cooling at 5° C. or lower. After heating at 120° C. under stirring for 10 hours, the reaction mixture was poured into ice-water and extracted with ether. After washing with water and drying, evaporation of the solvent gave 49 g of crude 1,3-dimethyl-4-chlorosulfonyl-5-pyrazole carboxylic acid as a solid.

23.9 g (0.1 mol) of this product was dissolved in 60 ml of tetrahydrofuran and the resultant solution was added dropwise into 150 ml of aqueous ammonia (28%) at 10° C. or lower. The mixture was stirred at room temperature for 4 hours and concentrated to dryness under reduced pressure. Then, 300 ml of dry methanol was added to the mixture, and the mixture was refluxed for 3 hours while passing gaseous hydrogen chloride thereinto. After the reaction, methanol was evaporated and ice-water was added to the residue, followed by extraction with ethyl acetate. After washing with water and drying, the solvent was evaporated and the crude crystals obtained were recrystallized from methanol to give 9.0 g of 1,3-dimethyl-5-methoxycarbonylpyrazole-4-sulfonamide melting at 174°–176° C.

REFERENCE EXAMPLE 4

Synthesis of 1,3-dimethyl-5-n-propylsulfonylpyrazole-4-sulfonamide:

With the use of 1,3-dimethyl-5-chloropyrazole as the starting material, following the procedure in the above Reference examples, there was obtained 5-chloro-1,3-dimethylpyrazole-4-sulfonamide melting at 173° C. Into a mixture of 14.1 g (0.067 mol) of the above sulfonamide, 10.7 g (0.268 mol) of sodium hydroxide and 120 ml of DMF, 6.6 g (0.087 mol) of n-propylmercaptan was added dropwise at room temperature. After the addition, the mixture was heated at 80°to 90° C. for 3 hours. After completion of the reaction, DMF was evaporated under reduced pressure, and the residue was diluted with water, adjusted to pH 4 with conc. hydrochloric acid and the precipitated crystals were collected by filtration. After drying, there was obtained 14.3 g of 1,3-dimethyl-5-n-propylthio-pyrazole-4-sulfonamide melting at 105°–106° C.

As the next step, this intermediate was dissolved in 80 ml of acetic acid and 23 g of 30% aqueous hydrogen peroxide was added dropwise into the resultant solution under ice-cooling. After stirring at room temperature for 4 hours, the reaction mixture was poured into water The precipitated crystals were collected by filtration to obtain 14 g of 1,3-dimethyl-5-n-propylsulfonylpyrazole-4-sulfonamide melting at 127°–129° C.

Following the procedures as described in Reference examples 1 to 4, there were synthesized the substituted pyrazolesulfoamides (IV) shown below

REFERENCE EXAMPLE 5

Synthesis of 1,5-dimethyl-3-phenylpyrazole-4-sulfonamide:

Obtained, following the above Reference examples, from 1,5-dimethyl-3-phenylpyrazole. m.p. 144°–148° C.

REFERENCE EXAMPLE 6

Synthesis of 5-chloro-1-methylpyrazole-4-sulfonamide:

Obtained from 5-chloro-1-methylpyrazole. m.p. 159°–152° C.

REFERENCE EXAMPLE 7

Synthesis of 1,5-dimethyl-3-methoxycarbonylpyrazole-4-sulfonamide:

Obtained from 1,5-dimethyl-3-methoxycarbonylpyrazole. m.p. 183°–185° C.

REFERENCE EXAMPLE 8

Synthesis of 1,5-dimethyl-3-ethoxycarbonylpyrazole-4-sulfonamide:

Obtained from 1,5-dimethyl-3-ethoxycarbonylpyrazole. m.p. 159°–161° C.

REFERENCE EXAMPLE 9

Synthesis of 1,3-di-methylpyrazole-4-sulfonamide:

Obtained from 1,3-dimethylpyrazole. m.p. 114°–115° C.

Reference example 10:

Synthesis of 3,5-dimethylpyrazole-4-sulfonamide:

Obtained from 3,5-dimethylpyrazole. m.p.215°–223° C.

Reference example 11:

Synthesis of 1,5-dimethylpyrazole-4-sulfonamide:

Obtained from 1,5-dimethylpyrazole. m.p.165°–166° C.

Reference example 12:

Synthesis of 5-methoxy-1-methyl-3-i-propylpyrazole-4-sulfonamide:

Obtained from 5-methoxy-1-methyl-3-i-propylpyrazole. m.p.114°–115° C.

Reference example 13:

Synthesis of 1,3-dimethyl-5-ethoxycarbonylpyrazole-4-sulfonamide:

Obtained from 1,3-dimethyl-5-ethoxycarbonylpyrazole. m.p.150°–154° C.

Reference example 14:

Synthesis of 3,5-dimethyl-1-phenylpyrazole-4-sulfonamide:

Obtained from 3,5-dimethyl-1-phenylpyrazole. m.p.178°–180° C.

Reference example 15:

Synthesis of 3-ethoxycarbonyl-1-methyl-5-phenylpyrazole-4-sulfonamide:

A solution of 7.5 ml of chlorosulfonic acid and 15 xl of dry chloroform was cooled to 0° C., and a solution of 11.5 g (0.05 mol) of 3-ethoxycarbonyl-1-methyl5-phenylpyrazole in 25 ml of dry chloroform was added dropwise thereinto. Then, the mixture was stirred at room temperature for one hour and under reflux for 3 hours. After the reaction, by evaporation of chloroform, there was obtained oily 3-ethoxycarbonyl-1-methyl-5-phenylpyrazole-4-sulfonic acid. As the next step, at room temperature 20.9 g of phosphorus pentachloride was added portionwise, followed by stirring at 90° to 100° C. for one hour. The reaction mixture was added into ice-water and extracted with ether to obtain 14.7 g of 3-ethoxycarbonyl-1-methyl-5-phenylpyrazole-4-sulfonylchloride. Then, the resultant sulfonylchloride was dissolved in 20 ml of acetone and 4.48 g of KHCO was added to the solution. After a solution of 2.7 g of aqueous ammonia (28 %) and 6.5 ml of acetone was added dropwise thereinto at room temperature, the mixture was heated at 50 to 60 ° C. for 30 minutes. After evaporation of acetone, water was added to the residue, whereby 12.9 g of the title compound was precipitated as a solid. Recrystallization from benzene gave 8.4 g of the product. m.p. 141°–144° C.

Following the procedures as described above, there were synthesized the substituted pyrazolesulfonamides shown below.

Reference example 16:

Synthesis of 5-chloro-1,3-dimethylpyrazole-4-sulfonamide:

Obtained from 5-chloro-1-3-dimethylpyrazole. m.p. 173° C.,

Reference example 17:

Synthesis of 1-ethyl-5-methyl-3-methoxycarbonyl-pyrazole-4-sulfonamide:

Obtained from 1-ethyl-5-methyl-3-methoxycarbonyl-pyrazole. m.p. 165°–168° C.,

Reference example 18:

Synthesis of 5-ethyl-1-methyl-3-methoxycarbonylpyraxole-4-sulfonamide:

Obtained from 5-ethyl-1-methyl-3-methoxycarbonyl-pyrazole. m.p. 188°–191° C.

Reference example 19:

Synthesis of 1-ethyl-3-methyl-5-methoxycarbonyl-pyrazole-4-sulfonamide:

Obtained from 1-ethyl-3-methyl-5-methoxycarbonyl-pyrazole. m.p. 130°–133° C.,

Reference example 20

Synthesis of 3-ethyl-1-methyl-5-methoxycarbonyl-pyrazole-4-sulfonamide:

Obtained from 3-ethyl-1-methyl-5-methoxycarbonyl-pyrazole. m.p. 162°–165° C.,

Reference example 21:

Synthesis of 1,3-dimethyl-5-dimethylcarbamoylpyrazole-4-sulfonamide:

Obtained from 1,3-dimethyl-5-dimethylcarbamoyl-pyrazole. m.p. 150°–152° C.

Reference example 22:

Synthesis of 1-methylpyrazole-4-sulfonamide:

Obtained from 1-methylpyrazole. m.p. 122°–123° C.

Reference example 23:

Synthesis of 1,3-dimethyl-5-i-propoxycarbonylpyrazole-4-sulfonamide:

Obtained by heating 1,3-dimethyl-5-carboxyl-pyrazole-4-sulfonamide obtained in Reference example 3 in i-propyl alcohol in the co-presence of hydrogen chloride m.p. 105°–108° C., Reference example 24:

Synthesis of 1,3-dimethyl-5-(N,N-tetramethylene-carbamoyl)-4-sulfonamide:

Obtained from 1,3-dimethyl-5-(N,N-tetramethylenecarbamoyl)pyrazole. m.p. 92°–95° C.

Reference example 25: Synthesis of 4-ethoxycarbonyl-1-methylpyrazole-5-sulfonamide:

(1) Synthesis of ethyl-5-hydroxy-1-methyl-4-pyrazolecarboxylate

To a solution of 216 g (1 mol) of diethylethoxymethylenemalonate in 216 g of ethanol, there was added 46 g (1 mol) of methylhydrazine at 10° C. Then, at room temperature, the mixture was stirred and further refluxed for one hour, and thereafter the reaction mixture was left to stand. The precipitated crystals were filtered and dried to obtain 148 g of the title compound melting at 134°–135° C.

(2) Synthesis of ethyl 5-chloro-1-methyl-4-pyrazole carboxylate:

A mixture of 10 g of ethyl 5-hydroxy-1-methyl-4-pyrazole carboxylate and 50 ml of phosphorus oxychloride was stirred at 90° to 100° C. for 65 hours. Excessive phosphorus oxychloride was evaporated under reduced pressure, and the residue was poured into ice-water. The precipitated crystals were filtered and dried to obtain 4.5 g of 5-chloro-1-methyl-4-pyrazole carboxylic acid. The filtrate was neutralized with aqueous ammonia (28%) and extracted with ether. After drying of the extract, evaporation of the solvent gave 4.0 g of ethyl 5-chloro-1-methyl-4-pyrazole carboxylate. To 5-chloro-1-methyl-4-pyrazole carboxylic acid were added 30 ml of thionyl chloride and 0.2 ml of dimethylformamide, and the mixture was refluxed for 5 hours. Then, excessive thionyl chloride was evaporated and the residue was added to dry ethanol. After stirring at room temperature for 3 hours, the solvent was evaporated and ether was added to the residue. After washing with water, drying and evaporation of the solvent, there was obtained 4.5 g of ethyl 5-chloro-1-methyl-4-pyrazole carboxylate as an oil. Total of the title compound: 8.5 g.

(3) Synthesis of ethyl 5-mercapto-1-methyl-4-pyrazole carboxylate:

After 2.2 g (0.094 mol) of sodium was dissolved in 35 ml of ethanol, 50 ml of dimethylformamide was added to the resultant solution, and most of ethanol was removed. Then, under cooling, hydrogen sulfide was passed into the mixture to saturation, followed by addition of 7.4 g (0.039 ml) of ethyl 5-chloro-1-methyl-4-pyrazole carboxylate. After stirring at 70 to 80 ° C. for 3.5 hours, the reaction mixture was concentrated under reduced pressure Ice-water was added to the reside, and insolubles were filtered off. The filtrate was made acidic, extracted with chloroform and dried, followed by evaporation of the solvent, to give 6.8 g of the title compound as an oil.

(4) Synthesis of 4-ethoxycarbonyl-1-methylpyrazole-5-sulfonamide:

To 100 ml of a 28 % aqueous ammonia, there was added 20 ml of aqueous solution containing 7.1 g of ethyl-5-mercapto-1-ethyl-4-pyrazole carboxylate and 1.6 g of sodium hydroxide. To this reaction mixture was added 61 g of 6 % aqueous NaOCl solution at 5°–10° C. The precipitated crystals were filtered and washed with water. The resultant moist sulfenamide (5.6g) was suspended in water and an aqueous saturated solution of 5.5 g of potassium permanganate was added to the suspension at room temperature. After stirring vigorously at room temperature, the mixture was filtered. The filtrate was made acidic and extracted with ethyl acetate. After drying, the solvent was evaporated to obtain 1.8 g of the title compound. m.p. 102°-104° C.

(5) Synthesis of 4-ethoxycarbonyl-1-methylpyrazole-5-sulfonamide (alternative method):

A solution of 3.0 g of ethyl 5-mercapto-1-methyl-4-pyrazole carboxylate in 50 ml acetic acid was stirred while passing chlorine at 15 to 20 ° C. Then, after nitrogen was passed into the mixture, the reaction mixture was poured into ice-water and the crystals precipitated were separated by filtration.

The sulfonyl chloride as prepared above was dissolved in 20 ml of tetrahydrofuran, and added under ice-cooling to 50 ml of 28 % aqueous ammonia. After stirring at room temperature for 2 hours, the reaction mixture was concentrated under reduced pressure. The precipitated crystals were filtered, washed with water and further washed with n-hexane. After drying, 1.3 g of the title compound was obtained. m.p. 102°-104° C.

Reference example 26

Synthesis of 4-methoxycarbonyl-1-methylpyrazole-5-sulfonamide:

Synthesized similarly as in Reference example 25. m.p. 127°-128° C.,

The respective intermediates have the following physical properties.

Methyl 5-hydroxy-1-methyl-4-pyrazole carboxylate: m.p. 111°-113° C.,

Methyl 5-chloro-1-methyl-4-pyrazole carboxylate: m.p. 70°-71° C.,

Methyl 5-mercapto-1-methyl-4-pyrazole carboxylate: m.p. 64°-66° C.,

Reference example 27:

Synthesis of 1,3-dimethylpyrazole-5-sulfonamide and 4-chloro-1,3-dimethyllpyrazole-5-sulfonamide (1) Synthesis of 1,3-dimethyl-5-mercaptopyrazole To a solution of 84 g (0.75 mol) of 1,3-dimethyl-5-hydroxypyrazole in 630 ml of xylene was added portionwise 65.3 g (0.294 mol) of phosphorus penlasulfide at 110° to 120° C. After heating under reflux for 1.5 hours, the hot reaction mixture was filtered. The filtrate was concentrated to give 21.4 g of the title compound m.p. 130 -132° C.

(2) Synthesis of 4-chloro-1.3-dimethylpyrazole-5-sulfonamide

Into a solution of 12 g (0.094 ml) of the mercaptopyrazole obtained above in a mixture of acetic acid (100 ml) and water (15 ml), chlorine was passed at 10° C. for 2 hours. After completion of the reaction, the mixture was poured into ice-water and extracted with ether. The organic extracts were washed with water, dried and evaporated to give 19.5 g of crude 4-chloro-1,3-dimethylpyrazole-5-sulfonyl chloride as an oil.

Then, into 130 ml of aqueous ammonia (28 %) was added dropwise the sulfonyl chloride obtained above in 50 ml of THF at 10° C. or lower. After the addition, the reaction mixture was stirred at room temperature for 3 hours and then concentrated under reduced pressure to form precipitates.

The precipitated solids were filtered, washed with water and dried to give 10.8 g of the title compound. m.p. 135°-138° C.

Further, the filtrate obtained above was extracted with benzene several times and the aqueous layer was concentrated under reduced pressure to dryness. The residual product was extracted with 100 ml of ethyl acetate. After evaporation of the solvent there was also obtained 4.0 g of 1,3-dimethylpyrazole-5-sulfonamide. m.p. 63 -66° C.

Reference example 28:

Synthesis of 1,3-dimethyl-4-nitropyrazole-5-sulfonamide (1) Synthesis of 5-chloro-1,3-dimethyl-4-nitropyrazole Concentrated $H_2SO_4$(35 g) was added to 10 ml of 90% $HNO_3$ and at 75°-85° C., 13 g (0.1 mol) of 5-chloro-1,3-dimethylpyrazole was added dropwise with stirring to maintain the temperature at 85° C. After completion of the addition, the mixture was heated at 75 -85° C. for 1.5 hr. The nitration mixture was cooled and poured into ice. The suspension was filtered and the solid was washed with water and dried to give 14.5 g of the title compound. m.p. 70° C.

(2) Synthesis of 5-benzylthio-1,3-dimethyl-4-nitropyrazole

Benzylmercaptan (50.8 g) (0.41 mol) was added to 21 g of sodium methoxide in 480 ml of DMF under ice-cooling and then 65.2 g (0.37 ml) of 5-chloro-2,3-dimethyl-4-nitropyrazole was added. After stirring at room temperature for 3 hr., DMF was evaporated under reduced pressure, and the residue was diluted with ice-water. The precipitated solids were filtered, washed with water and further with n-hexane and dried to give 82.4 g of the title compound. m.p. 82 -83° C.

(3) Synthesis of 1,3-dimethyl-4-nitropyrazole-5-sulfonamide

Into a solution of 40 g (0.152 mol) of 5-benzylthio-1,3-dimethyl-4-nitropyrazole in 300 ml of acetic aid and 30 ml of water chlorine was passed at 3 to 8° C. for 1.5 hr. After completion of the reaction, the mixture was poured into ice-water and extracted with ether to give crude 1,3-dimethyl-4-nitropyrazole-5-sulfonylchloride as an oil.

The sulfonylchloride obtained above in 50 ml of THF was added into 150 ml of aqueous ammonia (28%) under ice-cooling. After stirring at room temperature for 5 hrs, the reaction mixture was evaporated under reduced pressure. The precipitated solids were filtered, washed with water and further with n-hexane and dried to give 19.6 g of the title compound. m.p. 138°-140° C.

Reference example 29:

Synthesis of 1,3-dimethyl-4-dimethylsulfamoylpyrazole-5-sulfonamide:

(1) Syntheisis of N,N-dimethyl-(5-chloro-1,3-dimethylpyrazole)-4-sulfonamide

Into 150 xl of chlorosulfonic acid was added dropwise under cooling at 5° C. or lower, 30 g (0.23 ml) of 5-chloro-1,3-dimethylpyrazole. After the addition, the mixture was stirred at 100° C. for 8 hours. Then, the reaction mixture was cooled to 80° C., followed by dropwise addition of 36 g of thionyl chloride over 30 minutes After the addition, the mixture was stirred at 100° C. for an additional 2 hours. The reaction mixture was cooled on ice and poured carefully into ice-water, whereby crude 5-chloro-1,3-dimethylpyrazole-4-sulfonylchloride (50 g) was formed as crystals. Subsequently, into a solution of 40 g of dimethylamine in 250 ml of THF, the above compound was added under cooling and the reaction mixture was stirred at room temperature for 3 hours. After the reaction, THF was evaporated under reduced pressure and into the residue was added ether and washed with water. After drying and evaporating the etherial solution, there was obtained 47 g of the title compound m.p. 53 –55° C.

(2) Synthesis of N,N-dimethyl-(5-benzylthio-1,3-dimethylpyrazole)-4-sulfonamid

Obtained, following the above Reference example 28-(2), from N,N-dimethyl-(5-chloro-1,3-dimethylpyrazole)-4-sulfonamide. m.p. 108 –109° C.

(3) Synthesis of 1,3-dimethyl14-dimethylsulfamoyl-pyrazole-5-sulfonamide

Obtained, following the above Reference example 28-(3), from N,N-dimethyl-(5-benzylthio-1,3-dimethylpyrazole)-4-sulfoamide. m.p. 209°–210° C.

Reference example 30:

Synthesis of 1-methylpyrazole-3-sulfonamide:

To a solution of 32 g (0.33 mol) of 1-methyl-3-aminopyrazole in a mixture of conc. hydrochloric acid (120 ml) and acetic acid (40 ml) was added a solution of 34.1 g (0.494 mol) of sodium nitrite in water (80 ml at −10° to 0° C. The solution was stirred at −5° C. for 30 minutes and then added, in several portions, into a sulfur dioxide saturated solution of acetic aid (440 ml) containing 6.7 g of cuprous chloride at −10° to −5° C. The resulting solution was stirred at 0° to 5° C. for 4 hours and then poured into ice-water and extracted with ether. The extracts were washed with water and saturated aqueous sodium bicarbonate, dried and evaporated to give 20.8 g of crude sulfonylchloride as an oil. The sulfonylchloride obtained above was dissolved in 50 ml of THF and added to 150 ml of aqueous ammonia (28%) at 10° C. or lower. After stirring at room temperature for 3 hours, the reaction mixture was concentrated under reduced pressure to form precipitates. The precipitated solids were filtered, washed with water and further with n-hexane and dried to give 24. g of the title compound. m.p. 156 –158° C.

Specific synthetic examples of the compounds according to this invention are illustrated below by using the substituted pyrazolesulfonamides (VI) obtained in Reference examples, but this invention is not limited thereto.

EXAMPLE 1

Synthesis of N-[(4-methoxy-6-methylpyrimidin-2-yl)aminocarbonyl]-1,3-dimethyl-5-methoxypyrazole-4-sulfonamide (Compound No. 292):

To a mixture of 10.25 g (0.05 mol) of the sulfonamide obtained in Reference example 1, 8.29 g (0.06 mol) of dry potassium carbonate and 50 ml of dry acetone was added 4.95 g (0.05 mol) of n-butyl isocyanate at room temperature, and the mixture was stirred for 4 hours. Then, the reaction mixture was refluxed for one hour. After the reaction, acetone was evaporated under reduced pressure and the residue was dissolved in 200 ml of water. After separation of a trace of water insolubles, the filtrate was made acidic with hydrochloric acid and the crystals formed were filtered, washed with water and dried to give 9.2 g of N-(butylcarbamoyl)-1,3-dimethyl-5-methoxypyrazole-4-sulfonamide melting at 135 –142 ° C.

Into a mixture of 100 ml of dry benzene and 9.12 g (0.03 mol) of N-(n-butylcarbamoyl)-1,3-dimethyl-5-methoxypyrazole-4-sulfonamide, under reflux, 8.9 g (0.09 mol) of phosgene was passed over 1.5 hours. Then, the reaction mixture was further refluxed for 30 minutes. After completion of the reaction, evaporation of benzene under reduced pressure gave crude 1,3-dimethyl-5-methoxypyrazole-4-sulfonyl isocyanate as an oil.

The crude isocyanate was taken out in an amount of 1.39 g (0.006 mol), dissolved in 20 ml of dry acetonitrile and 0.695 g (0.005 mol) of 4-methoxy-6-methyl-2-aminopyrimidine was added to the resultant solution. The mixture was stirred at room temperature for one hour, then refluxed for 30 minutes, followed by cooling. The crystals formed were filtered, washed and dried to obtain 1.09 g of N-[(4-methoxy-6-methylpyrimidin-2-yl)aminocarbonyl]-1,3-dimethyl-5-methoxypyrazole-4-sulfonamide melting at 183°–184° C.

EXAMPLE 2

Synthesis of N-[(4-methoxy-6-methyl-1,3,5-triazin-2-yl)amino-carbonyl]-1,3-dimethyl-5-methoxycarbonylpyrazole-4-sulfonamide (Compound No. 387):

With the use of 6.8 g of the sulfonamide obtained in Reference example 3, following the procedure as in Example 1, there was obtained 8.6 g (0.026 mol) of N-(n-butylcarbamoyl)-1,3-dimethyl-5-methoxycarbonylpyrazole-4-sulfonamide. The compound obtained was mixed into 200 ml of xylene and under reflux 7.7 g (0.078 mol) of phosgene was passed into the mixture over 1.5 hours. The reaction mixture was refluxed for 30 minutes, followed by evaporation of xylene, to obtain crude 1,3-dimethyl-5-methoxycarbonylpyrazole-4-sulfonyl isocyanate as an oil.

The crude isocyanate was taken out in an amount of 0.90 g (0.0035 mol) and dissolved in 20 ml of dry acetonitrile and 0.35 g of (0.0025 mol) of 2-amino-4-methoxy-6-methyl-5-triazine was added to the solution. After the mixture was stirred at room temperature for 2 hours, the reaction mixture was refluxed for 30 minutes and cooled. The crystals formed were filtered, washed and dried to obtain N-[(4-methoxy-6-methyl-1,3,5-triazin-2-yl)aminocarbonyl]-1,3-dimethyl-5-methoxycarbonyl-pyrazole-4-sulfonamide melting at 195°–198° C.

EXAMPLE 3

Synthesis of N-[(4,6-dimethylpyrimidin-2-yl)aminocarbonyl]-1,3-dimethyl-5-propenyloxycarbonylpyrazole-4-sulfonamide (Compound No. 425):

Into a mixture of 17.4 ml of methanol and 8.7 g of 10 % aqueous sodium hydroxide was added 3.3 g (0.00864 mol) of N-[(4,6-dimethylpyrimidin-2-yl)aminocarbonyl]1,3-dimethyl-5-methoxycarbonylpyrazole-4-sulfonamide (Compound No. 384), and the resultant mixture was refluxed for 45 minutes. After the reaction, the reaction mixture was made acidic with conc. hydrochloric acid to obtain 2.3 g of a hydrolyzed compound (Compound No. 435). The above compound was taken out in an amount of 1.5 g (0.00408 mol), dissolved in 8 ml of THF and 0.416 g of triethylamine was added to the resultant solution. After stirring for 10 minutes, a solution of 0.493 g of allyl bromide in 8 ml of THF was added and the mixture was refluxed for 3 hours. The precipitated salt was filtered off and the filtrate was evaporated to obtain 0.5 g of the crystals of the title compound. m.p. 180°–183° C.,

EXAMPLE 4

Synthesis of N-[(4.6-dimethoxy-1,3,5-triazin-2-yl)aminocarbonyl]-1,3-dimethyl-5-dimethylcarbamoylpyrazole-4-sulfonamide (Compound No. 484):

In 15 ml of dry acetonitrile, there were added 1.97 g example 21 and 1.68 g (0.0088 mol) of dichloro-S-triazinyl isocyanate, and the mixture was refluxed for one hour. The reaction mixture was then left to stand at room temperature to give 2.2 g of crystals of N4,6-dichloro-1,3,5-triazin-2-yl)aminocarbonyl]-1,3-dimethyl-5-dimethylcarbamoylpyrazole-4-sulfonamide. m.p.182°–185° C.

Then, the above compound was taken out in an amount of 1.3 g (0.00297 mol) and added into 12 ml of methanol. Into this mixture, there were added portonwise sodium methoxide prepared from 0.205 g of sodium and 5 ml of methanol. After the reaction, the mixture was filtered and methanol was evaporated. The residue was dissolved in ice-water and made acidic with hydrochloride acid, whereby 0.8 g of the crystals of the title compound was obtained. m.p. 170°–175° C.,

EXAMPLE 5

Synthesis of N-[(4-methoxy-6-methylpyrimidin-2-yl)aminocarbonyl]-1,3-dimethyl-5-dimethylsulfamoylpyrazole-4-sulfonamide (Compound No. 596):

With the use of 39 g (0.186 mol) of the sulfonamide obtained in Reference example 16, following the procedure as in Example 1, there was prepared 57.6 g N-(n-butylcarbamoyl)-1,3-dimethyl-5-chloropyrazole-4-sulfonamide. m.p. 188° C., As the next step, 4.7 g of 55% sodium hydride was added to 100 ml of dimethylformamide and 9.1 g (0.074 mol) of benzylmercaptan was added to the mixture, followed by portionwise addition of 15 g (0.049 g) of the sulfonamide as prepared above. After stirring at room temperature for several hours, the reaction mixture was further stirred at 70 to 80 ° C. for 5 hours. After evaporation of the solvent, the residue was added into ice-water and the insolubles were filtered off. The filtrate was made acidic with hydrochloric acid to precipitate 19 g of N-(n-butyl-carbamoyl)1,3-dimethyl-5-benzylthiopyrazole-4-sulfonamide. Then, into a solution of 19 g (0.0479 mol) of the above compound dissolved in 100 ml of acetic acid, chlorine was passed at 10° to 20° C. for 1.5 hours. After the reaction, the reaction mixture was poured into ice-water to precipitate N-(n-butylcarbamoyl)-1,3-dimethyl-5 -chlorosulfonyl-4-sulfonamide. Subsequently, into a solution of 8.6 g of dimethylamine in 50 ml of THF, the above compound was added and the mixture was stirred at room temperature for 3 hours. After the reaction, THF was evaporated, and the residue was dissolved in an aqueous potassium carbonate solution. After removal of the insolubles, the residual solution was made acidic with hydrochoric acid to precipitate 10.0 g (0.026 mol) of N-(n-butylcarbamcyl)1,3-dimethyl-5-dimethylsulfamoyl-4-sulfonamide. m.p. 163°–164° C.

From the compound as prepared above, following the procedures of Examples 1 and 2, there was synthesized 1,3-dimethyl-5-dimethylsulfamoylpyrazole-4-sulfonyl isocyanate, which was in turn allowed to react with 2-amino-4-methoxy-6-methylpyrimidine to obtain the title compound. m.p. 215°–217° C.,

EXAMPLE 6

Synthesis of N-[(4,6-dimethyylpyrimidin-2-yl)aminocarbonyl]-1,3-dimethyl-5-ethylthiopyrazole-4-sulfonamide: (Compound No.742)

Into 10 ml of dimethylformamide, there were added 1.5 g (0.0042 mol) of N-[(4,6-dimethylpyrimidin-2-yl)aminocarbonyl]-1,3-dimethyl-5-chloropyrazole-4-sulfonamide (Compound No. 85), 0.4 g of ethylmercaptan and 0.67 g of sodium hydroxide, and the resultant mixture was stirred at 60 to 70 ° C. for 4 hours. After the reaction, the solvent was evaporated, and the residue was added into ice-water, followed by acidification with hydrochloric acid, to precipitate 1.2 g of the crystals of the title compound. m.p. 189°–190° C.,

EXAMPLE 7

Synthesis of N-[(4,6-dimethoxypyrimidin-2-yl)aminocarbonyl]-4-ethoxycarbonyl-1-methylpyrazole-5-sulfonamide (Compound No. 835):

To a mixture of 5.0 g of4-ethoxycarbonyl-1-methylpyrazole-5-sulfonamide(Reference example 25), 4.45 g of dry potassium carbonate and 50 ml of acetone was added 2.13 g of n-butyl isocyanate at room temperature, and the mixture was stirred under reflux for 3 hours. After the reaction, acetone was evaporated under reduced pressure, and ice-water was added to the residue, followed by filtration of the insolubles. The filtrate was made acidic with hydrochloric acid and the crystals precipitated were filtered, washed with water and dried to give 5.1 g of N-(n-butylcarbamoyl)-4-ethoxycarbonyl-1-methylpyrazole-5-sulfonamide melting at 117°–119° C. Then, this product was added into 120 ml of dry toluene, and 9.1 g of phosgene was passed into the mixture under reflux, followed further by refluxing for 1.5 hours. After completion of the reaction, the reaction mixture was concentrated under reduced pressure to obtain crude sulfonyl isocyanate.

The above crude sulfonyl isocyanate (0.98 g) was added to a solution of 0.4 g of 2-amino-4,6-dimethoxy pyrimidine in 20 ml of dry acetonitrile and the mixture was stirred at room temperature. The crystals formed were filtered, washed and dried to obtain 0.8 g of the title compound melting at 170°–172° C.

EXAMPLE 8

Synthesis of N-[(4-methoxy-6-methylpyrimidin-2-yl)aminocarbonyl]-4-methoxycarbonyl-1-methylpyrazole-5-sulfonamide (Compound No. 816):

With the use of the sulfonamide obtained in Reference example 26, following the procedure of Example 7, there was obtained N-(n-butylcarbamoyl)-4-methoxycarbonyl-1-methylpyrazole-5-sulfonamide. m.p. 88°–90° C., Further, following the procedure of Example 7, there was synthesized a sulfonyl isocyanate, which was further allowed to react with 2-amino-4-methoxy-6-methylpyrimidine to obtain the title compound melting at 183°–184° C.

EXAMPLE 9

Synthesis of N-[(4,6-dimethylpyrimdine-2-yl)aminocarbonyl]-4-chloro-1,3-dimethylpyrazole-5-sulfonamide (Compound No. 789):

(1) Synthesis of N-(ethoxycarbonyl)-4-chloro-1,3-dimethylpyrazole-5-sulfonamide

A mixture of 2.1 g (0.01 mol) of the sulfonamide obtained in Reference example 27, 1.41 g (0.013 mol) of ethyl chloroformate and 1.73 g (0.0125 mol) of potassium carbonate in 30 ml of dry acetone was stirred at room temperature for 18 hours. After the reaction, acetone was evaporated under reduced pressure and the residue was dissolved in water. The resultant solution was made acidic with conc. hydrochloric acid and extracted with ether. After evaporation of ether, the precipitated solids were recrystallized from a mixture of benzene and n-hexane to obtain 2.0 g of the title compound. m.p. 106 –109° C.

(2) Synthesis of N-[(4,6-dimethylpyrimidine-2-yl)aminocarbonyl]-4-chloro-1,3-dimethylpyrazole-5-sulfonamide Into 1.41 g (0.005 ml) of the compound obtained above in 10 ml of xylene was added 0.74 g (0.006 ml) of 2-amino-4,6-dimethylpyrimidine and the reaction mixture was refluxed for 2 hours. The resultant mixture was left to stand at room temperature to give 1.2 g of the title compound. m.p. 191°–194° C.

EXAMPLE 10

Synthesis of [(4-methoxy-6-methylpyrimidine-2-yl)aminocarbonyl]-1-methylpyrazole-3-sulfonamide (Compound No. 936);

With the use of the sulfonamide obtained in Reference example 30, following the procedure of Example 7, there was obtained N-(n-butylcarbamoyl)-1-methylpyrazole3-sulfonamide. m.p. 168 –169° C.

Further, following the procedure of Example 7, there was synthesized a sulfonyl isocyanate, which was further allowed to react with 2-amino-4-methoxy-6-methylpyrimidin to obtain the title compound. m.p. 185°–186° C.

Next, similarly as in the above Examples, specific compounds were prepared and they are shown together with the compounds synthesized in Examples 1 to 10 in Table 4.

TABLE 4

| Comp. No. | m.p. (°C.) | Status |
|---|---|---|
| 1 | 211~214 | white crystal |
| 2 | 201~203 | " |
| 3 | 171~172 | " |
| 4 | 180~181 | " |
| 5 | 173~174 | " |
| 6 | 115~120 | " |
| 7 | 171~175 | " |
| 8 | 177~179 | " |
| 9 | 174~176 | " |

TABLE 4-continued

| Comp. No. | m.p. (°C.) | Status |
|---|---|---|
| 10 | 163~166 | " |
| 11 | 187~190 | " |
| 12 | 183~184 | " |
| 13 | 219~220 | " |
| 14 | 210~211 | " |
| 15 | 181~183 | " |
| 16 | 202~203 | " |
| 17 | 180~182 | " |
| 18 | 180~182 | " |
| 19 | 202~203 | " |
| 20 | 213~214 | " |
| 21 | 222~224 | " |
| 22 | 226 | " |
| 85 | 212~217 | " |
| 86 | 192~196 | " |
| 87 | 184~188 | " |
| 88 | 148~152 | " |
| 89 | 153~157 | " |
| 110 | 199~202 | " |
| 111 | 178~181 | " |
| 112 | 183~186 | " |
| 113 | 220~227 | " |
| 114 | 164~165 | " |
| 138 | 242~244 | " |
| 139 | 232~234 | " |
| 140 | 210~214 | " |
| 141 | 190~193 | " |
| 142 | 190~195 | " |
| 146 | 242~244 | " |
| 147 | 216~218 | " |
| 148 | 221~223 | " |
| 150 | 242~245 | " |
| 159 | 163~166 | " |
| 160 | 198~200 | " |
| 161 | 201~203 | " |
| 162 | 208~210 | " |
| 165 | 212~215 | " |
| 166 | 219~220 | " |
| 177 | 197~199 | " |
| 178 | 207~209 | " |
| 179 | 191~193 | " |
| 291 | 189~192 | " |
| 292 | 183~184 | " |
| 293 | 148~149 | " |
| 294 | 158~161 | " |
| 295 | 174~175 | " |
| 304 | 230~232 | " |
| 305 | 206~208 | " |
| 306 | 202~204 | " |
| 307 | 185~195 | " |
| 308 | 185~188 | " |
| 316 | 203~205 | " |
| 317 | 220~225 | " |
| 320 | 194~196 | " |
| 324 | 202~203 | " |
| 325 | 187~188 | " |
| 327 | 191~194 | " |
| 328 | 184~186 | " |
| 356 | 182~183 | " |
| 357 | 163~164 | " |
| 358 | 176~178 | " |
| 359 | 158~165 | " |
| 360 | 167~169 | " |
| 361 | 169~171 | " |
| 384 | 195~198 | " |
| 385 | 187~190 | " |
| 386 | 182~183 | " |
| 387 | 195~198 | " |
| 388 | 173~176 | " |
| 391 | 209~211 | " |
| 403 | 185~188 | " |
| 409 | 186 | " |
| 410 | 180~183 | " |
| 411 | 175~180 | " |
| 565 | 179~180 | " |
| 566 | 178~179 | " |
| 567 | 182~183 | " |
| 568 | 145~147 | " |
| 569 | 132~133 | " |
| 570 | 170~171 | " |
| 571 | 204~206 | " |

TABLE 4-continued

| Comp. No. | m.p. (°C.) | Status |
|---|---|---|
| 572 | 183~184 | " |
| 573 | 163~165 | " |
| 580 | 185~186 | " |
| 581 | 178~179 | " |
| 210 | 182~185 | " |
| 211 | 177~178 | " |
| 228 | 195~199 | " |
| 389 | 194~195 | " |
| 390 | 192~193 | " |
| 392 | 198~201 | " |
| 394 | 205~207 | " |
| 396 | 142~146 | " |
| 399 | 178~181 | " |
| 425 | 180~183 | " |
| 435 | 189~192 | " |
| 441 | 196~199 | " |
| 442 | 182~184 | " |
| 443 | 178~180 | " |
| 444 | 183~185 | " |
| 445 | 175~178 | " |
| 463 | 162~164 | " |
| 465 | 166~169 | " |
| 484 | 170~175 | " |
| 545 | 185~187 | " |
| 546 | 166~169 | " |
| 595 | 227~230 | " |
| 596 | 215~217 | " |
| 597 | 203~205 | " |
| 598 | 209~211 | " |
| 599 | 189~191 | " |
| 600 | 221~223 | " |
| 601 | 229~230 | " |
| 602 | 252~254 | " |
| 717 | 216~219 | " |
| 718 | 205~208 | " |
| 719 | 202~205 | " |
| 720 | 188~190 | " |
| 721 | 192~194 | " |
| 727 | 174~177 | " |
| 728 | 194~197 | " |
| 729 | 199~201 | " |
| 730 | 174~177 | " |
| 731 | 192~195 | " |
| 733 | 180~183 | " |
| 734 | 179~181 | " |
| 735 | 198~200 | " |
| 737 | 140~142 | " |
| 739 | 195~198 | " |
| 740 | 216~219 | " |
| 741 | 199~203 | " |
| 742 | 189~190 | " |
| 750 | 173~176 | " |
| 766 | 190~193 | " |
| 768 | 167~170 | " |
| 775 | 184~187 | " |
| 776 | 160~162 | " |
| 778 | 162~165 | " |
| 789 | 191~194 | " |
| 790 | 165~168 | " |
| 791 | 176~178 | " |
| 792 | 158~160 | " |
| 793 | 180~183 | " |
| 799 | 194~195 | " |
| 800 | 212~213 | " |
| 801 | 166~168 | " |
| 802 | 170~171 | " |
| 803 | 198~200 | " |
| 815 | 196~198 | " |
| 816 | 183~184 | " |
| 817 | 110~113 | " |
| 818 | 171~172 | " |
| 819 | 163~165 | " |
| 833 | 163~165 | " |
| 834 | 152~154 | " |
| 835 | 170~172 | " |
| 836 | 138~139 | " |
| 837 | 142~144 | " |
| 879 | 212~215 | " |
| 880 | 206~209 | " |
| 881 | 169~172 | " |
| 882 | 175~177 | " |
| 883 | 190~193 | " |
| 884 | 193~195 | " |
| 925 | 178~180 | " |
| 926 | 173~176 | " |
| 927 | 200~201 | " |
| 928 | 156~158 | " |
| 929 | 218~220 | " |
| 930 | 220~222 | " |
| 931 | 189~191 | " |
| 932 | 205~207 | " |
| 933 | 218~220 | " |
| 934 | 213~216 | " |
| 935 | 212~215 | " |
| 936 | 185~186 | " |
| 937 | 182~183 | " |
| 938 | 176~180 | " |
| 939 | 181~184 | " |
| 940 | 182~184 | " |
| 941 | 195~197 | " |
| 942 | 211~213 | " |
| 943 | 197~200 | " |

In application of the compounds of this invention as herbicides, they can be applied by mixing with solid carriers, including for example clay, talc, bentonite, diatomaceous earth and others or liquid carriers, including for example water, alcohols (methanol, ethanol and the like), aromatic hydrocarbons (benzene, toluene, xylene and the like), chlorinated hydrocarbons, ethers, ketones, esters (ethyl acetate, etc.), acid amides and others. They can be provided for practical use with addition of any desired additive selected from a emulsifier, a dispersing agent, a suspending agent, a wetting agent, a spreader and a stablizer and in any desired form such as a soluble concentrate, an emulsifiable concentrate, a wettable powder, a dust, a granule, a suspension concentrate, etc.

In the following, there are shown examples of formulations of herbicides containing the compounds of this invention as active ingredients, but they are not limitative of this invention. In the exemplary formulations shown below, "parts" mean "parts by weight".

Exemplary formulation 1: Wettable powder

| | |
|---|---|
| Compound No. 2 of this invention | 50 parts |
| Ziegleit A | 46 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

All of the above components are mixed and pulverized homogeneously to prepare a wettable powder In use, the above wettable powder is diluted with water to 50 to 50,000 times, and sprayed in an amount of the active ingredient of 0.0005 kg to 10 kg per hectare.

Exemplary formulation 2: Wettable powder

| | |
|---|---|
| Compound No. 86 of this invention | 75 parts |
| Ziegleit A | 19 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku | |

Co., Ltd.)
Carplex (anticaking agent) — 4 parts
(white carbon; trade name, produced by Shionogi Seiyaku Co., Ltd.)

The above components are mixed and pulverized homogeneously to prepare a wettable powder.

Exemplary formulation 3: Wettable powder

| | |
|---|---|
| Compound No. 140 of this invention | 50 parts |
| Ziegleit A | 46 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

Exemplary formulation 4: Wettable powder

| | |
|---|---|
| Compound No. 159 of this invention | 50 parts |
| Ziegleit A | 46 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

Exemplary formulation 5: Wettable powder

| | |
|---|---|
| Compound No. 292 of this invention | 25 parts |
| Ziegleit A | 71 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

Exemplary formulation 6: Wettable powder

| | |
|---|---|
| Compound No. 384 of this invention | 50 parts |
| Ziegleit A | 44 parts |
| (kaolin type clay: produced by Ziegleit Kogyo Co., Ltd.) | |
| Solpol 5039 | 4 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

Exemplary formulation 7: Wettable powder

| | |
|---|---|
| Compound No. 387 of this invention | 45 parts |
| Ziegleit A | 51 parts |
| (kaolin type clay: produced by Ziegleit Kogyo Co., Ltd.) | |
| Solpol 5039 | 2 parts |
| (mixture of nonionic surfactant and anionic surfactant; trade name; produced by Toho Kagaku Co., Ltd.) | |
| Carplex (anticaking agent) | 2 parts |
| (white carbon; trade name, produced by Shionogi Seiyaku Co., Ltd.) | |

The above components are mixed and pulverized homogeneously to prepare a wettable powder.

Exemplary formulation 8: Emulsifiable concentrate

| | |
|---|---|
| Compound No. 817 of this invention | 2 parts |
| Xylene | 78 parts |
| Dimethylformamide | 15 parts |
| Solpol 2680 | 5 parts |
| (mixture of nonionic surfactant and anionic surfactant; trade name; produced by Toho Kagaku Co., Ltd.) | |

The above components are homogeneously mixed to prepare an emulsifiable concentrate. In use, the above emulsifiable concentrate is diluted to 10 to 10,000 times and sprayed in an amount of the active ingredient of 0.0005 to 10 kg per hectare.

Exemplary formulation 9: Suspension concentrate

| | |
|---|---|
| Compound No. 387 of this invention | 25 parts |
| Agrisol S-710 | 10 parts |
| (nonionic surfactant; trade name; produced by Kao-Atlas Co., Ltd.) | |
| Runox 1000 C | 0.5 parts |
| (anionic surfactant; trade name; produced by Toho Kagaku Co., Ltd.) | |
| 1% Rodopol water | 20 parts |
| (thickener; trade name; produced by Rohne Poulainc) | |

The above components are mixed to provide a suspnsion concentrate preparation.

Exemplary formulation 10: Granule

| | |
|---|---|
| Compound No. 816 of this invention | 0.1 parts |
| Bentonite | 55 parts |
| Talc | 44.9 parts |

All of the above components are mixed and pulverized homogeneously, then a little amount of water is added and the whole is stirred, kneaded and granulated by excluding granulator, then dried to prepare a granule.

Exemplary formulation 11: Granule

| | |
|---|---|
| Compound No. 817 of this invention | 0.25 parts |
| Bentonite | 55 parts |
| Talc | 44.57 parts |

All of the above components are mixed and pulverized homogenerously, then a little amount of water is added and the whole is stirred, kneaded and granulated by excluding granulator, then dried to prepare a granule.

Exemplary formulation 12: Granule

| Compound No. 834 of this invention | 0.5 parts |
|---|---|
| Bentonite | 55 parts |
| Talc | 44.5 parts |

All of the above components are mixed and pulverized homogenerously, hen a little amount of water is added and the whole is stirred, kneaded and granulated by excluding granulator, then dried to prepre a granule.

Exemplary formulation 13: Granule

| Compound No. 835 of this invention | 1 part |
|---|---|
| Bentonite | 55 parts |
| Talc | 44 parts |

All of the above components are mixed and pulverized homogeneously, then a little amount of water is added and the whole is stirred, kneaded and granulated by excluding granulator, then dried to prepare a granule.

If desired, the compound of this invention can be applied as a mixture with other kinds of herbicides, various insecticides, sterilizers or adjuvants during preparation or spraying.

As the other kinds of herbicides as mentioned above, there may be included those as described in Farm Chemicals Handbook, 69 th edition (1983).

The compounds of this invention can also be applied, in addition to the agricultural and horticultural fields such as farm fields, paddy fields, fruit gardens and the like, to athletic grounds, vacant lands, belts along the railroads and others. The amounts of the pesticide to be applied, which may differ depending on the scenes to be applied, the time of application, the application method, the kinds of the objective grasses and the crops harvested, may generally range suitably from 0.005 to 10 kg per hectare.

The following test examples are set forth for illustration of the utility of the compounds of this invention as herbicides.

Test example 1: Herbicidal effect test by soil treatment

In a plastic box of 15 cm length, 22 cm width and 6 cm depth, there was placed a deluvium soil, seeds of (A) rice (*Oryza sativa*), (B) barnyardgrass (*Echinochloa crusgalli*), (C) large crabgrass (*Digitaria adscendens*), (D) annual sedge (*Cyperus microiria*), (E) lambsquarters (*Chenopodium ficifolium*), (F) common purslane (*Portulaca cleracea*), (G) hairly galinosoga (*Galinosoga ciliata*), and (H) yellow cress (*Rorippa atrovirens*) were sown mixedly. After covering soil to about 1.5 cm over the seeds, herbicides were sprayed evenly on the soil surface to predetermined proportions of the active ingredient. In spraying, the wettable powder as shown in the foregoing exemplary formulations was diluted with water and sprayed over the entire surface by means of a small sprayer. Four weeks after spraying, the herbicidal effect on rice and the various weeds were examined according to the judgement criteria shown below. The results are shown in Table 5.

Judgement criteria:

5 ... Growth control rates of more than 90% (almost completely withered)
4 ... Growth control rates of 70 to 90%
3 ... Growth control rates of 40 to 70%
2 ... Growth control rates of 20 to 40%
1 ... Growth control rates of 5 to 20%
0 ... Growth control rates of less than 5% (substantially no effect)

The above growth control rates are determined by measuring the top fresh weights of the treated plants and those of the non-treated plants, and calculated from the following formula:

$$\text{Growth control rate (\%)} = 1 - \frac{\text{Top fresh weight of the treated plants}}{\text{Top fresh weight of the non-treated plants}} \times 100$$

TABLE 5

| Comp. No. | Amount of active ingredient applied (kg/ha) | (A) | (B) | (C) | (D) | (E) | (F) | (G) | (H) |
|---|---|---|---|---|---|---|---|---|---|
| 2 | 0.16 | 5 | 5 | 5 | 5 | 5 | 5 | 5 | 5 |
|   | 0.08 | 5 | 5 | 5 | 5 | 5 | 5 | 5 | 5 |
| 3 | 0.16 | 5 | 5 | 5 | 5 | 5 | 5 | 5 | 5 |
|   | 0.08 | 5 | 5 | 5 | 5 | 5 | 5 | 5 | 4 |
| 4 | 0.16 | 5 | 5 | 5 | 5 | 5 | 5 | 5 | 5 |
|   | 0.08 | 5 | 5 | 5 | 5 | 5 | 5 | 5 | 4 |
| 85 | 0.16 | 5 | 5 | 5 | 5 | 5 | 5 | 5 | 5 |
|   | 0.08 | 5 | 5 | 5 | 5 | 5 | 5 | 5 | 5 |
| 86 | 0.16 | 5 | 5 | 5 | 5 | 5 | 5 | 5 | 5 |
|   | 0.08 | 5 | 5 | 5 | 5 | 5 | 5 | 5 | 5 |
| 87 | 0.16 | 5 | 5 | 5 | 5 | 5 | 5 | 5 | 5 |
|   | 0.08 | 5 | 5 | 5 | 5 | 5 | 5 | 5 | 5 |
| 88 | 0.16 | 5 | 5 | 5 | 5 | 5 | 5 | 5 | 5 |
|   | 0.08 | 5 | 5 | 5 | 5 | 5 | 5 | 5 | 5 |
| 111 | 0.16 | 5 | 5 | 5 | 5 | 5 | 5 | 5 | 5 |
|   | 0.08 | 5 | 5 | 5 | 5 | 5 | 5 | 5 | 5 |
| 139 | 0.16 | 5 | 5 | 5 | 5 | 5 | 5 | 5 | 5 |
|   | 0.08 | 5 | 5 | 5 | 5 | 5 | 5 | 5 | 5 |
|   | 0.04 | 5 | 5 | 5 | 5 | 5 | 5 | 5 | 5 |
| 140 | 0.16 | 5 | 5 | 5 | 5 | 5 | 5 | 5 | 5 |
|   | 0.08 | 5 | 5 | 5 | 5 | 5 | 5 | 5 | 5 |
|   | 0.04 | 5 | 5 | 5 | 5 | 5 | 5 | 5 | 5 |
| 141 | 0.16 | 5 | 5 | 5 | 5 | 5 | 5 | 5 | 5 |
|   | 0.08 | 5 | 5 | 5 | 5 | 5 | 5 | 5 | 5 |
|   | 0.04 | 5 | 5 | 5 | 5 | 5 | 5 | 5 | 5 |

TABLE 5-continued

| Comp. No. | Amount of active ingredient applied (kg/ha) | (A) | (B) | (C) | (D) | (E) | (F) | (G) | (H) |
|---|---|---|---|---|---|---|---|---|---|
| 159 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 292 | 0.16 | 5 | 5 | 5 | 5 | 5 | 5 | 5 | 5 |
|  | 0.08 | 5 | 5 | 5 | 5 | 5 | 5 | 5 | 5 |
| 293 | 0.16 | 5 | 5 | 5 | 5 | 5 | 5 | 5 | 5 |
|  | 0.08 | 5 | 5 | 5 | 5 | 5 | 5 | 5 | 3 |
| 294 | 0.16 | 5 | 5 | 5 | 5 | 5 | 5 | 5 | 2 |
|  | 0.08 | 5 | 5 | 5 | 5 | 5 | 5 | 5 | 1 |
| 384 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 385 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 386 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 387 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 388 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 409 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 410 | 0.08 | 5 | 5 | 5 | 5 | 5 | 5 | 5 | 5 |
|  | 0.04 | 5 | 5 | 5 | 5 | 5 | 5 | 5 | 5 |
|  | 0.02 | 5 | 5 | 5 | 5 | 5 | 5 | 5 | 5 |
| 411 | 0.08 | 5 | 5 | 5 | 5 | 5 | 5 | 5 | 5 |
|  | 0.04 | 5 | 5 | 5 | 5 | 5 | 5 | 5 | 5 |
| 392 | 0.16 | 5 | 5 | 5 | 5 | 5 | 5 | 5 | 5 |
|  | 0.08 | 5 | 5 | 5 | 5 | 5 | 5 | 5 | 5 |
| 394 | 0.16 | 5 | 5 | 5 | 5 | 5 | 5 | 5 | 5 |
| 396 | 0.16 | 5 | 5 | 5 | 5 | 5 | 5 | 5 | 5 |
|  | 0.08 | 5 | 5 | 5 | 5 | 5 | 5 | 5 | 5 |
| 425 | 0.16 | 5 | 5 | 5 | 5 | 5 | 5 | 5 | 5 |
|  | 0.08 | 4 | 5 | 5 | 5 | 5 | 5 | 5 | 5 |
| 442 | 0.16 | 5 | 5 | 5 | 5 | 5 | 5 | 5 | 5 |
|  | 0.08 | 4 | 5 | 5 | 5 | 5 | 5 | 5 | 5 |
| 443 | 0.16 | 5 | 5 | 5 | 5 | 5 | 5 | 5 | 5 |
|  | 0.08 | 5 | 5 | 5 | 5 | 5 | 5 | 5 | 5 |
| 444 | 0.16 | 5 | 5 | 5 | 5 | 5 | 5 | 5 | 5 |
|  | 0.08 | 5 | 5 | 5 | 5 | 5 | 5 | 5 | 5 |
| 445 | 0.16 | 5 | 5 | 5 | 5 | 5 | 2 | 5 | 5 |
|  | 0.08 | 5 | 5 | 5 | 5 | 5 | 4 | 5 | 5 |
| 463 | 0.16 | 5 | 5 | 5 | 5 | 5 | 5 | 5 | 5 |
|  | 0.08 | 5 | 5 | 5 | 5 | 5 | 5 | 5 | 5 |
|  | 0.04 | 5 | 5 | 5 | 5 | 5 | 5 | 5 | 5 |
| 465 | 0.16 | 5 | 5 | 5 | 5 | 5 | 5 | 5 | 5 |
|  | 0.08 | 5 | 5 | 5 | 5 | 5 | 5 | 5 | 5 |
|  | 0.04 | 5 | 5 | 5 | 5 | 5 | 5 | 5 | 5 |
| 546 | 0.16 | 5 | 5 | 5 | 5 | 5 | 5 | 5 | 5 |
| 595 | 0.16 | 5 | 5 | 5 | 5 | 5 | 5 | 5 | 5 |
| 596 | 0.16 | 5 | 5 | 5 | 5 | 5 | 5 | 5 | 5 |
| 597 | 0.16 | 5 | 5 | 5 | 5 | 5 | 5 | 5 | 5 |
| 598 | 0.16 | 5 | 5 | 5 | 5 | 5 | 5 | 5 | 5 |
| 599 | 0.16 | 5 | 5 | 5 | 5 | 5 | 5 | 5 | 5 |
| 600 | 0.16 | 5 | 5 | 5 | 5 | 5 | 5 | 5 | 5 |
| 601 | 0.16 | 5 | 5 | 5 | 5 | 5 | 5 | 5 | 5 |
| 734 | 0.16 | 5 | 5 | 5 | 5 | 5 | 5 | 5 | 5 |
|  | 0.08 | 5 | 5 | 5 | 5 | 5 | 5 | 5 | 5 |
|  | 0.04 | 5 | 5 | 5 | 5 | 5 | 5 | 5 | 5 |
| 735 | 0.16 | 5 | 5 | 5 | 5 | 5 | 5 | 5 | 5 |
|  | 0.08 | 5 | 5 | 5 | 5 | 5 | 5 | 5 | 5 |
|  | 0.04 | 5 | 5 | 5 | 5 | 5 | 5 | 5 | 5 |
| 737 | 0.16 | 5 | 5 | 5 | 5 | 5 | 5 | 5 | 5 |
|  | 0.08 | 5 | 5 | 5 | 5 | 5 | 5 | 5 | 5 |
|  | 0.04 | 5 | 5 | 5 | 5 | 5 | 5 | 5 | 5 |
| 815 | 0.16 | 5 | 5 | 5 | 5 | 5 | 5 | 5 | 5 |
|  | 0.08 | 4 | 4 | 4 | 5 | 4 | 4 | 4 | 4 |
| 816 | 0.16 | 5 | 5 | 5 | 5 | 5 | 5 | 5 | 5 |
|  | 0.08 | 5 | 5 | 5 | 5 | 5 | 5 | 5 | 5 |
| 817 | 0.16 | 5 | 5 | 5 | 5 | 5 | 5 | 5 | 5 |
|  | 0.08 | 5 | 5 | 5 | 5 | 5 | 5 | 5 | 5 |
| 818 | 0.16 | 5 | 5 | 5 | 5 | 5 | 5 | 5 | 5 |

TABLE 5-continued

| Comp. No. | Amount of active ingredient applied (kg/ha) | (A) | (B) | (C) | (D) | (E) | (F) | (G) | (H) |
|---|---|---|---|---|---|---|---|---|---|
|  | 0.08 | 5 | 5 | 4 | 5 | 5 | 5 | 5 | 5 |
| 819 | 0.16 | 5 | 5 | 5 | 5 | 5 | 4 | 5 | 4 |
|  | 0.08 | 5 | 4 | 5 | 5 | 4 | 4 | 5 | 4 |
| 833 | 0.16 | 5 | 5 | 5 | 5 | 5 | 5 | 5 | 5 |
|  | 0.08 | 4 | 5 | 4 | 5 | 4 | 4 | 4 | 4 |
| 834 | 0.16 | 5 | 5 | 5 | 5 | 5 | 5 | 5 | 5 |
|  | 0.08 | 5 | 5 | 5 | 5 | 5 | 5 | 5 | 5 |
| 835 | 0.16 | 5 | 5 | 5 | 5 | 5 | 5 | 5 | 5 |
|  | 0.08 | 5 | 5 | 5 | 5 | 5 | 5 | 5 | 5 |
| 836 | 0.16 | 5 | 5 | 5 | 5 | 5 | 5 | 5 | 5 |
|  | 0.08 | 5 | 4 | 4 | 5 | 4 | 5 | 5 | 5 |
| 837 | 0.16 | 5 | 5 | 5 | 5 | 5 | 4 | 5 | 5 |
|  | 0.08 | 5 | 4 | 5 | 5 | 4 | 3 | 4 | 4 |
| Control Compound A | 0.16 | 3 | 2 | 2 | 4 | 3 | 2 | 2 | 3 |
|  | 0.08 | 2 | 0 | 1 | 4 | 1 | 1 | 1 | 3 |
| Control Compound B | 0.16 | 4 | 4 | 3 | 3 | 4 | 3 | 4 | 4 |
|  | 0.08 | 3 | 3 | 3 | 1 | 3 | 2 | 3 | 3 |
| Control Compound C | 0.16 | 3 | 2 | 2 | 4 | 3 | 2 | 2 | 3 |
|  | 0.08 | 2 | 1 | 1 | 2 | 1 | 1 | 1 | 2 |
| Control Compound D | 0.16 | 5 | 4 | 4 | 4 | 3 | 3 | 3 | 4 |
|  | 0.08 | 4 | 3 | 4 | 3 | 3 | 3 | 3 | 3 |

Control Compounds in the above Table 5 are as follows:

Control Comp. B (disclosed in Japanese Unexamined Publn. No. 169688/1981):

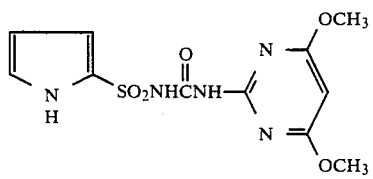

Control Comp. A (disclosed in Japanese Unexamined Publn. No. 169688/1981):

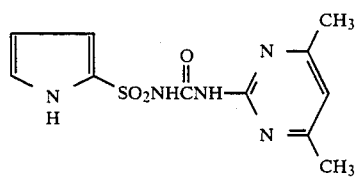

Control Comp. C (disclosed in Japanese Unexamined Publn. No. 169688/1981):

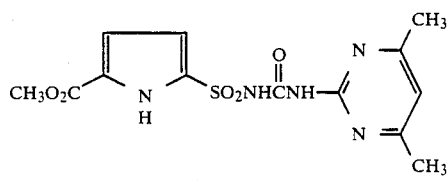

Control Comp. D (disclosed in Japanese Unexamined Publn. No. 102577/1980):

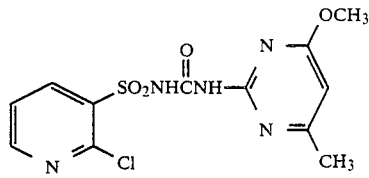

Test example 2: Herbicidal effect test by stem-leaf treatment

In a plastic box of 15 cm length, 22 cm width and 6 cm depth, there was placed a deluvium soil, seeds of (A) rice (*Oryza sativa*), (C) large crabgrass (*Digitaria adscendens*), (D) annual sedge (*Cyperus microiria*), (E) lambsquarters (*Chenopodium ficifolium*), (G) hairly galinosoga (*Galinosoga ciliata*), (H) yellow cress (*Rorippa atrovirens*), (F) corn (*Zea mays*), (J) soybean (*Glysine max*), (K) wheat (*Triticum vulgare*), and (L) tomato (*Lycopersicum esculentum*) were sown in shapes of spots, respectively, followed by covering of soil to about 1.5 cm over the seeds. After respective plants have grown to the second and the third leaf stage, herbicides were sprayed evenly onto the stem-leaf portion at predetermined proportions of the active ingredient.

In spraying, the wettable powder as shown in the foregoing exemplary formulations was diluted with water and sprayed over the entire surface of the stem-leaf portions of various weeds by means of a small sprayer.

Four weeks after spraying, the herbicidal effect on rice and the various plants were examined according to the judgement criteria as shown in Test example 1. The results are shown in Table 6.

Some of the compounds of this invention have selectivities on some kinds of crops.

In the following Table 6, the Control Compounds A, B and D are the same as those in the foregoing Test example 1.

TABLE 6

| Comp. No. | Amount of active ingredient applied (kg/ha) | (A) | (C) | (D) | (E) | (G) | (H) | (I) | (J) | (K) | (L) |
|---|---|---|---|---|---|---|---|---|---|---|---|
| 2 | 0.16 | 5 | 5 | 5 | 5 | 5 | 5 | 5 | 3 | 4 | 2 |
|  | 0.08 | 5 | 5 | 5 | 5 | 5 | 5 | 5 | 2 | 3 | 1 |
| 3 | 0.16 | 4 | 5 | 5 | 5 | 4 | 5 | 5 | 5 | 5 | 5 |
|  | 0.08 | 4 | 5 | 5 | 5 | 4 | 5 | 4 | 4 | 4 | 5 |
| 4 | 0.16 | 5 | 5 | 5 | 5 | 5 | 5 | 5 | 5 | 5 | 4 |
|  | 0.08 | 5 | 5 | 5 | 5 | 5 | 5 | 5 | 5 | 4 | 4 |
| 85 | 0.16 | 5 | 5 | 5 | 5 | 5 | 5 | 5 | 5 | 5 | 5 |
|  | 0.08 | 5 | 4 | 4 | 5 | 4 | 5 | 5 | 5 | 5 | 3 |
| 86 | 0.16 | 5 | 5 | 5 | 5 | 5 | 5 | 5 | 5 | 5 | 1 |
|  | 0.08 | 5 | 5 | 5 | 5 | 5 | 5 | 5 | 5 | 5 | 0 |
| 87 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
| 88 | 0.16 | 5 | 5 | 5 | 5 | 5 | 5 | 5 | 5 | 5 | 5 |
|  | 0.08 | 5 | 5 | 5 | 5 | 5 | 4 | 5 | 5 | 5 | 5 |
| 111 | 0.16 | 5 | 5 | 5 | 5 | 5 | 5 | 5 | 5 | 5 | 4 |
|  | 0.08 | 5 | 5 | 5 | 4 | 4 | 5 | 4 | 4 | 4 | 3 |
| 159 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 4 | 4 |
|  | 0.04 | 5 | 5 | 5 | 5 | 5 | 5 | 5 | 5 | 4 | 3 |
| 293 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 4 | 5 |
| 294 | 0.16 | 5 | 5 | 5 | 5 | 5 | 5 | 5 | 5 | 5 | 4 |
|  | 0.08 | 5 | 5 | 5 | 5 | 5 | 4 | 4 | 4 | 4 | 3 |
| 384 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 |
| 385 | 0.16 | 5 | 5 | 5 | 5 | 5 | 5 | 5 | 5 | 5 | 1 |
|  | 0.08 | 5 | 5 | 5 | 5 | 5 | 5 | 5 | 5 | 5 | 0 |
|  | 0.04 | 5 | 5 | 5 | 5 | 5 | 5 | 5 | 5 | 5 | 0 |
| 386 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 |
| 387 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 |
| 388 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 |
| 409 | 0.16 | 5 | 5 | 5 | 5 | 5 | 5 | 5 | 5 | 5 | 1 |
|  | 0.08 | 5 | 5 | 5 | 5 | 5 | 5 | 5 | 5 | 5 | 0 |
|  | 0.04 | 5 | 5 | 5 | 5 | 5 | 5 | 5 | 5 | 5 | 0 |
| 410 | 0.16 | 5 | 5 | 5 | 5 | 5 | 5 | 5 | 5 | 5 | 2 |
|  | 0.08 | 5 | 5 | 5 | 5 | 5 | 5 | 5 | 5 | 5 | 1 |
|  | 0.04 | 5 | 5 | 5 | 5 | 5 | 5 | 5 | 5 | 5 | 0 |
| 411 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 |
| 392 | 0.16 | 4 | 5 | 5 | 5 | 5 | 3 | 4 | 0 | 4 | 5 |
| 394 | 0.16 | 5 | 4 | 5 | 5 | 5 | 5 | 5 | 5 | 5 | 5 |
| 396 | 0.16 | 5 | 5 | 5 | 5 | 5 | 5 | 5 | 5 | 5 | 5 |
| 425 | 0.16 | 5 | 4 | 5 | 5 | 5 | 5 | 5 | 5 | 5 | 5 |
| 442 | 0.16 | 5 | 5 | 5 | 5 | 5 | 5 | 5 | 5 | 5 | 0 |
|  | 0.08 | 4 | 5 | 5 | 5 | 5 | 4 | 5 | 5 | 4 | 0 |
| 443 | 0.16 | 4 | 5 | 5 | 5 | 5 | 5 | 5 | 5 | 5 | 5 |
|  | 0.08 | 4 | 4 | 5 | 5 | 5 | 5 | 5 | 5 | 5 | 5 |
| 444 | 0.16 | 5 | 5 | 5 | 5 | 5 | 5 | 5 | 5 | 5 | 5 |
|  | 0.08 | 5 | 5 | 5 | 5 | 4 | 5 | 5 | 5 | 5 | 5 |
| 445 | 0.16 | 5 | 5 | 5 | 5 | 5 | 5 | 5 | 5 | 5 | 5 |
|  | 0.08 | 5 | 5 | 5 | 5 | 5 | 4 | 5 | 5 | 5 | 5 |
| 463 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 |
| 465 | 0.16 | 5 | 5 | 5 | 5 | 5 | 5 | 5 | 5 | 5 | 5 |
|  | 0.08 | 5 | 5 | 5 | 5 | 5 | 5 | 5 | 5 | 5 | 5 |
|  | 0.04 | 5 | 5 | 5 | 5 | 5 | 5 | 5 | 5 | 5 | 5 |
| 546 | 0.16 | 5 | 5 | 5 | 5 | 5 | 5 | 5 | 5 | 5 | 5 |
| 595 | 0.16 | 5 | 5 | 5 | 5 | 5 | 5 | 5 | 5 | 5 | 5 |
| 596 | 0.16 | 5 | 5 | 5 | 5 | 5 | 5 | 5 | 5 | 5 | 3 |
| 597 | 0.16 | 5 | 5 | 5 | 5 | 5 | 5 | 5 | 5 | 5 | 5 |
| 598 | 0.16 | 5 | 5 | 5 | 5 | 5 | 5 | 5 | 5 | 5 | 5 |
| 599 | 0.16 | 5 | 5 | 5 | 5 | 5 | 5 | 5 | 5 | 5 | 5 |
| 600 | 0.16 | 5 | 4 | 5 | 5 | 5 | 5 | 5 | 5 | 5 | 5 |
| 601 | 0.16 | 5 | 5 | 4 | 5 | 5 | 5 | 5 | 5 | 5 | 5 |
| 734 | 0.16 | 5 | 5 | 5 | 5 | 5 | 5 | 5 | 5 | 5 | 5 |
|  | 0.08 | 5 | 4 | 5 | 4 | 5 | 4 | 4 | 5 | 5 | 5 |
| 735 | 0.16 | 5 | 5 | 5 | 5 | 5 | 5 | 5 | 5 | 5 | 1 |
|  | 0.08 | 4 | 5 | 5 | 4 | 5 | 4 | 5 | 5 | 5 | 0 |

TABLE 6-continued

| Comp. No. | Amount of active ingredient applied (kg/ha) | (A) | (C) | (D) | (E) | (G) | (H) | (I) | (J) | (K) | (L) |
|---|---|---|---|---|---|---|---|---|---|---|---|
| 737 | 0.16 | 5 | 5 | 5 | 5 | 5 | 5 | 5 | 5 | 5 | 0 |
|  | 0.08 | 5 | 5 | 5 | 4 | 5 | 4 | 5 | 5 | 5 | 0 |
| 815 | 0.16 | 5 | 5 | 5 | 5 | 5 | 5 | 5 | 5 | 2 | 5 |
|  | 0.08 | 5 | 4 | 5 | 5 | 5 | 5 | 5 | 5 | 1 | 4 |
| 816 | 0.16 | 5 | 5 | 5 | 5 | 5 | 5 | 5 | 5 | 4 | 5 |
|  | 0.08 | 5 | 4 | 5 | 5 | 5 | 5 | 5 | 5 | 3 | 5 |
| 817 | 0.16 | 5 | 5 | 5 | 5 | 5 | 5 | 5 | 5 | 2 | 5 |
|  | 0.08 | 4 | 4 | 5 | 5 | 5 | 5 | 5 | 5 | 1 | 4 |
| 818 | 0.16 | 5 | 4 | 5 | 5 | 5 | 5 | 5 | 5 | 2 | 3 |
|  | 0.08 | 4 | 3 | 5 | 5 | 5 | 5 | 5 | 5 | 0 | 1 |
| 819 | 0.16 | 5 | 5 | 5 | 5 | 5 | 5 | 5 | 5 | 3 | 5 |
|  | 0.08 | 4 | 4 | 5 | 5 | 5 | 4 | 4 | 5 | 2 | 4 |
| 833 | 0.16 | 5 | 4 | 5 | 5 | 5 | 5 | 5 | 5 | 2 | 5 |
|  | 0.08 | 5 | 3 | 5 | 5 | 5 | 5 | 5 | 5 | 1 | 4 |
| 834 | 0.16 | 5 | 5 | 5 | 5 | 5 | 5 | 5 | 5 | 3 | 5 |
|  | 0.08 | 5 | 4 | 5 | 5 | 5 | 5 | 5 | 5 | 2 | 3 |
| 835 | 0.16 | 5 | 4 | 5 | 5 | 5 | 5 | 5 | 5 | 2 | 4 |
|  | 0.08 | 4 | 3 | 5 | 5 | 5 | 5 | 5 | 5 | 1 | 2 |
| 836 | 0.16 | 4 | 3 | 5 | 5 | 5 | 5 | 5 | 5 | 2 | 3 |
|  | 0.08 | 3 | 2 | 5 | 4 | 5 | 4 | 4 | 4 | 0 | 1 |
| 837 | 0.16 | 5 | 3 | 5 | 5 | 5 | 5 | 5 | 5 | 2 | 5 |
|  | 0.08 | 4 | 3 | 5 | 4 | 5 | 4 | 4 | 4 | 1 | 4 |
| Control Compound A | 0.16 | 4 | 4 | 4 | 4 | 4 | 4 | 4 | 4 | 4 | 2 |
|  | 0.08 | 3 | 4 | 4 | 4 | 4 | 4 | 4 | 4 | 3 | 2 |
| Control Compound B | 0.16 | 3 | 3 | 3 | 3 | 3 | 3 | 3 | 4 | 2 | 2 |
|  | 0.08 | 3 | 2 | 2 | 3 | 3 | 2 | 3 | 3 | 1 | 2 |
| Control Compound D | 0.16 | 3 | 4 | 3 | 3 | 4 | 3 | 3 | 3 | 2 | 2 |
|  | 0.08 | 3 | 3 | 3 | 3 | 3 | 3 | 3 | 2 | 2 | 2 |

Test example 3: Herbicidal effect test under paddy condition

In a Wagner pot of 1/50 m², there was placed an alluvial soil, water was put thereinto, soil and water were mingled and a paddy condition of 2 cm depth of the water was made. Seeds of (B) barnyardgrass (*Echinochloa crus-galli*), (M) ducksalad (*Monochoria vaginalis*), (N) false pimpernel (*Lindernia procumbens*), (O) toothcup (*Rotala indica*) and (P) bulrush (*Scirpus hotarui*) were sown mixedly therein and tuberns of (Q) arrowhead (*Sagittaria pygmaea*) and (R) perennial flat sedge (*Cyperus serotinus*) were placed thereon. Then, young rice plants of the 2.5 leaf stage were transplanted.

On the next day, the diluted solution containing the compound of this invention was dropped on the water surface in predetermined proportions of the active ingredient.

Three weeks after application, the herbicidal effect on rice and the various weeds were examined according to the judgement criteria as shown in Test Example 1. The results are shown in Table 7.

TABLE 7

| Compound No. | Amount of active ingredient applied (kg/ha) | (A) | (B) | (M) | (N) | (O) | (P) | (Q) | (R) |
|---|---|---|---|---|---|---|---|---|---|
| 816 | 0.04 | 0 | 5 | 5 | 5 | 5 | 5 | 5 | 5 |
|  | 0.02 | 0 | 5 | 5 | 5 | 5 | 5 | 5 | 5 |
|  | 0.01 | 0 | 4 | 5 | 5 | 5 | 5 | 5 | 5 |
| 817 | 0.04 | 0 | 5 | 5 | 5 | 5 | 5 | 5 | 5 |
|  | 0.02 | 0 | 5 | 5 | 5 | 5 | 5 | 5 | 5 |
|  | 0.01 | 0 | 4 | 5 | 5 | 5 | 5 | 5 | 5 |
| 834 | 0.04 | 0 | 5 | 5 | 5 | 5 | 5 | 5 | 5 |
|  | 0.02 | 0 | 5 | 5 | 5 | 5 | 5 | 5 | 5 |
|  | 0.01 | 0 | 4 | 5 | 5 | 5 | 5 | 5 | 5 |
| 835 | 0.04 | 0 | 5 | 5 | 5 | 5 | 5 | 5 | 5 |
|  | 0.02 | 0 | 5 | 5 | 5 | 5 | 5 | 5 | 5 |
|  | 0.01 | 0 | 4 | 5 | 5 | 5 | 5 | 5 | 5 |

We claim:

1. A method of controlling the growth of undesired vegetation in rice growing sites without harming the rice plants which comprises applying to a rice growing site an effective amount of a compound of the formula

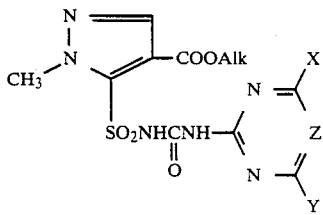

wherein Alk is methyl or ethyl; X is methyl or methoxy; Y is methoxy; and Z is CH.

2. The method of claim 1 wherein, in said compound, Alk is methyl and X is methyl.

3. The method of claim 1 wherein, in said compound, Alk is methyl and X is methoxy.

4. The method of claim 1 wherein, in said compound, Alk is ethyl and X is methyl.

5. The method of claim 1, wherein in said compound, Alk is ethyl and X is methoxy.

* * * * *